US009750250B2

(12) United States Patent
Whitten et al.

(10) Patent No.: US 9,750,250 B2
(45) Date of Patent: Sep. 5, 2017

(54) CONJUGATED POLYELECTROLYTES AND METHODS OF USING THE SAME

(71) Applicants: David G. Whitten, Albuquerque, NM (US); Harry Craig Pappas, Albuquerque, NM (US); Eric H. Hill, Donostia (ES); Kirk S. Schanze, Gainesville, FL (US); Anand Parthasarathy, Gainesville, FL (US); Yun Huang, Gainesville, FL (US); Thomas S. Corbitt, Albuquerque, NM (US)

(72) Inventors: David G. Whitten, Albuquerque, NM (US); Harry Craig Pappas, Albuquerque, NM (US); Eric H. Hill, Donostia (ES); Kirk S. Schanze, Gainesville, FL (US); Anand Parthasarathy, Gainesville, FL (US); Yun Huang, Gainesville, FL (US); Thomas S. Corbitt, Albuquerque, NM (US)

(73) Assignees: STC.UNM, Albuquerque, NM (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/018,179

(22) Filed: Feb. 8, 2016

(65) Prior Publication Data
US 2016/0222150 A1 Aug. 4, 2016

Related U.S. Application Data

(63) Continuation of application No. PCT/US2016/013431, filed on Jan. 14, 2016.

(60) Provisional application No. 62/103,244, filed on Jan. 14, 2015, provisional application No. 62/109,455, filed on Jan. 29, 2015, provisional application No. 62/130,301, filed on Mar. 9, 2015.

(51) Int. Cl.

| | |
|---|---|
| *C08F 238/00* | (2006.01) |
| *A61L 15/44* | (2006.01) |
| *A01N 43/50* | (2006.01) |
| *A61L 15/24* | (2006.01) |
| *A61L 15/46* | (2006.01) |
| *A01N 33/08* | (2006.01) |
| *A01N 33/12* | (2006.01) |
| *A01N 43/90* | (2006.01) |

(52) U.S. Cl.
CPC ............ *A01N 43/50* (2013.01); *A01N 33/08* (2013.01); *A01N 33/12* (2013.01); *A01N 43/90* (2013.01); *A61L 15/24* (2013.01); *A61L 15/46* (2013.01); *A61L 2300/404* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 4,251,386 A | 2/1981 | Saeki et al. | |
| 5,449,809 A | 9/1995 | Wingert et al. | |
| 5,489,400 A | 2/1996 | Liu et al. | |
| 6,743,640 B2 | 6/2004 | Whitten et al. | |
| 6,841,669 B2 | 1/2005 | Cipriani et al. | |
| 7,122,383 B2 | 10/2006 | Jones et al. | |
| 8,455,265 B2 | 6/2013 | Whitten et al. | |
| 8,598,053 B2 | 12/2013 | Whitten et al. | |
| 8,618,009 B2 | 12/2013 | Schanze et al. | |
| 8,753,570 B2 | 6/2014 | Whitten et al. | |
| 9,005,540 B2 | 4/2015 | Schanze et al. | |
| 9,125,415 B2 | 9/2015 | Schanze et al. | |
| 2003/0134959 A1 | 7/2003 | Hancock et al. | |

(Continued)

FOREIGN PATENT DOCUMENTS

| | | |
|---|---|---|
| JP | 3198365 B2 | 8/2001 |
| WO | WO-2008143731 A2 | 11/2008 |

(Continued)

OTHER PUBLICATIONS

"U.S. Appl. No. 13/809,573, Non Final Office Action mailed Aug. 25, 2016", 13 pgs.
"U.S. Appl. No. 13/809,573, Response filed Apr. 22, 2016 to Non-Final Office Action mailed Jan. 22, 2016", 13 pgs.
"International Application Serial No. PCT/US2016/013431, International Search Report mailed Apr. 25, 2016", 3 pgs.
"International Application Serial No. PCT/US2016/013431, Written Opinion mailed Apr. 25, 2016", 7 pgs.

(Continued)

*Primary Examiner* — Ileana Popa
*Assistant Examiner* — Nicole Babson
(74) *Attorney, Agent, or Firm* — Schwegman Lundberg & Woessner, P.A.

(57) ABSTRACT

Various embodiments disclosed relate to conjugated polyelectrolytes and methods of using the same. Various embodiments provide a conjugated polyelectrolyte including a subunit having the structure $-R^1-Y-R^2-Z-$. At each occurrence, $R^1$ is independently chosen from 1,4-bonded phenylene substituted by $-X-R^3-R^4$ j times and 2,5-bonded thiophene substituted by $-X-R^3-R^4$ j times. At each occurrence, Y is independently chosen from a bond and $-C\equiv C-$. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and $-C\equiv C-$. The variables j, $R^3$, and $R^4$ are as defined herein.

20 Claims, 26 Drawing Sheets

(56) References Cited

U.S. PATENT DOCUMENTS

| | | |
|---|---|---|
| 2003/0168756 A1 | 9/2003 | Balkus, Jr. et al. |
| 2003/0178607 A1 | 9/2003 | Swager et al. |
| 2004/0241768 A1 | 12/2004 | Whitten et al. |
| 2005/0059168 A1 | 3/2005 | Bazan et al. |
| 2005/0148254 A1 | 7/2005 | Lu et al. |
| 2006/0120923 A1 | 6/2006 | Swager et al. |
| 2006/0175193 A1 | 8/2006 | Inganas et al. |
| 2007/0215841 A1 | 9/2007 | Ford et al. |
| 2008/0090021 A1 | 4/2008 | Long et al. |
| 2010/0035948 A1 | 2/2010 | Kumar et al. |
| 2010/0285081 A1 | 11/2010 | Chen et al. |
| 2011/0159605 A1 | 6/2011 | Whitten et al. |
| 2011/0223058 A1 | 9/2011 | Whitten et al. |
| 2011/0293470 A1 | 12/2011 | Schanze et al. |
| 2012/0271023 A1 | 10/2012 | Whitten et al. |
| 2013/0210828 A1 | 8/2013 | Whitten et al. |
| 2013/0273800 A1 | 10/2013 | Whitten et al. |
| 2013/0330386 A1 | 12/2013 | Whitten et al. |
| 2014/0086795 A1 | 3/2014 | Schanze et al. |
| 2014/0242148 A1 | 8/2014 | Whitten et al. |
| 2014/0341776 A1 | 11/2014 | Schanze et al. |
| 2015/0132184 A1 | 5/2015 | Whitten et al. |

FOREIGN PATENT DOCUMENTS

| | | |
|---|---|---|
| WO | WO-2009158606 A2 | 12/2009 |
| WO | WO-2009158606 A9 | 12/2009 |
| WO | WO-2010044743 A1 | 4/2010 |
| WO | WO-2010054304 A2 | 5/2010 |
| WO | WO-2011044580 A3 | 4/2011 |
| WO | WO-2012009472 A2 | 1/2012 |
| WO | WO-2012009484 A2 | 1/2012 |
| WO | WO-2012079085 A2 | 6/2012 |
| WO | WO-2013020096 A2 | 2/2013 |
| WO | WO-2013020096 A3 | 2/2013 |
| WO | WO-2013055417 A2 | 4/2013 |
| WO | WO-2013055417 A3 | 4/2013 |
| WO | WO-2015138965 A1 | 9/2015 |
| WO | WO-2016115362 A1 | 7/2016 |

OTHER PUBLICATIONS

Parthasarathy, Anand, "Conjugated Polyelectrolytes with Imidazolium Solubilizing Groups Properties and Application to Photodynamic Inactivation of Bacteria", ACS Applied Materials & Interfaces vol. 7, No. 51, (2015), 28027-28034.

PubChem. Substance Record for SID 76464254, Retrieved from the Internet. <URL: https://pubchem.ncbi.nlm.nih.gov/substance/76464254#section=Top>, (Jun. 12, 2009), 5 pgs.

"U.S. Appl. No. 12/529,390, Examiner Interview Summary mailed Jan. 31, 2012", 3 pgs.

"U.S. Appl. No. 12/529,390, Examiner Interview Summary mailed Nov. 13, 2012", 3 pgs.

"U.S. Appl. No. 12/529,390, Non Final Office Action mailed Jul. 18, 2012", 7 pgs.

"U.S. Appl. No. 12/529,390, Non-Final Office Action mailed Nov. 1, 2011", 11 pgs.

"U.S. Appl. No. 12/529,390, Notice of Allowance mailed Feb. 5, 2013", 10 pgs.

"U.S. Appl. No. 12/529,390, Preliminary Amendment mailed Sep. 1, 2009", 13 pgs.

"U.S. Appl. No. 12/529,390, Response filed May 1, 2012 to Non Final Office Action mailed Nov. 1, 2011", 19 pgs.

"U.S. Appl. No. 12/529,390, Response filed Dec. 18, 2012 to Non Final Office Action mailed Jul. 18, 2012", 16 pgs.

"U.S. Appl. No. 13/001,478 , Response filed Dec. 19, 2013 to Non Final Office Action mailed Oct. 3, 2013", 10 pgs.

"U.S. Appl. No. 13/001,478, Non Final Office Action mailed Oct. 3, 2013", 6 pgs.

"U.S. Appl. No. 13/001,478, Notice of Allowance mailed Jan. 31, 2014", 7 pgs.

"U.S. Appl. No. 13/001,478, Response filed Jul. 11, 2013 to Restriction Requirement mailed Jun. 13, 2013", 9 pgs.

"U.S. Appl. No. 13/001,478, Restriction Requirement mailed Jun. 13, 2013", 7 pgs.

"U.S. Appl. No. 13/128,571, Response filed May 13, 2013 to Non Final Office Action mailed Feb. 13, 2013", 12 pgs.

"U.S. Appl. No. 13/128,571, Response filed Nov. 19, 2012 to Restriction Requirement mailed Oct. 17, 2012", 6 pgs.

"U.S. Appl. No. 13/128,571, Non Final Office Action mailed Feb. 13, 2013", 10 pgs.

"U.S. Appl. No. 13/128,571, Notice of Allowance mailed Aug. 28, 2013", 9 pgs.

"U.S. Appl. No. 13/128,571, Preliminary Amendment filed May 10, 2011", 5 pgs.

"U.S. Appl. No. 13/128,571, Restriction Requirement mailed Oct. 17, 2012", 6 pgs.

"U.S. Appl. No. 13/503,067 , Response filed Mar. 11, 2013 to Non Final Office Action mailed Oct. 10, 2012", 11 pgs.

"U.S. Appl. No. 13/503,067 , Response filed Jul. 11, 2013 to Final Office Action mailed Jun. 6, 2013", 7 pgs.

"U.S. Appl. No. 13/503,067, Final Office Action mailed Jun. 6, 2013", 11 pgs.

"U.S. Appl. No. 13/503,067, Non Final Office Action mailed Oct. 10, 2012", 11 pgs.

"U.S. Appl. No. 13/503,067, Notice of Allowance mailed Aug. 2, 2013", 10 pgs.

"U.S. Appl. No. 13/809,572, Non Final Office Action mailed Sep. 24, 2015", 17 pgs.

"U.S. Appl. No. 13/809,572, Response filed Dec. 16, 2015 to Non-Final Office Action mailed Sep. 24, 2015", 11 pgs.

"U.S. Appl. No. 13/809,573, Non Final Office Action mailed Jan. 22, 2016", 13 pgs.

"U.S. Appl. No. 13/809,573, Preliminary Amendment filed Jan. 10, 2013", 9 pgs.

"U.S. Appl. No. 13/809,573, Response filed Sep. 24, 2015 to Restriction Requirement mailed Jul. 24, 2015", 9 pgs.

"U.S. Appl. No. 13/809,573, Restriction Requirement mailed Jul. 24, 2015", 7 pgs.

"U.S. Appl. No. 13/993,026 Response filed Sep. 8, 2015 to Final Office Action mailed Jun. 8, 2015", 10 pgs.

"U.S. Appl. No. 13/993,026, Advisory Action mailed Sep. 17, 2015", 7 pgs.

"U.S. Appl. No. 13/993,026, Final Office Action mailed Jun. 8, 2015", 15 pgs.

"U.S. Appl. No. 13/993,026, Non Final Office Action mailed Jan. 27, 2015", 9 pgs.

"U.S. Appl. No. 13/993,026, Preliminary Amendment filed Jun. 10, 2013", 7 pgs.

"U.S. Appl. No. 13/993,026, Response filed Apr. 9, 2015 to Non Final Office Action mailed Jan. 27, 2015", Response to Non Final Office Action, 11 pgs.

"U.S. Appl. No. 14/092,409, Notice of Allowance mailed Dec. 10, 2014", 10 pgs.

"U.S. Appl. No. 14/127,465, Non Final Office Action mailed Jan. 21, 2015", 4 pgs.

"U.S. Appl. No. 14/127,465, Notice of Allowance mailed Apr. 30, 2015", 7 pgs.

"U.S. Appl. No. 14/127,465, Response filed Apr. 20, 2015 to Non Final Office Action mailed Jan. 21, 2015", 9 pgs.

"U.S. Appl. No. 14/233,130, Response filed Dec. 10, 2015 to Restriction Requriement mailed Oct. 22, 2015", 12 pgs.

"U.S. Appl. No. 14/233,130, Non Final Office Action mailed Jan. 14, 2016", 14 pgs.

"U.S. Appl. No. 14/233,130, Restriction Requirement mailed Oct. 22, 2015", 11 pgs.

"U.S. Appl. No. 14/533,612, Notice of Publication mailed", 1 pg.

"European Application Serial No. 09771137.8, Office Action mailed Feb. 9, 2011", 1 pg.

"European Application Serial No. 09771137.8, Office Action mailed Feb. 14, 2011", 2 pgs.

"European Application Serial No. 09771137.8, Office Action mailed Mar. 3, 2011", 1 pg.

(56) References Cited

OTHER PUBLICATIONS

"European Application Serial No. 09771137.8, Office Action mailed Mar. 16, 2011", 1 pg.
"European Application Serial No. 09771137.8, Response filed Feb. 18, 2011 to Office Action mailed Feb. 9, 2011", 6 pgs.
"International Application Serial No. PCT/US2008/002756, International Preliminary Report on Patentability mailed Sep. 1, 2009", 6 pgs.
"International Application Serial No. PCT/US2008/002756, International Search Report mailed Feb. 25, 2009", 2 pgs.
"International Application Serial No. PCT/US2008/002756, Written Opinion mailed Feb. 25, 2009", 5 pgs.
"International Application Serial No. PCT/US2009/048838, International Preliminary Report on Patentability mailed Jan. 5, 2011", 7 pgs.
"International Application Serial No. PCT/US2009/048838, International Search Report mailed Apr. 30, 2010", 4 pgs.
"International Application Serial No. PCT/US2009/048838, Written Opinion mailed Apr. 30, 2010", 6 pgs.
"International Application Serial No. PCT/US2009/063715, International Preliminary Report on Patentability mailed May 10, 2011", 6 pgs.
"International Application Serial No. PCT/US2009/063715, International Search Report mailed May 27, 2010", 4 pgs.
"International Application Serial No. PCT/US2009/063715, Written Opinion mailed May 27, 2010", 5 pgs.
"International Application Serial No. PCT/US2010/052332, International Preliminary Report on Patentability mailed Apr. 11, 2012", 7 pgs.
"International Application Serial No. PCT/US2010/052332, International Search Report mailed Jun. 24, 2011", 4 pgs.
"International Application Serial No. PCT/US2010/052332, Written Opinion mailed Jun. 24, 2011", 6 pgs.
"International Application Serial No. PCT/US2011/043908, International Preliminary Report on Patentability mailed Jan. 15, 2013", 7 pgs.
"International Application Serial No. PCT/US2011/043908, International Search Report and Written Opinion mailed Apr. 6, 2012", 11 pgs.
"International Application Serial No. PCT/US2011/043922, International Preliminary Report on Patentability mailed Jan. 15, 2013", 4 pgs.
"International Application Serial No. PCT/US2011/043922, International Search Report mailed Mar. 19, 2012", 3 pgs.
"International Application Serial No. PCT/US2011/043922, Written Opinion mailed Mar. 19, 2012", 3 pgs.
"International Application Serial No. PCT/US2011/064460, International Preliminary Report on Patentability mailed Jun. 20, 2013", 7 pgs.
"International Application Serial No. PCT/US2011/064460, International Search Report mailed Jun. 19, 2012", 6 pgs.
"International Application Serial No. PCT/US2011/064460, Written Opinion mailed Jun. 19, 2012", 5 pgs.
"International Application Serial No. PCT/US2012/045598, International Preliminary Report on Patentability mailed Jan. 23, 2014", 6 pgs.
"International Application Serial No. PCT/US2012/045598, International Search Report mailed May 27, 2013", 3 pgs.
"International Application Serial No. PCT/US2012/045598, Written Opinion mailed May 27, 2013", 4 pgs.
"International Application Serial No. PCT/US2012/049613, International Preliminary Report on Patentability mailed Feb. 13, 2014", 9 pgs.
"International Application Serial No. PCT/US2012/049613, International Search Report mailed Feb. 26, 2013", 3 pgs.
"International Application Serial No. PCT/US2012/049613, Written Opinion mailed Feb. 26, 2013", 7 pgs.
"International Application Serial No. PCT/US2015/020546, International Search Report mailed Aug. 10, 2015", 4 pgs.
"International Application Serial No. PCT/US2015/020546, Invitation to Pay Additional Fees and Partial Search Report mailed May 20, 2015", 2 pgs.
"International Application Serial No. PCT/US2015/020546, Written Opinion mailed Aug. 10, 2015", 5 pgs.
Ambade, A. V. et al., "Fluorescent Polyelectrolytes as Protein Sensors", In: Polym. Int., 2007, vol. 56, (2007), 474-481.
Antoci, Jr., Valentin, et al., "Vancomycin covalently bonded to titanium alloy prevents bacterial colonization", Journal of Orthopaedic Research, 25(7), (2007), 858-866.
Arnt, Lachelle, et al., "Cationic Facially Amphiphilic Poly(phenylene ethynylene)s Studied at the Air-Water Interface", Langmuir, 19(6), (2004), 2404-2408.
Arnt, Lachelle, et al., "New Poly(phenyleneethynylene)s with Cationic, Facially Amphiphilic Structures", Journal of the American Chemical Society,124(26), (2002), 7664-7665.
Arnt, Lachelle, et al., "Nonhemolytic Abiogenic Polymers as Antimicrobial Peptide Mimics", J. Polym. Sci., Part A: Polym. Chem., 42(15), (2004), 3860-3864.
Bartlett, Grant R., "Phosphorus Assay in Column Chromatography", The Journal of Biological Chemistry, 234(3), (1959), 466-468.
Beaujuge, Pierre M., et al., "Spectral Engineering in pie-Conjugated Polymers with Intramolecular Donor-Acceptor Interactions", Accounts of Chemical Research, 43(11), (Nov. 2010), 1396-1407.
Beckloff, Nicholas, et al., "Activity of an Antimicrobial Peptide Mimetic against Planktonic and Biofilm Cultures of Oral Pathogens", Antimicrobial Agents and Chemotherapy, 51, (2007), 4125-4132.
Bruns, R., et al., "Chapter 3—R&D in material protection: New biocides", In: Directory of Microbicides for the Protection of Materials—A Handbook, Paulus, W., Editor, (2005), 25-46.
Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63, (2010), 116-124.
Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.
Chemburu, Sireesha, et al., "Light-Induced Biocidal Action of Conjugated Polyelectrolytes Supported on Colloids", Langmuir, 24, (2008), 11053-11062.
Choi, W. S., et al., "Synthesis of Two Types of Nanoparticles in Polyelectrolyte Capsule Nanoreactors and Their Dual Functionality", J. Am. Chem. Soc., 127, (2005), 16136-16142.
Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.
Corbitt, Thomas, et al., "Antimicrobial Non-woven Fibrous Materials", U.S. Appl. No. 61/528,603, filed Aug. 29, 2011, 17 pgs.
Corbitt, Thomas S., et al., "Conjugated Polyelectrolyte Capsules: Light-Activated Antimicrobial Micro "Roach Motels" †", ACS Appl. Mater. Interfaces, 1(1), (2009), 48-52.
Corbitt, Thomas S., et al., "Light and dark biocidal activity of cationic poly(arylene ethynylene) conjugated polyelectrolytes", Photochem. Photobiol. Sci., 8, (2009), 998-1005.
Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.
Dascier, Dimitri, et al., "Efficacy of End-Only-Functionalized Oligo(arylene-ethynylene)s in Killing Bacterial Biofilms", Langmuir, 28(31), (2012), 11286-11290.
De Geest, B. G., et al., "Release mechanisms for polyelectrolyte capsules", Chem. Soc. Rev., 36, (2007), 636-649.
Ding, Liping, et al., "Insight into the Mechanism of Antimicrobial Poly(phenylene ethynylene) Polyelectrolytes: Interactions with Phosphatidylglycerol Lipid Membranes", Langmuir, 25(24), (2009), 13742-13751.
Donlan, Rodney M., et al., "Microbial Life on Surfaces", Emerging Infectious Diseases, 8(9), (2002), 881-890.

(56) References Cited

OTHER PUBLICATIONS

Eun, Ye-Jin, et al., "Fabrication of Microbial Biofilm Arrays by Geometric Control of Cell Adhesion", Langmuir, 25(8), (2009), 4643-4654.

Fan, Qu-Li, et al., "Water-Soluble Cationic Poly(p-phenyleneethynylene)s (PPEs): Effects of Acidity and Ionic Strength on Optical Behavior.", Macromolecules.vol. 38, (2005), 2927-2936.

Fang, Zhen, et al., "Low-Bandgap Donor-Acceptor Conjugated Polymer Sensitizers for Dye-Sensitized Solar Cells", Journal of the American Chemical Society, 133(9), (2011), 3063-3069.

Ferreira, Isabel C.F.R, et al., "Screening of antimicrobial activity of diarylamines in the 2,3,5-trimethylbenzo[b]thiophene series a structure-activity evaluation study", Bioorganic & Medicinal Chemistry Letters, 14(23), (2004), 5831-5833.

Galaev, Igor Y., "'Smart' polymers in biotechnology and medicine", Russian Chemical Reviews, 64(5), (1995), 471-489.

Gao, Yuan, et al., "Recent Advances in Antimicrobial tTeatment of Textiles", Textile Research Journal, 78(1), (2008), 60-72.

George, Wayne N., et al., "Amplified fluorescence quenching in high ionic strength media.", Soft Matter. vol. 3, (2007), 1381-1387.

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hill, Eric, et al., "Molecular Dynamics Simulation Study of the Interaction of Cationic Biocides with Lipid Bilayers: Aggregation E?ects and Bilayer Damage", Langmuir 28, (2012), 14849-14854.

Hoffman, Allan S., "Bioconjugates of Intelligent Polymers and Recognition Proteins for Use in Diagnostics and Affinity Separations", Clinical Chemistry, 46:9, (2000), 1478-1486.

Hortholary, Cedric, et al., "An Approach to Long and Unsubstituted Molecular Wires:? Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ibraeva, Zhanar E., et al., "Solution Properties and Complexation of Polyampholytes based on N,N-Dimethyldiallyl-ammonium Chloride and Maleic Acid or Alkyl (Aryl) Derivatives of Malemic Acids", Macromol. Chem. Phys., 205, (2004), 2464-2472.

Ista, Linnea K., et al., "Conjugated-Polyelectrolyte-Grafted Cotton Fibers Act as "Micro Flypaper" for the Removal and Destruction of Bacteria", ACS Applied Materials & Interfaces, 3(8), (2011), 2932-2937.

Ji, E., "Conjugated polyelectrolytes: Synthesis, photophysical studies and applications to sensors and biocidal activity", Ph.D, dissertation, Univ. of Florida, 2009, (2009), 167 pgs.

Ji, E., et al., "pH-Dependent Optical Properties of a Poly(phenylene ethynylene) Conjugated Polyampholyte", In: Langmuir, vol. 27, (Dec. 28, 2010), 1565-1568.

Ji, Eunkyung, et al., "Antibacterial Activity of Conjugated Polyelectrolytes with Variable Chain Lengths", Langmuir, 27, (2011), 10763-10769.

Ji, Eunkyung, et al., "Light and Dark-Activated Biocidal Activity of Conjugated Polyelectrolytes", ACS Applied Materials & Interfaces, 3(8), (2011), 2820-2829.

Jiang, Hui, et al., "Conjugated Polyelectrolytes: Synthesis, Photophysics, and Applications", Angew. Chem. Int. Ed., 48(24), (2009), 4300-4316.

Jiang, Hui, et al., "Effects of Polymer Aggregation and Quencher Size on Amplified Fluorescence Quenching of Conjugated Polyelectrolytes", Langmuir, 23(18), (2007), 9381-9486.

Kenawy, El-Refaie, et al., "The Chemistry and Applications of Antimicrobial Polymers: A State-of-the-Art Review", Biomacromolecules, 8(5), (2007), 1359-1384.

Kilger, Robert, et al., "Bidirectional energy transfer between the triplet T1 state of photofrin and singlet oxygen in deuterium oxide", Chemical Physics Letter 343, (2001), 543-548.

Kim, Chae Kyu, et al., "Complexation of Anionic Conjugated Polyelectrolyte with Cationic Surfactant", Macromolecular Research, vol. 13 No. 5, (2005), 460-462.

Kim, Sook Kyung, et al., "Chemosensors for Pyrophosphate". Accounts of Chemical Research 42, (2009), 23-31.

Kolb, Hartmuth C., et al., "Click Chemistry: Diverse Chemical Function from a Few Good Reactions", Angew. Chem. Int. Ed., 40, (2001), 2004-2021.

Kotz, Joachim, "Inter- and intramolecular interactions in polyelectrolyte complex formation with polyampholytes", Macromolecular Chemistry and Physics, 194(2), (1993), 397-410.

Leach, Michelle K., et al., "Electrospinning Fundamentals: Optimizing Solution and Apparatus Parameters", Journal of Visualized Experiments, 47, (2011), 4 pgs.

Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.

Lee, Wen-Fu, et al., "Synthesis and solubility of the poly(sulfobetaine)s and the corresponding cationic polymers: 2. Aqueous solution properties of poly[ N,N'-dimethyl-(acrylamido propyl)ammonium propane sulfonate]", Polymer, 36(2), (1995), 357-364.

Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C., 113(2), (2009), 755-764.

Lindsay. D., et al., "Bacterial biofilms within the clinical setting: what healthcare professionals should know", Journal of Hospital Infection, 64, (2006), 313-325.

Liu, Yan, et al., "Conjugated Polyelectrolyte-Based Real-Time Fluorescence Assay for Alkaline Phosphatase with Pyrophosphate as Substrate", Anal. Chem. 80, (2008), 8605-8612.

Liu, Yan, et al., "Conjugated polyelectrolytes as fluorescent sensors", Journal of Photochemistry and Photobiology C: Photochemistry Reviews, 10(4), (2009), 173-190.

Lowe, Andrew B., et al., "Synthesis and Solution Properties of Zwitterionic Polymers", Chem. Rev., 102, (2002), 4177-4189.

Lu, L., et al., "Biocidal Activity of a Light-Absorbing Fluorescent Conjugated Polyelectrolyte", Langmuir, 21, (2005), 10154-10159.

Lu, Timothy K., et al., "Dispersing biofilms with engineered enzymatic bacteriophage", Proc. Natl. Acad. Sci. USA, 104(27), (2007), 11197-11202.

Maisch, Tim, et al., "The role of singlet oxygen and oxygen concentration in photodynamic inactivation of bacteria", The National Academy of Sciences of the USA. PNAS vol. 104, No. 17, (2007), 7223-7228.

McCormick, C. L., "Polyampholytes (Overview)", In: Polymeric Materials Encyclopedia, vol. 7, CRC Press, Boca Raton, FL, (1996), 5462-5476.

McQuade, D. Tyler, et al., "Signal Amplification of a Turn-On Sensor: Harvesting the Light Captured by a Conjugated Polymer", J. Am. Chem. Soc., 122, (2000), 12389-12390.

Notestein, Justin M., et al., "Covalent Grafting of m-Phenylene-Ethynylene Oligomers to Oxide Surfaces", Chem. Mater., 22, (2010), 5319-5327.

Ogawa, Katsu, et al., "Conjugated Polyelecrolyte-Grafted Silica Microspheres", Langmuir, 23(8), (2007), 4541-4548.

Olson, Merle E. et al., "Biofilm bacteria: formation and comparative susceptibility to antibiotics", Canadian Journal of Veterinary Research—Revue Canadienne De Recherche Veterinaire, 66, (2002), 86-92.

Pasquier, Nicolas, et al., "From Multifunctionalized poly(ethylene Imine)s toward Antimicrobial Coatings", Biomacromolecules, 8, (2007), 2874-2882.

Patel, Dinesh G., et al., "It Takes More Than an Imine: The Role of the Central Atom on the Electron-Accepting Abilitty of Benzotriazole and Benzothiadiazole Oligomers", Journal of the American Chemical Society, 134(5), (2012), 2599-2612.

(56) References Cited

OTHER PUBLICATIONS

Pinto, Mauricio, et al., "Amplified fluorescence quenching and biosensor application of a poly( para-phenylene) cationic polyelectrolyte", Res. Chem. Intermed. 33, (2007), 79-90.
Pinto, Mauricio R., et al., "Amplified fluorescence sensing of protease activity with conjugated polyelectrolytes", Proc. Natl. Acad. Sci. USA, 101(20), (2004), 7505-7510.
Pinto, Mauricio R., et al., "Conjugated Polyelectrolytes: Synthesis and Applications", Synthesis, 9, (2002), 1293-1309.
Potera, Carol, "C. Microbiology—Forging a Link Between Biofilms and Disease", Science, 283(5409), (1999), 1837-1939.
Reddinger, Jerry L., et al., "Molecular Engineering of p-Conjugated Polymers", Radical Polymerisation Polyelectrolytes, Series: Advances in Polymer Science, vol. 145, (1999), 57-122.
Schanze, K. S, et al., "Functional Polyelectrolytes", In: Langmuir, 2009, vol. 25, (2009), 13698-13702.
Schild, H. G., "Poly(N-Isopropylacrylamide): Experiment, Theory and Application", Prog. Polym. Sci., 17, (1992), 163-249.
Schlüter, A. D., "The Tenth Anniversary of Suzuki Polycondensation (SPC)", Journal of Polymer Science Part A: Polymer Chemistry, 39(10), (2001), 1533-1556.
Senthilkumar, Sadasivam, et al., "Photophysical properties of coumarin-30 dye in aprotic and protic solvents of varying polarities", Photochemistry and Photobiology, 80, (2004), 104-111.
Shi, Songqing, et al., "Synthesis and Characterization of a Water-Soluble Poly(p-phenylenevinylene) Derivative", Macromolecules, 23(8), (1990), 2119-2124.
Stewart, Philip S., et al., "Physiological heterogeneity in biofilms", Nature Reviews Microbiology, 6, (Mar. 2008), 199-210.
Tan, C. et al., "Photophysics, aggregation and amplified quenching of a water-soluble poly(phenylene ethynylene)", Chem. Commun., (2002), 446-447.
Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.
Tan, Chunyan, et al., "Amplified Quenching of a Conjugated Polyelectrolyte by Cyanine Dyes", J. Am. Chem. Soc., 126, (2004), 13685-13694.
Tan, Chunyan, et al., "Photophysics, aggregation and amplified quenching of a water-soluble poly(phenylene ethynylene)", Chem. Commun., (2002), 446-447.
Tan, Chunyan, et al., "Solvent-Induced Self-Assembly of a Meta-Linked Conjugated Polyelectrolyte. Helix Formation, Guest Intercalation, and Amplified Quenching", Advanced Materials, 16(14), with Supporting Materials, (2004), 1208-1212 (16 pgs.).
Tang, Yanli, et al., "Light-induced antibacterial activity of symmetrical and asymmetrical oligophenylene ethynylenes", Langmuir, 27(8), (2011), 4956-4962.
Tang, Yanli, et al., "Synthesis, Self-Assembly, and Photophysical Behavior of Oligo Phenylene Ethynylenes: From Molecular to Supramolecular Properties", Langmuir, 25(1), (2009), 21-25.
Tang, Yanli, et al., "Synthesis, Self-Assembly, and Photophysical Properties of Cationic Oligo(p-phenyleneethynylene)s", Langmuir, 27(8), (2011), 4945-4955.
Tew, G. N. et al., "", Biochimica et Biophysica Acta 2006, (2006), 1387-1392.
Thomas, III, Samuel W., et al., "Chemical Sensors Based on Amplifying Fluorescent Conjugated Polymers", Chem. Rev., 107, (2007), 1339-1386.
Tiller, J. C., et al., "Designing surfaces that kill bacteria on contact", Proc. Natl. Acad. Sci. USA, 98(11), (May 22, 2001), 5981-5985.
Tong, W., et al., "Single Polyelectrolyte Microcapsules Fabricated By Glutaraldehyde-Mediated Covalent Layer-By-Layer Assembly", Macromol. Rapid Commun., 27, (2006), 2078-2083.
Valle, Jaione, et al., "Broad-spectrum biofilm inhibition by a secreted bacterial polysaccharide", Proc. Natl. Acad. Sci. USA, 103(33), (2006), 12558-12563.
Wallow, Thomas I., et al., "In Aqua Synthesis of Water-Soluble Poly(p-phenylene) Derivatives", J. Am. Chem. Soc., 113, (1991), 7411-7412.
Wang, et al., "Membrane Perturbation Activity of Cationic Phenylene Ethynylene Oligomers and Polymers", (Jun. 29, 2010).
Wang, Deli, et al., "Biosensors from conjugated polyelectrolyte complexes", Proc. Natl. Acad. Sci. USA, 96, (1999), 12287.
Wang, Deli, et al., "Photoluminescence Quenching of Conjugated Macromolecules by Bipyridinium Derivatives in Aqueous Media: Charge Dependence", Langmuir, 17, (2001), 1262-1266.
Wang, Ying, et al., "Direct Visualization of Bactericidal Action of Cationic Conjugated Polyelectrolytes and Oligomers", Langmuir, 28, (2012), 65-70.
Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.
Wang, Yingsheng, et al., "Photochemical probes of intramolecular electronc and energy transfer", Chemical Physics, 176, (1993), 305-319.
Wang, Z., et al., "Preparation and application of single polyelectrolyte microcapsules possessing tunable autofluorescent properties.", Colloids and Surfaces A: Physicochemical and Engineering Aspects, 329, (2008), 58-66.
Wosnick, Jordan H., et al., "Synthesis and Application of Poly(phenyleneEthynylene)s for Bioconjugation: A Conjugated Polymer-Based Fluorogenic Probe", American Chemical Society,127, (2005), 3400-3405.
Xu, Shimei, et al., "Effect of the Anionic-Group/Cationic-Group Ratio on the Swelling Behavior and Controlled Release of Agrochemicals of the Amphoteric, Superabsorbent Polymer Poly(acrylic acid-co-diallyldimethylammonium chloride)", Journal of Applied Polymer Science, 102, (2006), 986-991.
Yang, Chaoyong James, et al., "Direct Synthesis of an Oligonucleotide-Poly-(phenylene ethynylene) Conjugate with a Precise One-to-One Molecular Ratio", Angew. Chem. Int. Ed. 44, (2005), 2572-2576.
Zhai, Lei, et al., "A Simple Method to Generate Side-Chain Derivatives of Regioregular Polythiophene via the GRIM Metathesis and Post-polymerization Functionalization", Macromolecules 36, (2003), 61-64.
Zhang, Lian-Hui, et al., "Quorum sensing and signal interference: diverse implications", Molecular Microbiology, 53(6), (2004), 1563-1571.
Zhao, Xiaoyong, et al., "Variable Band Gap Poly(arylene ethynylene) Conjugated Polyelectrolytes", Macromolecules, 39, (2006), 6355-6366.
Zhinjou, Zhou, "Studies of a cyanine-based biosensor and light-induced antibacterial activities of oligophenyleneethynylenes", (Feb. 9, 2011).
Zhou, Zhijun, et al., "End-Only Functionalized Oligo(phenylene ethynylene)s: Synthesis, Photophysical and Biocidal Activity", Journal of Physical Chemistry Letters, 1(21), (2010), 3207-3212.
Zhu, Huiguang, et al., "Synthesis of Size-Controlled Monodisperse Manganese Carbonate Microparticles as Templates for Uniform Polyelectrolyte Microcapsule Formation.", Chem. Mater.,17, (2005), 2323-2328.
"U.S. Appl. No. 13/809,573, Final Office Action mailed Dec. 15, 2016", 15 pgs.
"U.S. Appl. No. 13/809,573, Response filed Sep. 22, 2016 to Non-Final Office Actino mailed Aug. 25, 2016", 18 pgs.

CONJUGATED POLYELECTROLYTES AND METHODS OF USING THE SAME

CROSS-REFERENCE TO RELATED APPLICATIONS

This application is a continuation under 35 U.S.C. §111(a) and claims benefit of priority to International Patent Application Serial No. PCT/2016/01.3431, filed Jan. 14, 2016, which claims the benefit of priority to U.S. Provisional Patent Application Ser. No. 62/103,244 filed Jan. 14, 2015, to U.S. Provisional Patent Application Ser. No. 62/109,455 filed Jan. 29, 2015, and to U.S. Provisional Patent Application Ser. No. 62/130,301 filed Mar. 9, 2015, the disclosures of which are incorporated herein in their entirety by reference.

STATEMENT OF GOVERNMENT SUPPORT

This invention was made with Government support under HDTRA 1-11-1-0004 and HDTRA1-08-1-0053, both awarded by the Defense Threat Reduction Agency (DTRA) The U.S. Government has certain rights in this invention.

BACKGROUND

Conjugated polyelectrolytes ("CPE" or "CPEs") tend to form π-stacked aggregates in aqueous medium—a challenge that needs to be overcome for various reasons. For example, aggregation of CPEs deactivates the excited state (singlet and triplet) by a non-radiative pathway (e.g., "aggregation induced quenching," or "AIQ"). Further, it is clearly established that the triplet-excited state plays an important role in sensitizing singlet oxygen and other reactive oxygen species that are essential in deactivating pathogenic bacteria. See e.g., Ji, E. Corbitt, T. S.; Parthasarathy, A.; Scharize, K. S.; Whitten, D. G. *ACS Appl. Mater. Interfaces* 2011, 3, 2820; Kilger, R.; Maier, M.; Szeimies, R. M.; Baumler, W. *Chem. Phys. Lett.* 2001, 343, 543; and Maisch, T.; Baler, J.; Franz, B.; Maier, M.; Landthater, M.; Szeimies, R.-M.; Baumler, W. *Proc. Natl. Acad. Sci. U.S.A.* 2007, 104, 7223. In addition; aggregation of the CPE chains may diminish their propensity to interact with bacterial membranes. This interaction is critical for Me generated singlet oxygen to effectively interact with bacterial membranes and cause cell death. See e.g., i, E.; Corbin, T. S.; Parthasarathy, A. Schanze, K. S.; Whitten, D. G. *ACS Appl. Mater. Interfaces* 2011, 3, 2820; and Hill, E. H.; Stratton, K.; Whitten, D. G.; Evans, D. G. *Langmuir* 2012, 28, 14849.

SUMMARY OF THE INVENTION

In various embodiments, the present invention provides a conjugated polyelectrolyte including a subunit having the following structure:

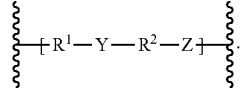

At each occurrence, $R^1$ is independently chosen from:

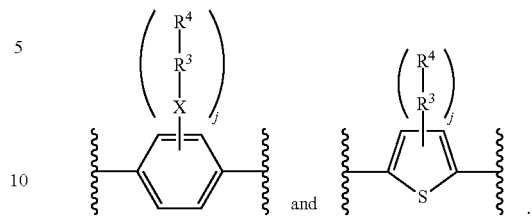

At each occurrence, j is independently chosen from 0, 1, 2, 3, and 4. At each occurrence, X is a bond, —O—, —NH—, or —S—. At each occurrence, $R^3$ is a $(C_1$-$C_{20})$hydrocarbylene interrupted by 0, 1, 2, 3, 4, 5, 6, 7, 8, or 9 heteroatoms. At each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ is independently chosen from a substituted or unsubstituted $(C_1$-$C_{10})$hydrocarbyl. At each occurrence, Y is independently chosen from a bond and —C≡C—. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and —C≡C—.

In various embodiments, the present invention provides a method of inactivating a microorganism. The method includes contacting the microorganism with an effective amount or concentration of a conjugated polyelectrolyte including a subunit having the following structure:

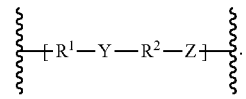

At each occurrence, $R^1$ is independently chosen from:

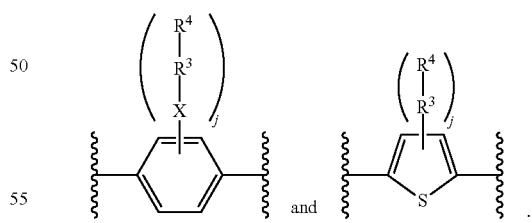

At each occurrence, j is independently chosen from 0, 1, 2, 3, and 4. At each occurrence, X is a bond, —O—, —NH—, or —S—. At each occurrence, $R^3$ is a $(C_1$-$C_{20})$hydrocarbylene interrupted by 0, 1, 2, 3, 4, 5, 6, 7, 8, or 9 heteroatoms. At each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ is independently chosen from a substituted or unsubstituted $(C_1$-$C_{10})$hydrocarbyl. At each occurrence, Y is independently chosen from a bond and —C≡C—. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and —C≡C—.

In various embodiments, the present invention provides a method of disinfecting an object. The method includes contacting the object with an effective amount or concentration of a conjugated polyelectrolyte including a subunit having the following structure:

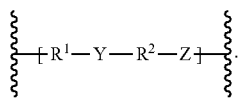

At each occurrence, $R^1$ is independently chosen from:

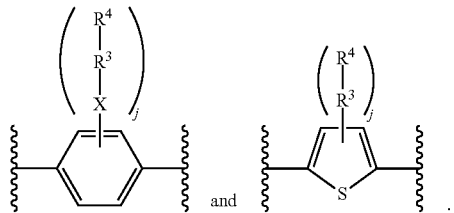

At each occurrence, j is independently chosen from 0, 1, 2, 3, and 4. At each occurrence, X is a bond, —O—, —NH—, or —S—. At each occurrence, $R^3$ is a $(C_1\text{-}C_{20})$hydrocarbylene interrupted by 0, 1, 2, 3, 4, 5, 6, 7, 8, or 9 heteroatoms. At each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ is independently chosen from a substituted or unsubstituted $(C_1\text{-}C_{10})$hydrocarbyl. At each occurrence, Y is independently chosen from a bond and —C≡C—. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and —C≡C—.

In various embodiments, the present invention provides an antimicrobial substrate. The antimicrobial substrate includes an antimicrobial compound that a conjugated polyelectrolyte including a subunit having the following structure:

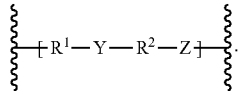

At each occurrence, $R^1$ is independently chosen from:

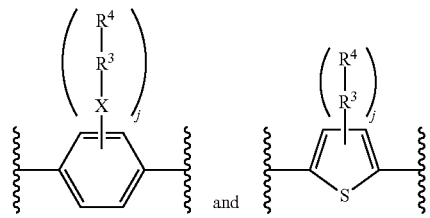

At each occurrence, j is independently chosen from 0, 1, 2, 3, and 4. At each occurrence, X is a bond, —O—, —NH—, or —S—. At each occurrence, $R^3$ is a $(C_1\text{-}C_{20})$hydrocarbylene interrupted by 0, 1, 2, 3, 4, 5, 6, 7, 8, or 9 heteroatoms. At each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ is independently chosen from a substituted or unsubstituted $(C_1\text{-}C_{10})$hydrocarbyl. At each occurrence, Y is independently chosen from a bond and —C≡C—. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and —C≡C—.

In various embodiments, the present invention provides a method of treating a substrate. The method includes contacting the substrate with a conjugated polyelectrolyte including a subunit having the following structure:

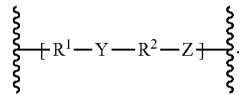

At each occurrence, $R^1$ is independently chosen from:

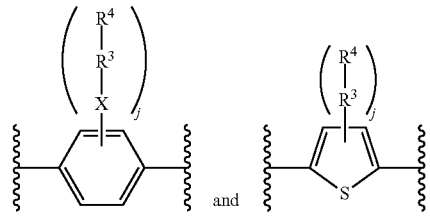

At each occurrence, j is independently chosen from 0, 1, 2, 3, and 4. At each occurrence, X is a bond, —O—, —NH—, or —S—. At each occurrence, $R^3$ is a $(C_1\text{-}C_{20})$hydrocarbylene interrupted by 0, 1, 2, 3, 4, 5, 6, 7, 8, or 9 heteroatoms. At each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ is independently chosen from a substituted or unsubstituted $(C_1\text{-}C_{10})$hydrocarbyl. At each occurrence, Y is independently chosen from a bond and —C≡C—. At each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z is independently chosen from a bond and —C≡C—.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1A:
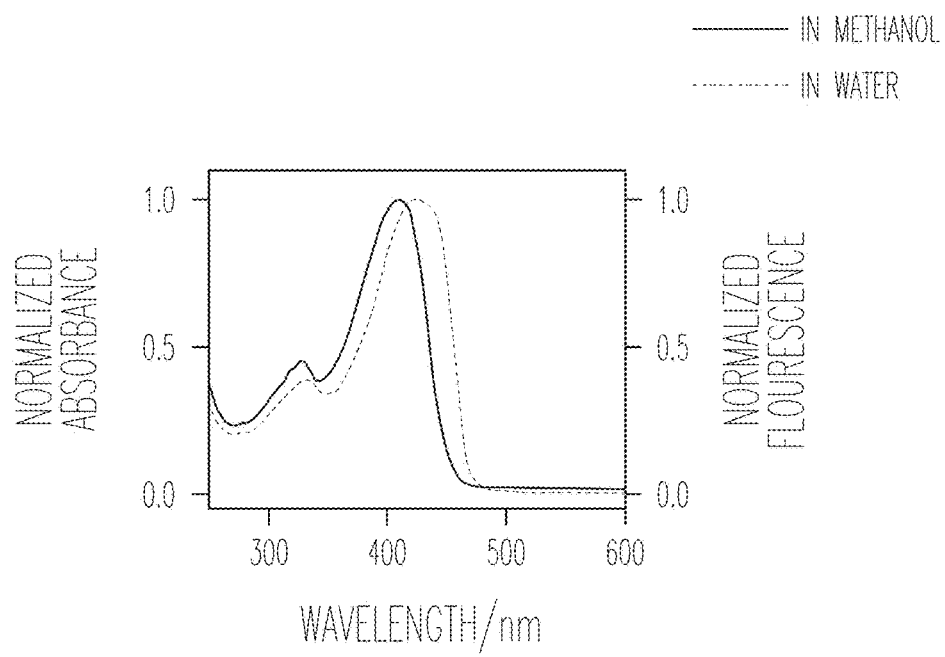
FIGS. 1A-D illustrate (1) normalized absorption (a) and fluorescence (b) of PIM-2 in methanol and in water and (2) normalized absorption (c) and fluorescence (d) of PIM-4 in methanol and in water, in accordance with various embodiments.
Figure 1B:
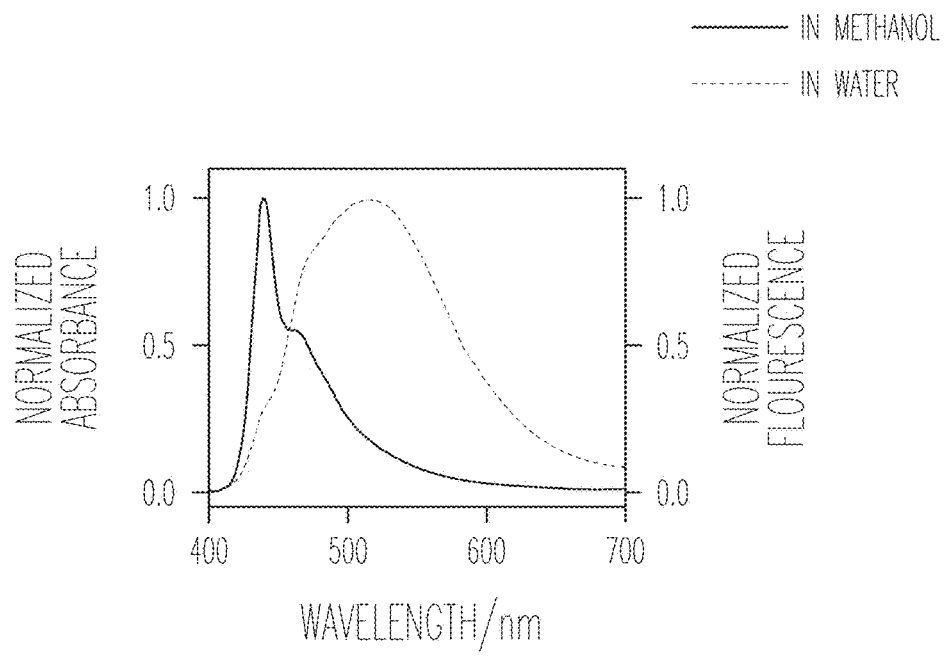
Figure 1C:
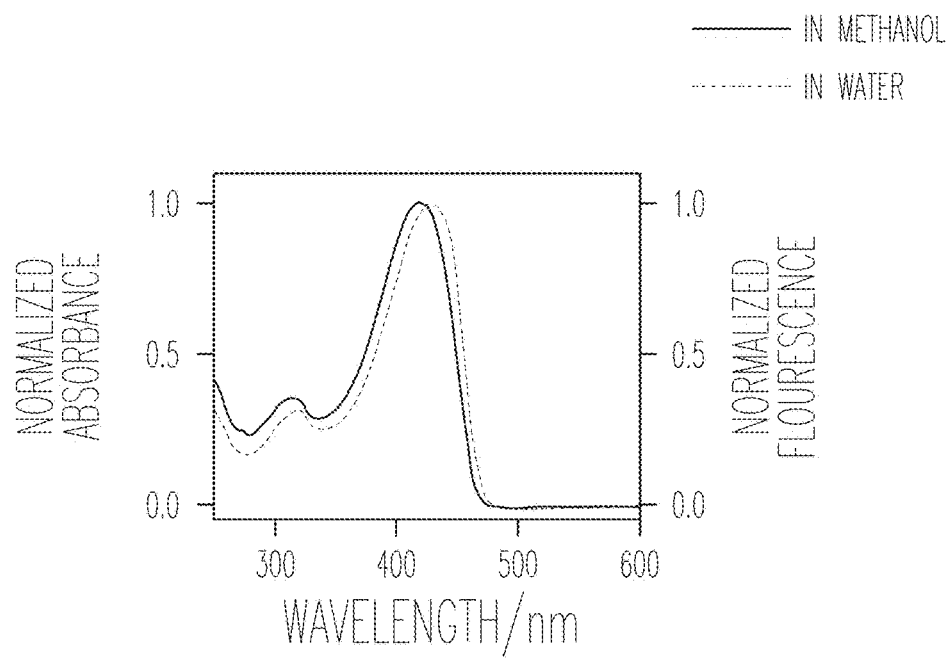
Figure 1D:
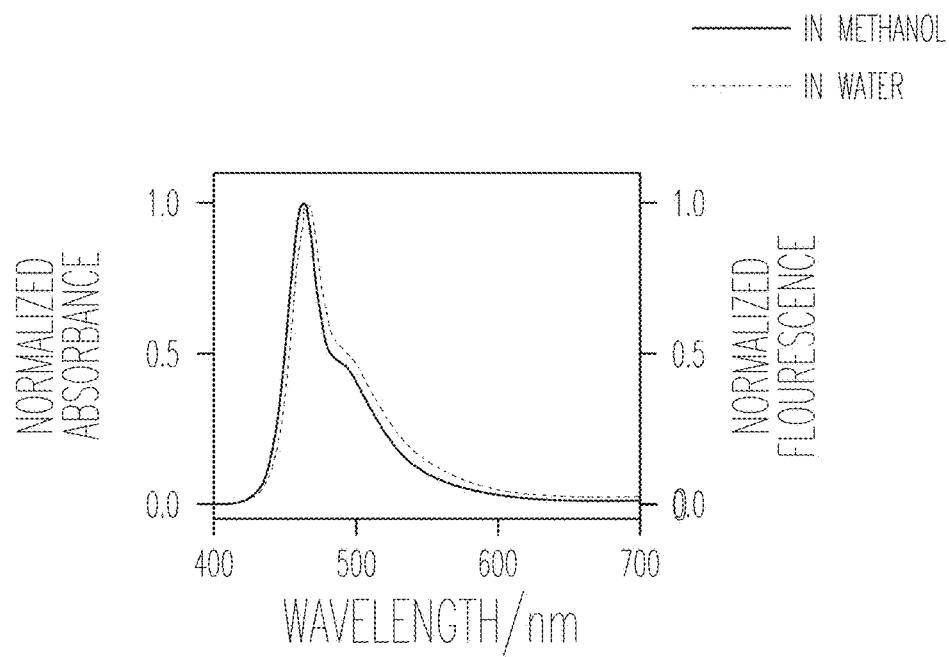

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999%/o or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a\text{-}C_b)$hydrocarbyl, wherein a and b are integers and mean having any of a to b number of carbon atoms. For example, $(C_1\text{-}C_4)$hydrocarbyl means the hydrocarbyl group can be methyl ($C_1$), ethyl ($C_2$), propyl ($C_3$), or butyl ($C_4$), and $(C_0\text{-}C_b)$hydrocarbyl means in certain embodiments there is no hydrocarbyl group.

The term "number-average molecular weight" ($M_n$) as used herein refers to the ordinary arithmetic mean of the molecular weight of individual molecules in a sample. It is defined as the total weight of all molecules in a sample divided by the total number of molecules in the sample. Experimentally, $M_n$ is determined by analyzing a sample divided into molecular weight fractions of species i having $n_i$ molecules of molecular weight $M_i$ through the formula $M_n = \Sigma M_i n_i / \Sigma n_i$. The $M_n$ can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "oligomer" as used herein refers to a molecule having an intermediate relative molecular mass, the structure of which essentially includes a small plurality of units derived, actually or conceptually, from molecules of lower relative molecular mass. A molecule having an intermediate relative mass can be a molecule that has properties that vary with the removal of one or a few of the units. The variation in the properties that results from the removal of the one of more units can be a significant variation.

The term "solvent" as used herein refers to a liquid that can dissolve a solid, liquid, or gas. Non-limiting examples of solvents are silicones, organic compounds, water, alcohols, ionic liquids, and supercritical fluids.

Herein, when it is designated that a variable in the structure can be "a bond," the variable can represent a direct bond between the two groups shown as linked to that variable, such as a single bond.

As used herein, the term "polymer" refers to a molecule having at least one repeating unit and can include copolymers.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

The polymers described herein can terminate in any suitable way. In some embodiments, the polymers can terminate with an end group that is independently chosen from a suitable polymerization initiator, —H, —OH, a substituted or unsubstituted ($C_1$-$C_{20}$)hydrocarbyl (e.g., ($C_1$-$C_{10}$)alkyl or ($C_6$-$C_{20}$)aryl) interrupted with 0, 1, 2, or 3 groups independently chosen from —O—, substituted or unsubstituted —NH—, and —S—, a poly(substituted or unsubstituted ($C_1$-$C_{20}$)hydrocarbyloxy), and a poly(substituted or unsubstituted ($C_1$-$C_{20}$)hydrocarbylamino).

Conjugated Polyelectrolyte.

In various embodiments, the present invention provides a conjugated polyelectrolyte including a subunit having the following structure:

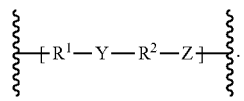

The conjugated electrolyte can be at least one of a small molecule, an oligomer, and a polymer. At each occurrence, $R^1$ can be independently chosen from:

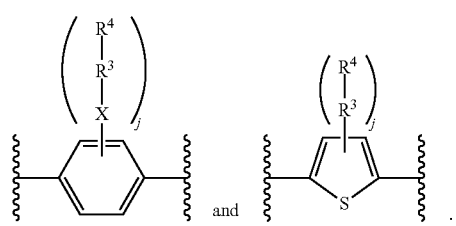

At each occurrence, j can be independently chosen from 0, 1, 2, 3, and 4. At each occurrence, X can be a bond, —O—, —NH—, or —S—. At each occurrence, $R^3$ can be a ($C_1$-$C_{20}$)hydrocarbylene interrupted by 0, 1, 2, 3, 4, 5, 6, 7, 8, or 9 heteroatoms. At each occurrence, $R^4$ can be independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$. At each occurrence, $R^5$ can be independently chosen from a substituted or unsubstituted ($C_1$-$C_{10}$)hydrocarbyl. At each occurrence, Y can be independently chosen from a bond and —C≡C—. At each occurrence, $R^2$ can be independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z can be independently chosen from a bond and —C≡C—.

As used herein, the term "-(1,4-substituted 1,4-diazabicyclo[2.2.2]octane-1,4-diium)-$R^5$" refers to a substituent having the structure:

The conjugated polyelectrolyte can further include one or more charge-balancing counterions. The counterions can be any one or more suitable counterions that can balance charges in the conjugated polyelectrolyte. The counterion can be a halide, such as $Br^-$.

The conjugated polyelectrolyte can be a linear polymer having two termini. The conjugated polyelectrolyte can any suitable terminal groups at the termini. For example, the conjugated polyelectrolyte can include terminal groups T which can each be independently chosen from —H, -L-H, -L-C≡CH, -L-C≡CH, -L-$R^T$, -L-$R^L$-$R^T$, -L-C≡C—$R^T$, -L-C≡C—$R^L$—$R^T$, -L-$R^L$—C≡C—$R^L$—$R^T$, and -L-C≡C—$R^L$—C≡C—$R^L$—$R^T$. At each occurrence, $R^T$ can be independently chosen from —H, —Br, —($C_1$-$C_{10}$)alkyl, —C(O)—OH, —C(O)—O(($C_1$-$C_{10}$)alkyl), —($C_1$-$C_{10}$)alkylene-N(($C_1$-$C_{10}$)alkyl)$_3^+X^-$, —O—($C_1$-$C_{10}$)alkylene-N(($C_1$-$C_{10}$)alkyl)$_3^+X^-$, wherein $X^-$ is a counterion. At each occurrence, $R^L$ can be independently chosen from a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, naphthylene, and -(1,4-substituted 1,4-diazabicyclo[2.2.2]octane-1,4-diium)-. At each occurrence, L can be independently chosen from a bond, —($C_1$-$C_{10}$)alkylene-, and —O—($C_1$-$C_{10}$)alkylene-.

The subunit —[$R^1$—Y—$R^2$—Z]— can occur any suitable number of times in the conjugated electrolyte. In some embodiments, the subunit —[$R^1$—Y—$R^2$—Z]— occurs once in the conjugated electrolyte. In some embodiments, the subunit —[$R^1$—Y—$R^2$—Z]— occurs more than once in the conjugated electrolyte and is a repeating unit. The subunit can be the only subunit or repeating unit in a conjugated polyelectrolyte, or the conjugated polyelectrolyte can include other subunits or repeating units. In some embodiments, the conjugated polyelectrolyte includes the structure:

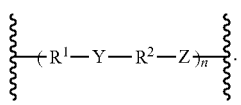

The variable n can be about 1 to about 10,000, or about 1, or less than, equal to, or greater than about 2, 3, 4, 5, 6, 7, 8, 9, 10, 12, 14, 16, 18, 20, 25, 30, 35, 40, 45, 50, 75, 100, 125, 150, 175, 200, 250, 500, 750, 1,000, 1,500, 2,000, 2,500, 5,000, 7,500, or about 10,000 or more. In some embodiments, the conjugated polyelectrolyte has the structure:

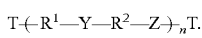

In some embodiments, j can be 1 or 2. At each occurrence, $R^1$ can be independently chosen from:

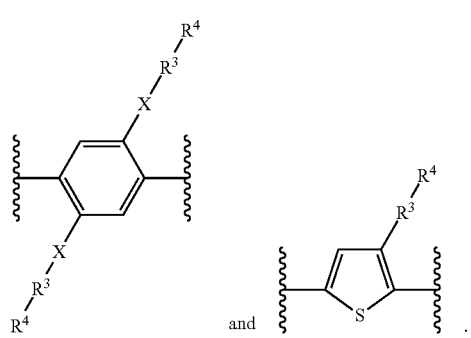

The variable $R^4$ can be an imidazole substituted at the 3-position by $R^5$. The variable $R^4$ can have the structure:

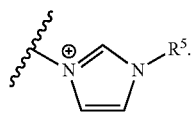

The variable $R^5$ can be methyl. Herein it is to be understood that imidazolium shares the positive charge between the two nitrogen atoms via resonance, and the imidazolium can be represented as having the charge on either nitrogen atom. The variable $R^4$ can have a 3-methylimidazolium structure:

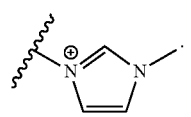

The variable $R^1$ can have the structure:

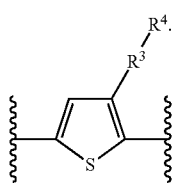

At each occurrence, $R^3$ can be independently chosen from a $(C_1\text{-}C_{10})$alkylene. At each occurrence, $R^4$ can be independently chosen from -(1,4-substituted 1,4-diazabicyclo[2.2.2]octane-1,4-diium)-$R^5$, 3-$R^5$-substituted-imidazolium, pyridinium, and $-N^+(R^5)_3$. The variable $R^4$ can be independently chosen from -(1,4-substituted 1,4-diazabicyclo[2.2.2]octane-1,4-diium)-$(C_1\text{-}C_{10})$alkyl, 3-methylimidazolium, pyridinium, and $-N^+((C_1\text{-}C_5)\text{alkyl})_3$. At each occurrence, $R^5$ can be independently chosen from $(C_1\text{-}C_{10})$alkyl. At each occurrence, Y can be a bond. At each occurrence, $R^2$ can be independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z can be a bond. The variables Y, $R^2$, and Z can be a bond.

The variable $R^1$ can have the structure:

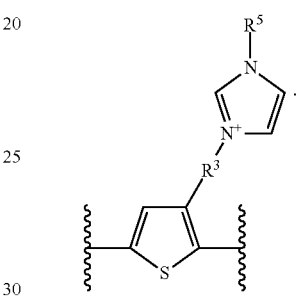

At each occurrence, $R^3$ can be independently chosen from a $(C_1\text{-}C_{20})$hydrocarbylene interrupted by 0, 1, 2, 3, 4, 5, 6, 7, 8, or 9 heteroatoms. At each occurrence, $R^3$ can be a $(C_1\text{-}C_{10})$alkylene interrupted by 0, 1, 2, 3, or 4 oxygen atoms. At each occurrence, $R^5$ can be independently chosen from a substituted or unsubstituted $(C_1\text{-}C_{10})$hydrocarbyl. At each occurrence, $R^5$ can be independently chosen from a $(C_1\text{-}C_5)$alkyl. At each occurrence, Y can be a bond. At each occurrence, $R^2$ can be independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, $R^2$ can be a bond. At each occurrence, Z can be a bond. The conjugated polyelectrolyte can include the following structure:

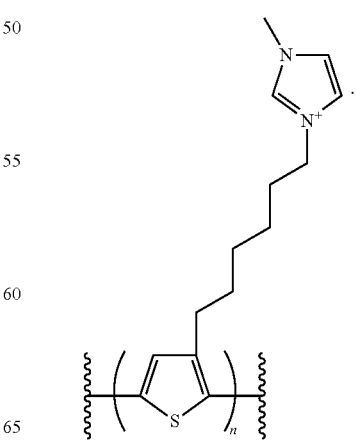

The variable n can be about 1 to about 10,000.

In some embodiments, at each occurrence, X can be —O—. At each occurrence, $R^3$ can be a $(C_2-C_4)$alkylene. At each occurrence, Y can be —C≡C—. At each occurrence, $R^2$ can be a bond. At each occurrence, Z can be a bond. At each occurrence, —$R^4$ can be chosen from —$N^+(CH_3)_3$, —$N(CH_3)_2$, —$SO_3^-$,

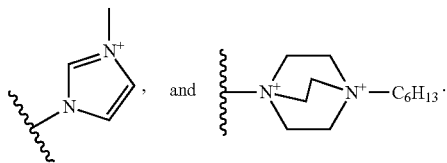

At each occurrence, $R^1$ can have the structure:

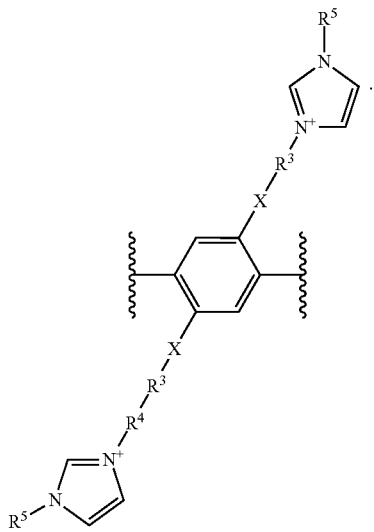

At each occurrence, X can be a bond, —O—, —NH—, or —S—. At each occurrence, $R^3$ can be independently chosen from a $(C_1-C_{20})$hydrocarbylene interrupted by 0, 1, 2, 3, 4, 5, 6, 7, 8, or 9 heteroatoms. At each occurrence, $R^5$ can be independently chosen from a substituted or unsubstituted $(C_1-C_{10})$hydrocarbyl. At each occurrence, Y can be independently chosen from a bond and —C≡C—. At each occurrence, $R^2$ can be independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z can be independently chosen from a bond and —C≡C—.

At each occurrence, X can be —O—. At each occurrence, $R^3$ can be a $(C_1-C_{10})$alkylene interrupted by 0, 1, 2, 3, or 4 oxygen atoms. At each occurrence, $R^5$ can be independently chosen from a $(C_1-C_5)$alkyl. At each occurrence, Y can be —C≡C—. At each occurrence, $R^2$ can be a bond. At each occurrence, Z can be a bond. The conjugated polyelectrolyte can include the following structure:

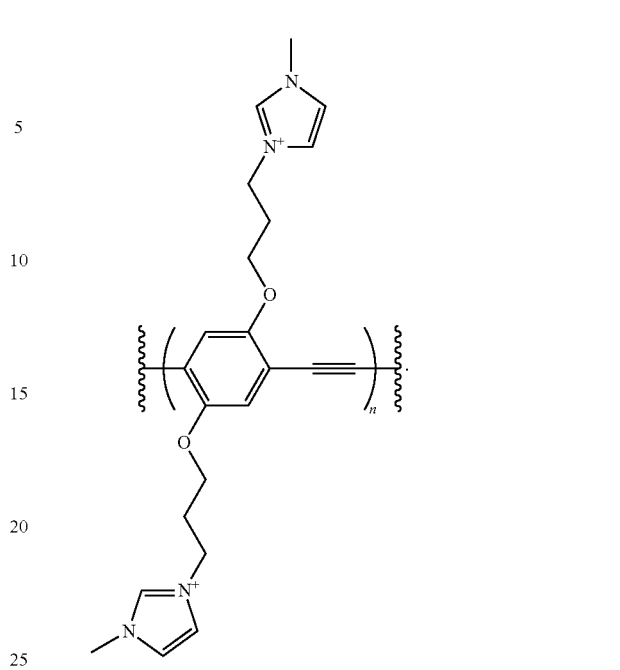

The variable n can be about 1 to 10,000.

At each occurrence, X can be —O—. At each occurrence, $R^3$ can be a $(C_2-C_4)$alkylene. At each occurrence, Y can be —C≡C—. At each occurrence, $R^2$ can be independently chosen from a 1,4-substituted phenylene and a 2,5-substituted thiophenylene. At each occurrence, Z can be a —C≡C—. At each occurrence, $R^4$ can be independently chosen from —$N^+(CH_3)_3$, —$N(CH_3)_2$, —$SO_3^-$,

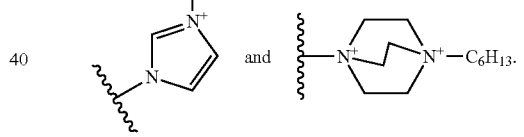

At each occurrence, $R^2$ can be independently chosen from:

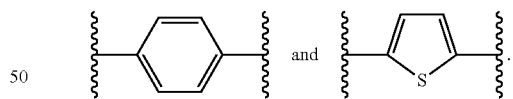

The variable $R^2$ can be

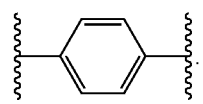

At each occurrence, X can be —O—. At each occurrence, $R^3$ can be a $(C_1-C_{10})$alkylene interrupted by 0, 1, 2, 3, or 4 oxygen atoms. At each occurrence, $R^5$ can be independently $(C_1-C_5)$alkyl. At each occurrence, Y can be —C≡C—. At each occurrence, $R^2$ can be a phenylene. At each occurrence, Z can be a —C≡C—. The conjugated polyelectrolyte can include the following structure:

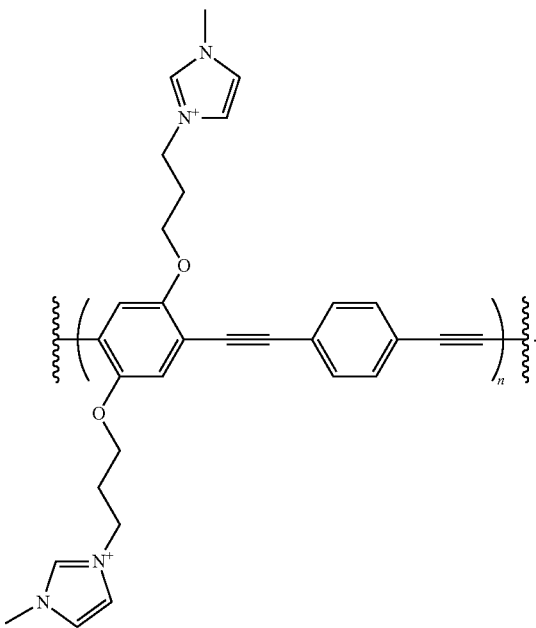

The variable n can be about 1 to about 10,000.
At each occurrence, $R^1$ can have the structure:

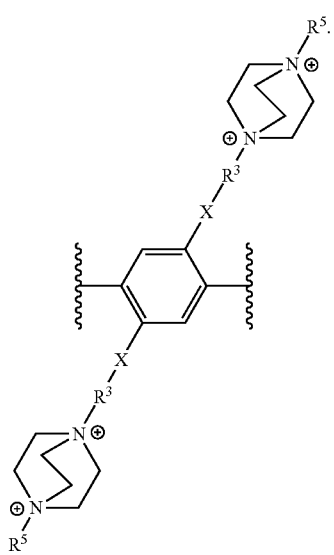

At each occurrence, X can be a bond, —O—, —NH—, or —S—. At each occurrence, $R^3$ can be independently chosen from a $(C_1-C_{20})$hydrocarbylene interrupted by 0, 1, 2, 3, 4, 5, 6, 7, 8, or 9 heteroatoms. At each occurrence, $R^5$ can be independently chosen from a substituted or unsubstituted $(C_1-C_{10})$hydrocarbyl. At each occurrence, Y can be independently chosen from a bond and —C≡C—. At each occurrence, $R^2$ can be independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene. At each occurrence, Z can be independently chosen from a bond and —C≡C—.

At each occurrence, X can be —O—. At each occurrence, $R^3$ can be a $(C_1-C_{10})$alkylene interrupted by 0, 1, 2, 3, or 4 oxygen atoms. At each occurrence, $R^5$ can be independently chosen from a $(C_1-C_5)$alkyl. At each occurrence, Y can be —C≡C—. At each occurrence, $R^2$ can be a phenylene. At each occurrence, Z can be a —C≡C—. The group —X—$R^3$—$R^4$ can have the structure:

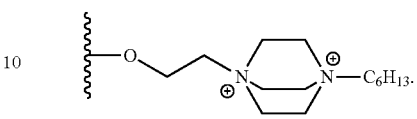

The conjugated polyelectrolyte can include the structure:

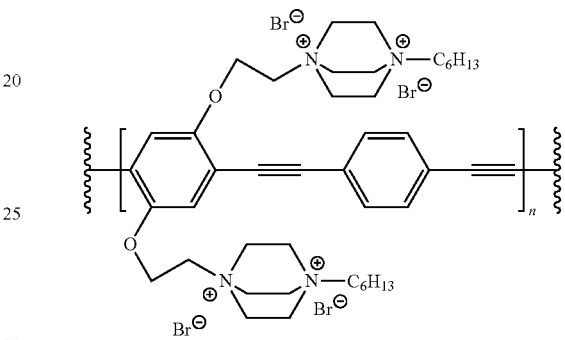

The variable n can be about 1 to about 10,000. The conjugated electrolyte can have the structure:

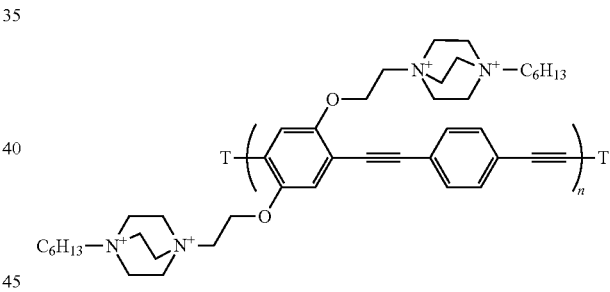

The terminal groups -T can independently be any suitable terminal group described herein, such as —H, -L-H, -L-C≡CH, -L-C≡C—H, -L-$R^T$, -L-$R^L$—$R^T$, -L-C≡C—$R^T$, -L-C≡C—$R^L$—$R^T$, -L-$R^L$—C≡C—$R^L$—$R^T$, and -L-C≡C—$R^L$—C≡C—$R^L$—$R^T$. For example, T can be independently chosen from —H, —Br, —C≡CH, and —$C_6H_5$. The variable n can be about 1 to about 10,000, such as about 1 to about 2000.

The conjugated polyelectrolyte can have the following structure:

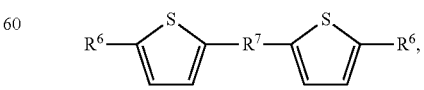

At each occurrence, $R^7$ can be independently chosen from —$(C_1-C_5)$alkyl-$N^+$(($C_1-C_5$)alkyl)$_3$. The variable $R^6$ can be chosen from

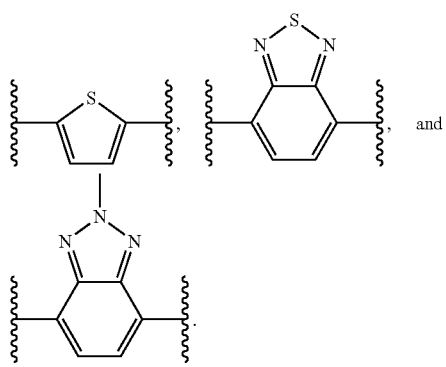

Antimicrobial Substrate

In various embodiments, the present invention provides an antimicrobial substrate. The antimicrobial substrate can include a conjugated polyelectrolyte, such as any one or more conjugated polyelectrolytes described herein. The antimicrobial substrate can also include a substrate.

The substrate can be any suitable substrate that has antimicrobial properties when it includes the conjugated polyelectrolyte. As used herein, the term "antimicrobial" refers to the ability to inhibit growth and/or kill bacterium, for example Gram-positive and Gram-negative bacteria. The substrate can be a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product. The substrate can be a wipe. The substrate can be any suitable substrate where it would be advantageous to have at least one surface having antimicrobial properties.

The conjugated polyelectrolyte can be non-leachably bound to the substrate. In various embodiments, the antimicrobial compound is leachably bound to the substrate. When the antimicrobial compound is non-leachably bound to the substrate, wiping a surface with the antimicrobial substrate can lead to substantially no transfer of the antimicrobial compound to the new surface. In some embodiments, this transfer can be monitored by observing the fluorescence of the antimicrobial compound.

The conjugated polyelectrolyte can be in contact with at least one surface of the substrate. The conjugated polyelectrolyte can be substantially uniformly distributed on the substrate. One or more layers can separate the conjugated polyelectrolyte from the substrate.

The antimicrobial substrate can exhibit antimicrobial properties. For example, the antimicrobial substrate can prevent or inhibit growth of at least one of Gram-positive *Staphylococcus aureus*, Gram-negative *Pseudomonas aeruginosa*, and *Escherichia coli*. The antimicrobial properties of the antimicrobial substrate can exceed the antimicrobial properties of a corresponding substrate without the antimicrobial compound. The antimicrobial substrate can exhibit antimicrobial properties in a non-aqueous environment.

Method of Inactivating a Microorganism.

In various embodiments, the present invention provides a method of inactivating a microorganism. The method can include contacting the microorganism with an effective amount or concentration of a conjugated polyelectrolyte, such as any one or more conjugated polyelectrolytes described herein.

The microorganism can be any microorganism that can be inactivated by one or more conjugated polyelectrolytes described herein. For example, the microorganism can include at least one of a bacterium, virus, fungus, mold, slime mold, algae, and yeast.

The inactivating of the microorganism can be accomplished in a shorter period of time in the presence light as compared to a corresponding method in the absence of light.

Method of Disinfecting an Object.

In various embodiments, the present invention provides a method of disinfecting an object. The method can include contacting the object with an effective amount or concentration of any one or more conjugated polyelectrolytes described herein.

The object can be any suitable object that can be at least partially disinfected by contacting with one or more conjugated polyelectrolytes described herein. The disinfecting of an object can be accomplished in a shorter period of time in the presence of light as compared to a corresponding method in the absence of light.

Method of Treating a Substrate.

In various embodiments, the present invention provides a method of treating a substrate. The method can include contacting the substrate with one or more conjugated polyelectrolytes described herein.

The contacted substrate can have antimicrobial properties. The antimicrobial properties can include prevention of growth of at least one of Gram-positive *Staphylococcus aureus*, Gram-negative *Pseudomonas aeruginosa*, and *Escherichia coli*. The antimicrobial properties of the contacted substrate can exceed the antimicrobial properties of the substrate prior to the contacting. The contacted substrate can have antimicrobial properties in a non-aqueous environment.

The substrate can be any suitable substrate that can exhibit antimicrobial properties after being contacted with the one or more conjugated polyelectrolytes. The substrate can be at least one of a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

The contacting can be performed in any suitable way. The contact can be performed by at least one of foamed applicators, cotton swabs, saturated swab sticks, saturated wipes, aerosols, sprays, brushes, and dips. In various embodiments, the contacting is accomplished by at least on of an aerosol spray and spray. For example, the antimicrobial compound may be mixed with an aerosol propellant (e.g., dichlorodifluoromethane, trichlorofluoromethane, dichlorotetrafluoroethane, carbon dioxide or other suitable gas).

EXAMPLES

Various embodiments of the present invention can be better understood by reference to the following Examples which are offered by way of illustration. The present invention is not limited to the Examples given herein.

Part I.

Example 1.1

Example 1.1.1

Synthesis of PIM-2 and PIM-4

Instrumentation and Methods. NMR spectra were recorded using a Varian VXR-300 FT-NMR, operating at 300 MHz for ¹H NMR and at 75.4 MHz for ¹³C NMR. UV-visible absorption spectra were recorded using a Varian Cary 100 dual beam spectrophotometer with a scan rate of 300 nm/min.
The conjugated polyelectrolytes PIM-2 and PIM-4 were prepared.
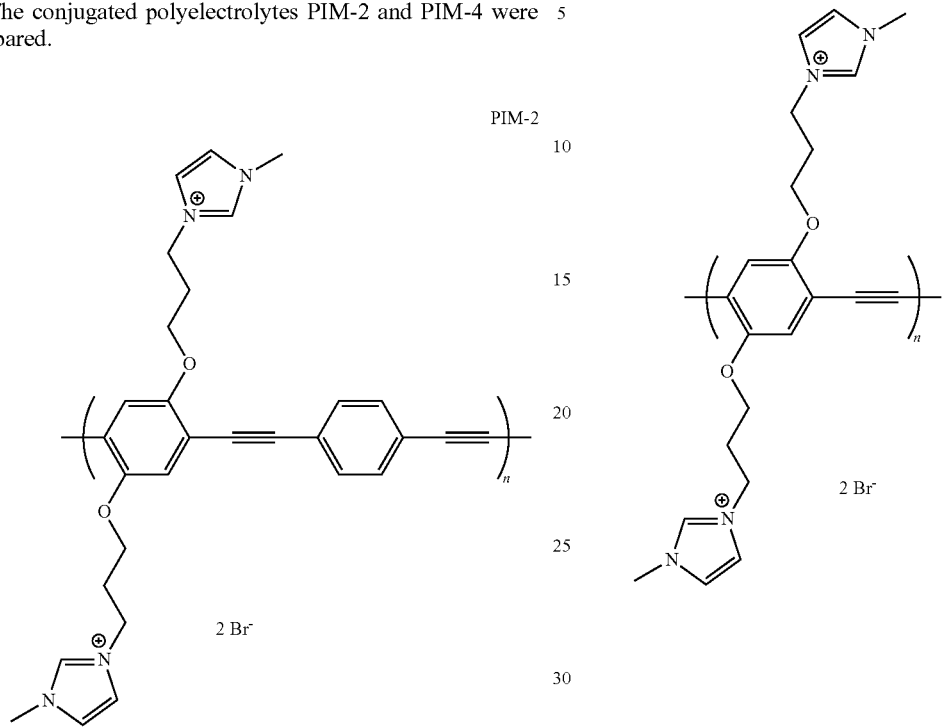
PIM-2 and PIM-4 were prepared according to Scheme 1.
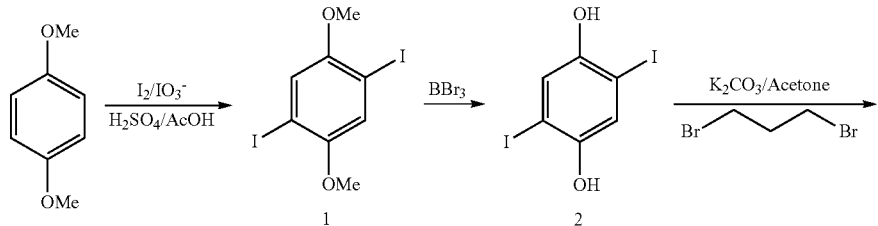
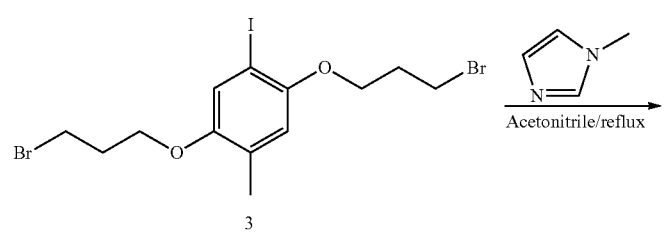

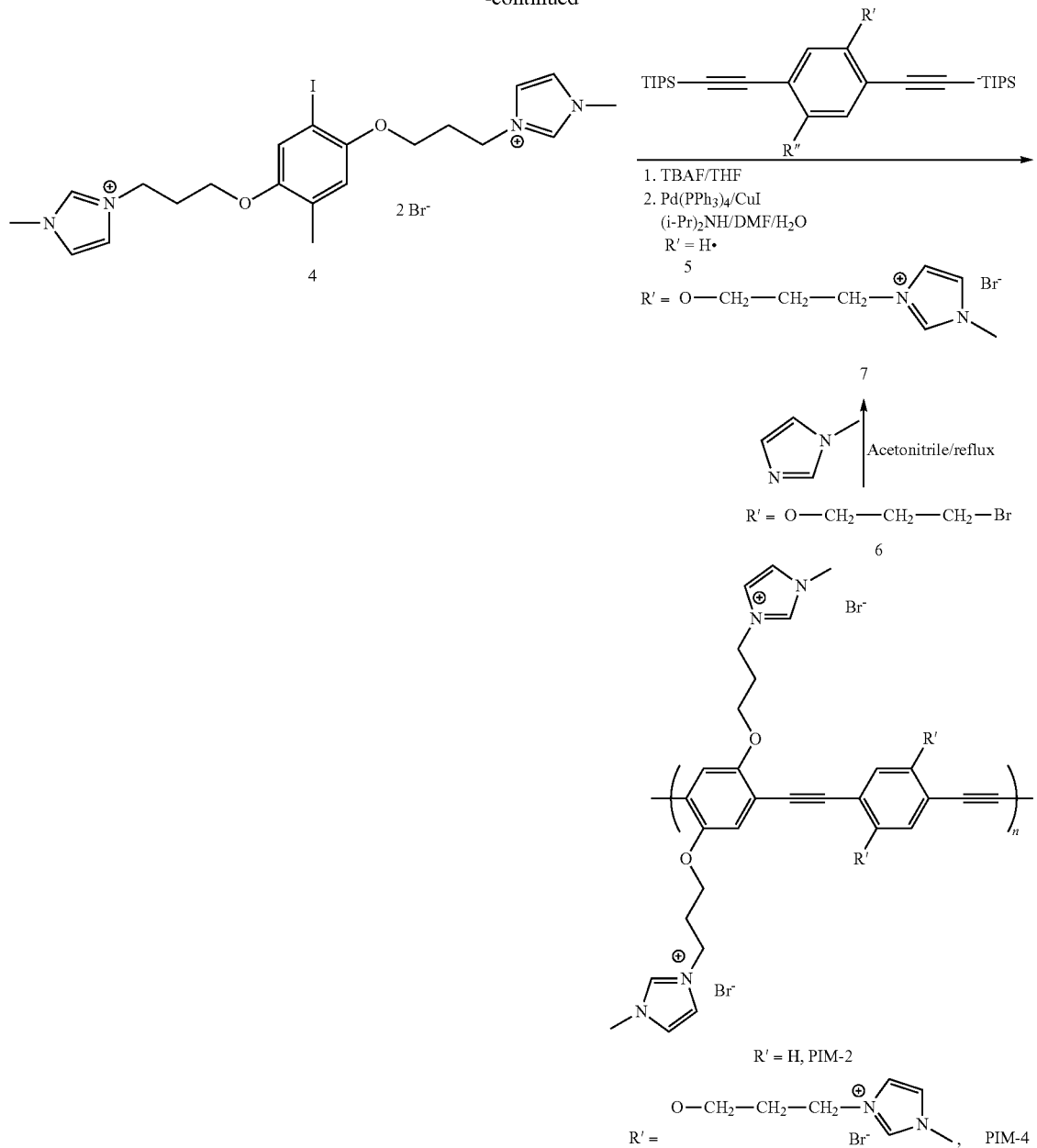

Triethylamine and tetrahydrofuran (THF) were purified by distillation over sodium hydride. Pd(PPh$_3$)$_4$ catalyst was used as received from Stream Chemical Co. Monomers. Compounds 1, 2, 3, 5, and 6 were synthesized following revised procedures reported in the literature. See McQuade, D. T.; Hegedus, A. H.; Swager, T. M. *J. Am. Chem. Soc.* 2000, 122, 12389; see also Ji, E.-K.; Whitten, D. G.; Schanze. K. S. *Langmuir* 2011, 27, 1565. Polymerization was performed under Sonogashira cinditions as described herein in Scheme 1.

Representative polymerization reaction A deoxygenated solution of 8.9 mg (9 μmol) of Pd(PPh3)$_4$ and 2 mg (10 μmol) of CuI in 4 mL of DMF/diisopropylamine (1:1 mixture) was added via cannula to a deoxygenated solution of Monomer 4 (250 mg, 0.32 mmol), monomer 5 (40.2 mg, 0.319 mmol) in 8 mL of DMF/Water mixture in a Schlenk flask. The solution was deoxygenated with argon for 15 min and the resulting mixture was heated to 60° C. and stirred for 16 h. The obtained yellow solution was poured into acetone (100 mL), which induced the polymer to precipitate. The precipitate was collected by vacuum filtration and further purified by two repeated cycles of dissolution in minimum amount of water and precipitation into a large volume of acetone. To the aqueous solution of the polymer, 20 mg of NaCN was added and the final purification was accomplished by dialysis of an aqueous solution of the polymer against deionized water and (Millipore Simplicity water system) using a 6-8 kD MWCO cellulose membrane (Fisher Scientific). After dialysis, the polymer solution was filtered through a 0.45 μm nylon membrane, and the concentration was adjusted to ca. 1.0 mg mL$^{-1}$. The polymer was stored in this format and diluted as appropriate for spectroscopic studies. The typical yield was about 75%. For the synthesis of PIM-4, the TIPS protected monomer (7) in DMF was first deprotected with TBAF before the addition of other reagents.

Compound 4 (e.g., 3,3'-(3,3'-(2,5-diiodo-1,4-phenylene) bis(oxy)bis(propane-3,1-diyl))bis(1-methyl-1H-imidazol-3-ium) (4) was prepared by suspending Compound 3 (500 mg, 0.82 mmol) and 1-methylimidazole (336 mg, 4.1 mmol) in 15 ml acetonitrile. The reaction was refluxed overnight. The solvent was removed and the white solid was recrystallized from ethanol to yield 610 mg of the product. Yield (94%). $^1$H NMR (300 MHz, DMSO-$d_6$): δ 2.26 (m, 4H), 3.99 (s, 6H), 4.01 (t, 4H), 4.31 (t, 4H), 7.30 (s, 2H), 7.65 (m,2H), 7.75 (m,2H), 9.14 (s,2H), $^{13}$C NMR (75 MHz, DMSO-$d_6$): δ 152.7, 137.3, 124.3, 123.2, 122.969, 87.7, 67.5, 47.2, 36.6, 29.8. ESI-MS $[2M]^{2+}$=304.0066 (Expected: 304.0667)

Compound 7 (e.g., 3,3'-(3,3'-(2,5-bis((triisopropylsilyl)ethynyl)-1,4-phenylene)bis(oxy)bis(propane-3,1-diyl))bis(1-methyl-1H-imidazol-3-ium) was prepared as follows. Compound 6 (200 mg, 0.281 mmol) and 1-methylimidazole (114 mg, 1.4 mmol) were suspended in 10 mL acetonitrile and the reaction was refluxed overnight. The solvent was removed and the white solid was triturated with ether to yield 190 mg of the product. Yield (76%). $^1$H NMR (300 MHz, CDCl$_3$): δ 1.12 (s, 42H), 2.48 (t, 4H) 3.95 (s, 6H), 4.05 (t, 4H), 4.61 (t,4H), 6.81 (s, 2H), 7.21 (m,2H), 7.42 (m,2H), 10.5 (s,2H), $^{13}$C NMR (75 MHz, DMSO-$d_6$): δ 154.09, 137.41, 124.49, 122.87, 117.66, 114.04, 103.37, 97.21, 66.23, 46.55, 36.49, 29.87, 19.14, 11.4. ESI-MS $[2M]^{2+}$=358.2447 (Expected: 358.2435).

All of the polymers were prepared from the corresponding monomers following a similar procedure. A representative procedure for the synthesis of cationic imidazolium polymers is as follows. For the synthesis of PIM-4, the TIPS protected monomer (7) in DMF was first deprotected with TBAF before the addition of other reagents. A deoxygenated solution of 8.9 mg (9 μmol) of Pd(PPh3)$_4$ and 2 mg (10 μmol) of CuI in 4 mL of DMF/diisopropylamine (1:1 mixture) was added via cannula to a deoxygenated solution of Monomer 4 (250 mg, 0.32 mmol), monomer 5 (40.2 mg, 0.319 mmol) in 8 mL of DMF/Water mixture in a Schlenk flask. The solution was deoxygenated with argon for 15 min and the resulting mixture was heated to 60° C. and stirred for 16 h. The obtained yellow solution was poured into acetone (100 mL), which induced the polymer to precipitate. The precipitate was collected by vacuum filtration and further purified by two repeated cycles of dissolution in minimum amount of water and precipitation into a large volume of acetone. To the aqueous solution of the polymer, 20 mg of NaCN was added and the final purification was accomplished by dialysis of an aqueous solution of the polymer against deionized water and (Millipore Simplicity water system) using a 6-8 kD MWCO cellulose membrane (Fisher Scientific). After dialysis, the polymer solution was filtered through a 0.45 μm nylon membrane, and the concentration was adjusted to ca. 1.0 mg mL$^{-1}$. The polymer was stored in this format and diluted as appropriate for spectroscopic studies. The typical yield was about 75%.

PIM-2. $^1$H NMR (300 MHz, CD$_3$OD): δ 2.46 (br, 4H), 3.88 (br, 6H), 4.19 (br, 4H), 4.53 (br,4H), 7.21-8.5 (br,12H).

PIM-4. $^1$H NMR (300 MHz, CD$_3$OD): δ 2.43 (br, 4H), 3.90 (br, 6H), 4.22 (br, 4H), 4.53 (br,4H), 7.29-8.55 (8H, aromatic).

The $^1$H signals of the polymers were relatively broad compared to the monomers—presumably resulting from the slow rotational correlation time of the polymer chains due to aggregation.

Example 1.1.2

Absorption and Fluorescence

FIGS. 1A-D illustrate the absorption spectra of PIM-2 and PIM-4 in methanol and water, in accordance with various embodiments of the present invention. In methanol, PIM-2 features a strong fluorescence and a well-defined 0-0 band with $\lambda_{max}$=410 nm along with a well resolved vibrational progression at lower energy that is characteristic of the PPE backbone. This observation indicates that PIM-2 exists in a mostly unaggregated state in methanol. By contrast, when water is used as the medium, PIM-2 exhibits a broad, structureless and red shifted emission. The red shift observed in both absorption and emission spectral bands, along with diminished fluorescence quantum yield in water together indicate the formation of aggregates in aqueous medium. On the contrary, comparison of the absorption and fluorescence spectra of PIM-4 in methanol and in water shows an interesting trend. In methanol, the 0-0 band with $\lambda_{max}$=418 nm is observed to be slightly red shifted relative to PIM-2 in methanol (Table 1). Surprisingly, the emission of PIM-4 in water strongly resembles that of methanol, exhibiting only a slight red shift of 5 nm. In addition, the fluorescence quantum yield of PIM-4 in water is 3-fold higher compared to that of PIM-2 in water. Thus, the aforementioned observations imply that the polymeric chains of PIM-4 exhibit minimal aggregation, and that this polymer forms less π stacked inter-chain aggregates in aqueous medium.

Figure 2A:
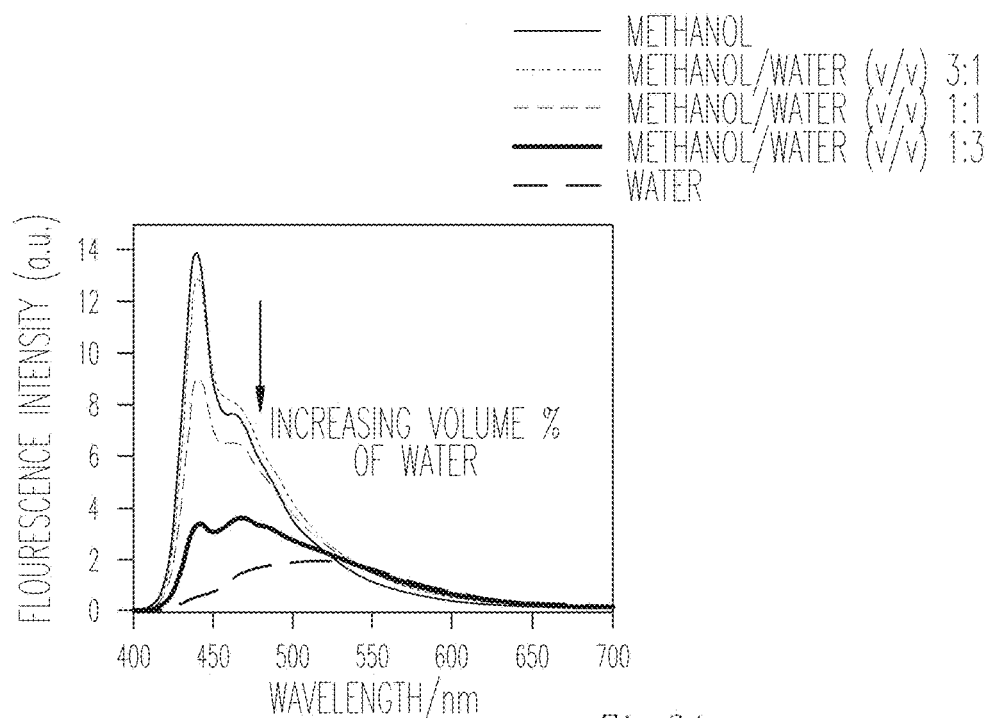
FIGS. 2A-B illustrates the changes in the UV-visible absorption and emission spectra for PIM-2 (A) and PIM-4 (B) in a mixture of methanol and water, in accordance with various embodiments.
Figure 2B:
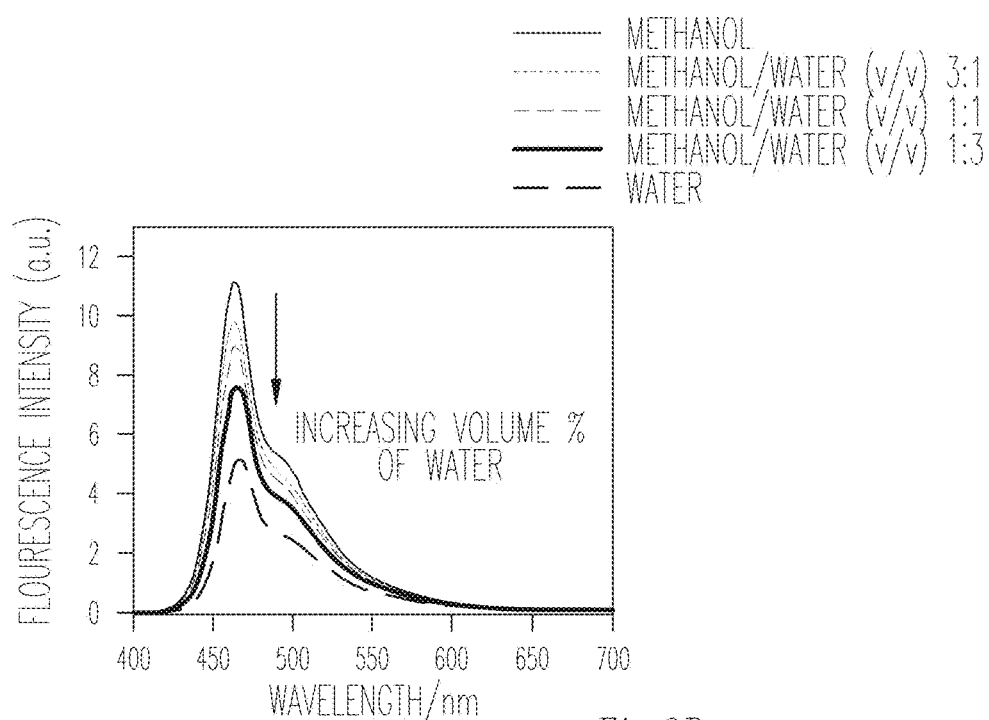

To examine the effect of solvent environment on the optical properties of the PIM polymers, the changes in the UV-visible absorption and emission spectra for each polymer in a mixture of methanol and water was studied by systematically varying the composition of the solvent mixture as illustrated in FIGS. 2A-B, with PIM-2 (A) and PIM-4 (B) in a mixture of methanol and water. As expected, the 0-0 band of PIM-2 in FIG. 2A gradually diminishes with concomitant enhancement of the shoulder band as the volume percentage of water increases in the solvent medium, signaling the formation of CPE aggregates. In contrast, only a slight decrease in emission intensity was observed for PIM-4 in FIG. 2B with increasing water content of the medium; however, the structure of emission spectrum remained the same as the proportion of water increased. These observations collectively indicate that PIM-2 has the tendency to form aggregates, whereas PIM-4 remains mostly in unaggregated form in the aqueous medium. This is consistent with the position that a higher charge density on the side chains will increase the electrostatic repulsion between the polymeric chains resulting in suppression of aggregation driven by the hydrophobic effect. This electrostatic repulsion is relatively low for PIM-2, which consists of an imidazolium moiety on every other phenylene unit—accounting for the aggregate emission observed in water.

Comparison of the fluorescence quantum yield and fluorescence lifetime data of the CPEs in methanol and water are presented in Table 1. In particular, PIM-4 exhibits a higher fluorescence quantum yield in water than PIM-2, which indicates minimal aggregation of PIM-4 in this medium. This characteristic is advantageous, as PPE-based CPEs are known to aggregate in water, resulting in quenching of polymer fluorescence.

TABLE 1

Photophysical data for PIM-2 and PIM-4.

| | $\lambda_{max}^{ab}$ (nm) | $\epsilon_{max}$ (M$^{-1}$cm$^{-1}$) | $\lambda_{max}^{Fl}$ (nm) | $\Phi_{Fl}^{a}$ | $\tau_{fl}$ (ns) |
|---|---|---|---|---|---|
| PIM-2/ MeOH | 410 | 27,900 | 440 | 0.25 ± 0.02 | 0.49 |
| PIM-2/ H$_2$O | 426 | 25,100 | 512 | 0.12 ± 0.02 | 0.21 (20%) 1.1 (31%) 3.6 (49%) |
| PIM-4/ MeOH | 418 | 15,400 | 465 | 0.56 ± 0.03 | 0.59 |
| PIM-4/ H$_2$O | 430 | 14,200 | 466 | 0.34 ± 0.03 | 0.41 (92%) 0.95 (8%) |

[a]Measured using quinine sulfate in 0.1M sulfuric acid ($\Phi_{Fl}$ = 0.54) as actinometer.

Fluorescence quenching. The fluorescence quenching of CPEs by two different cationic quenchers, namely sodium anthraquinone-2,6-disulfonate (AQS) and pyrophosphate (PPi) were studied. In this case, quenching generally results the initial formation of ion-pair complex between CPE and quencher. It is known that AQS quenches the fluorescence of electron rich molecules by a photo-induced electron transfer mechanism. See. e.g., Pinto, M. R.; Tan, C.; Ramey, M. B.; Reynolds, J. R.; Bergstedt, T. S.; Whitten, D. G.; Schanze, K. S. Res. Chem. Intermed. 2007, 33, 79.

Figure 3A:
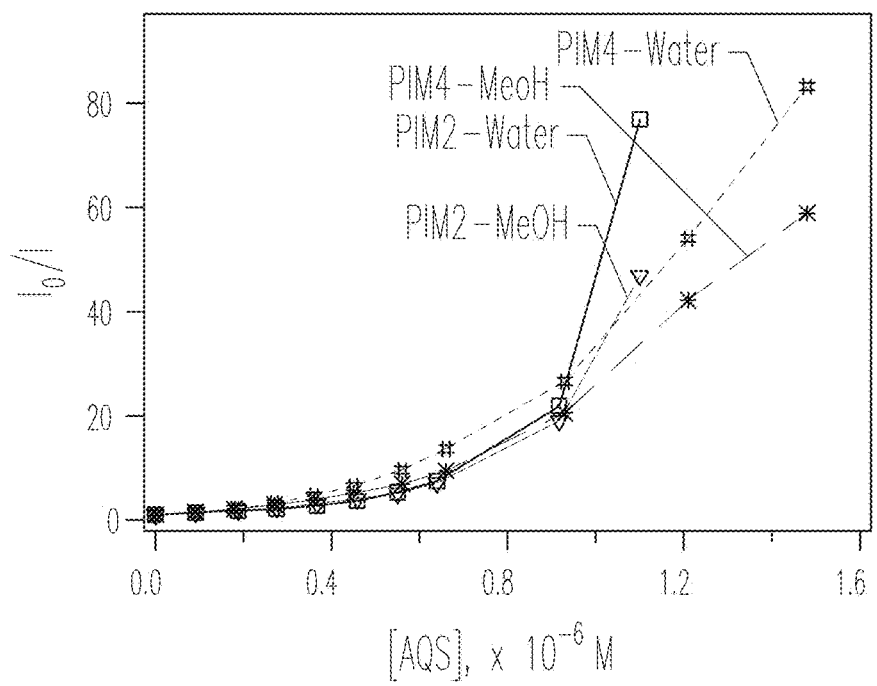
FIGS. 3A-B illustrate Stem-Volmer plots of PIM-2 and PIM-4 with (A) AQS and, (B) PPi as quenchers, (polymer concentration=10 μM in all cases), in accordance with various embodiments.
Figure 3B:
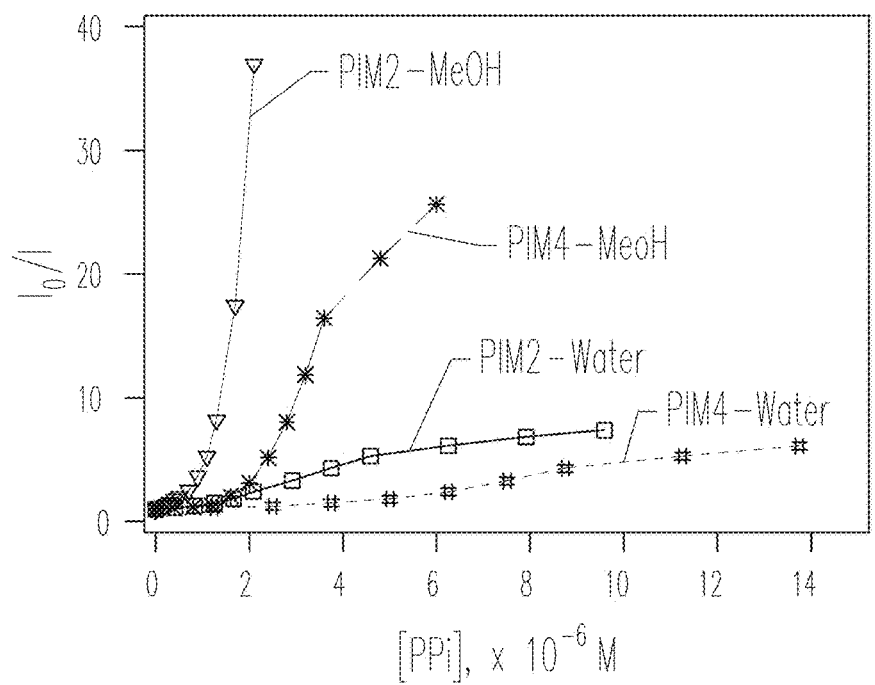

A series of titrations of PIM-2 and PIM-4 with aliquots of AQS or PPi were conducted in both methanol and water to compare the quenching behavior of the polymers in these solvent media. A general trend with increasing quencher concentration is that the absorption spectra of the polymers resulted in a 5-10 nm spectral shift with concomitant band broadening (see supporting information for details). Such spectral characteristics indicate conformational changes in the polymeric structure due to the formation of polymer/quencher complex driven by hydrophobicity. The Stern-Volmer quenching constant for the fluorescence quenching of PIM-2 and PIM-4 by AQS and PPi are summarized in Table 2. Comparison of the $K_{SV}$ of quenching the above CPEs by AQS in methanol and water reveals several clear trends. First, the Stem-Volmer plot is linear at lower quencher concentrations and shows an upward curvature as the concentration of the quencher is increased (FIGS. 3A-B, with (A) AQS and, (B) PPi as quenchers, (polymer concentration=10 µM in all cases)). Secondly, the $K_{SV}$ is on the order of ~10$^6$ M$^{-1}$ in both methanol and water, for both CPEs. These observations clearly indicate the amplified quenching process is in effect. A general trend is that the $K_{SV}$ is higher in water than in methanol for both PIM-2 and PIM-4. Another important point to note is that the homopolymer, PIM-4, shows a higher $K_{SV}$ for AQS in comparison to the copolymer, PIM-2, in both methanol and water; this is quite likely due to the increase in charge density in the case of PIM-4 due to the presence of the pendant imidazolium group on every phenylene unit.

TABLE 2

Stern-Volmer constants for the fluorescence quenching of PIM-2 and PIM-4 by AQS and PPi. $K_{SV}$ was calculated at low concentrations (<0.4 µM for AQS, and <2 µM for PPi) of the quencher where the plot was linear.

| | PIM-2 | | PIM-4 | |
|---|---|---|---|---|
| | $K_{SV}$ (M$^{-1}$) (Methanol) | $K_{SV}$ (M$^{-1}$) (Water) | $K_{SV}$ (M$^{-1}$) (Methanol) | $K_{SV}$ (M$^{-1}$) (Water) |
| AQS | 3.8 × 10$^6$ | 4.5 × 10$^6$ | 7.7 × 10$^6$ | 9.8 × 10$^6$ |
| PPi | 1.6 × 10$^6$ | 3.1 × 10$^5$ | 2.7 × 10$^5$ | 1.3 × 10$^5$ |

Another quencher that was employed in the study was pyrophosphate (PPi). PPi is an important biomolecule formed by the hydrolysis of ATP to AMP, and it is a potent mineralization inhibitor with a strong affinity to Cu$^{2+}$. Table 2 indicates that the Stem-Volmer quenching constants obtained by employing PPi as quencher are remarkably lower than the values obtained by AQS for PIM-2 and PIM-4 in both methanol and water (approximately an order of magnitude lower, with the exception of PIM-2 in methanol).

These results clearly suggest the rapid diffusion of singlet exciton over the CPE backbone during the quenching process with AQS, and a relatively slow quenching effect when PPi is employed as quencher. However, the trend observed with AQS clearly differs from PPi in that higher $K_{SV}$ values were observed when the medium was changed from methanol to water; on the other hand, the opposite trend is observed with PPi. This disparity in quenching rates could be explained by taking a closer look at the mechanism of quenching in the abovementioned cases. The rate of electron transfer with AQS as quencher is expected to be higher with the formation of π-stacked aggregates of polymer chains in aqueous medium, which in turn would enhance exiton transport efficiency. On the other hand, PPi, which presumably has a weaker association with the imidazolium side chains in the aqueous medium, would be less efficient quencher in this medium.

Figure 4A:
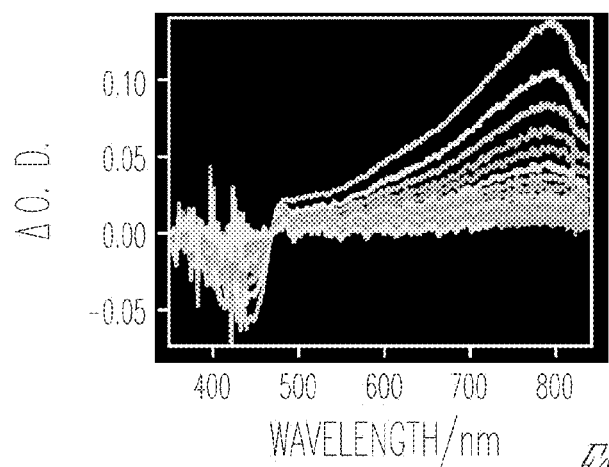
FIG. 4A illustrates the transient absorption difference spectra of PIM-4 (OD~0.7 at 355 nm and excited with the laser energy of ~7 mJ) in water (initial delay=65 ns, subsequent delay increment=6.5 μs, triplet lifetime=28.6 μs), in accordance with various embodiments.
Figure 4B:
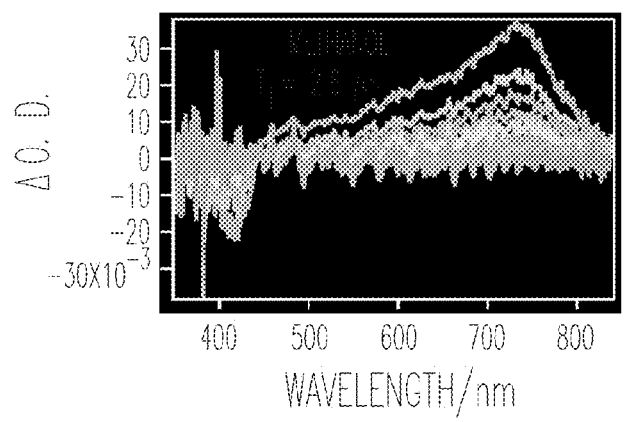
FIG. 4B illustrates the Transient absorption difference spectra of PIM-2 (OD~0.7 at 355 nm and excited with the laser energy of ~7 mJ) in methanol (initial delay=65 ns, subsequent delay increment=1 μs), in accordance with various embodiments.
Figure 4C:
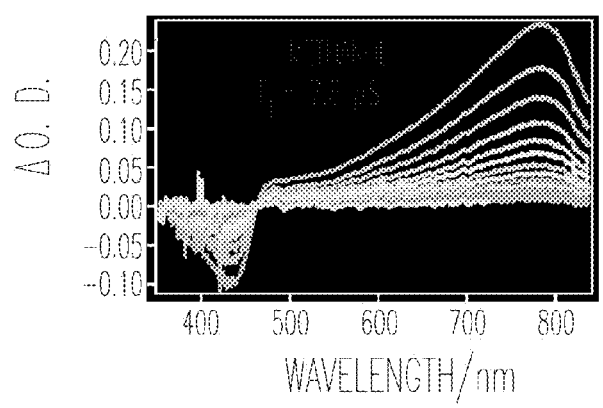
FIG. 4C illustrates the transient absorption difference spectra of PIM-4 (OD~0.7 at 355 nm and excited with the laser energy of ~7 mJ) in methanol (initial delay=65 ns, subsequent delay increment=1 μs), in accordance with various embodiments.

Transient Absorption and Singlet Oxygen Sensitization. It has been well established that the ability of CPEs to sensitize the formation of singlet oxygen has a major role to play in the biocidal process. See e.g., Kilger, R.; Maier, M.; Szeimies, R. M.; Baumler, W. Chem. Phys. Lett. 2001, 343, 543; Maisch, T.; Baier, J.; Franz, B.; Maier, M.; Landthaler, M.; Szeimies, R.-M.; Baumler, W. Proc. Natl. Acad Sci. U.S.A. 2007, 104, 7223: Hill, E. H.; Stratton, K.; Whitten, D. G.; Evans, D. G. Langmuir 2012, 28, 14849; and Corbitt, T. S.; Ding, L.; Ji, E.; Ista, L. K.; Ogawa, K.; Lopez, G. P.; Schanze, K. S.; Whitten, D. G. Photochem. Photobiol. Sci. 2009, 8, 998. Since the triplet excited state of CPEs plays a crucial role in their generation of singlet oxygen, which is mainly responsible for light-activated biocidal activity, the triplet-triplet absorption of the above polymers in methanol and water was examined (e.g. FIGS. 4A, 4B, and 4C) using transient absorption spectroscopy. FIG. 4A illustrates the transient absorption difference spectra of PIM-4 (OD~0.7 at 355 nm and excited with the laser energy of ~7 mJ) in water (initial delay=65 ns, subsequent delay increment=6.5 µs, triplet lifetime=28.6 µs). FIG. 4B illustrates the Transient absorption difference spectra of PIM-2 (OD~0.7 at 355 nm and excited with the laser energy of ~7 mJ) in methanol (initial delay=65 ns, subsequent delay increment=1 µs). FIG. 4C illustrates the transient absorption difference spectra of PIM-4 (OD~0.7 at 355 nm and excited with the laser energy of ~7 mJ) in methanol (initial delay=65 ns, subsequent delay increment=1 µs). Consistent with previous reports concerning CPEs, a broad transient absorption extending in the infrared region, with lifetimes between 1-4 µs, was observed for both PIM-2 and PIM-4; in addition, the transient absorption is efficiently quenched by O$_2$, suggesting the triplet excited state. See e.g., Ji, E.; Corbitt, T. S.; Parthasarathy, A.; Schanze, K. S.; Whitten, D. G. ACS Appl. Mater. Interfaces 2011, 3, 2820. The ability of both polymers to sensitize the formation of singlet oxygen was also confirmed spectroscopically by monitoring singlet oxygen phosphorescence ~1270 nm in deuterated methanol. As anticipated, PIM-4 is more efficient in sensitizing the formation of singlet oxygen ($\Phi_A$=0.13±0.02) in comparison to PIM-2 ($\Phi_A$=0.08±0.02) (2'-acetonaphthone ($\Phi_A$=0.79±0.02) as standard).

In general, as CPEs tend to aggregate in water, it is challenging to observe their transient absorption in the aqueous medium. Unexpectedly, PIM-4 showed transient absorption in water with intensity comparable to methanol (e.g., FIG. 4C), emphasizing that PIM-4 is not aggregated in aqueous medium; however, only a weak signal was observed for PIM-2 in water. This clearly illustrates that PIM-4 has higher and comparable triplet yields in methanol and water respectively; in other words, PIM-4 is likely to sensitize singlet oxygen in aqueous medium with the efficiency similar to methanol. This is advantageous as the biocidal studies are conducted in aqueous medium.

Example 1.1.3

Biocidal Testing

Figure 5:
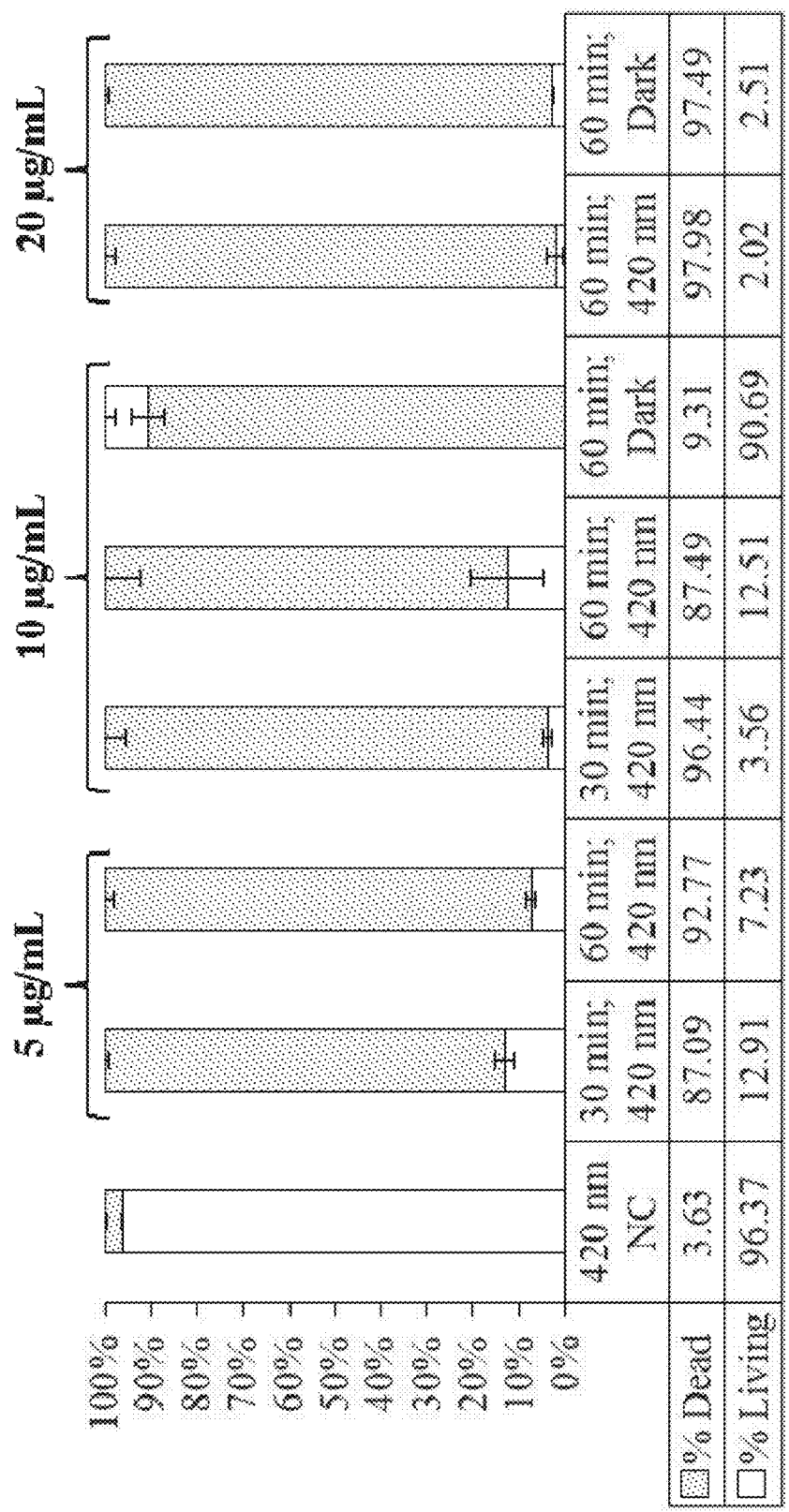
FIG. 5 illustrates E. coli viability against PIM-2 upon exposure to visible light for various time intervals, in accordance with various embodiments.
Figure 6:
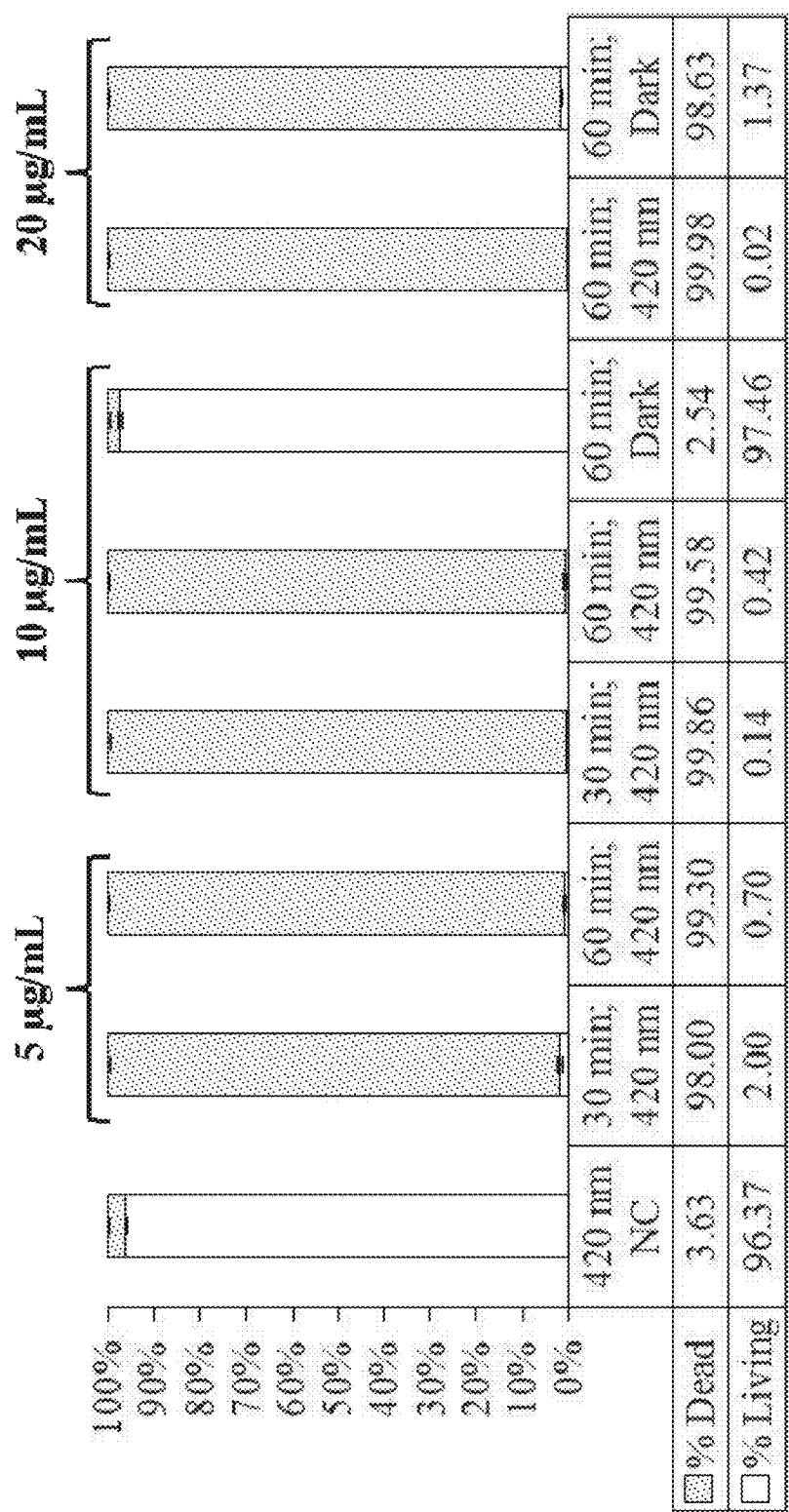
FIG. 6 illustrates E. coli viability against PIM-4 upon exposure to visible light for various time intervals, in accordance with various embodiments.

Biocidal testing was carried out using flow cytometry, confocal fluorescence microscopy, and standard plating techniques. The biocidal activity of both PIM-2 and PIM-4 is high in the presence of blue-violet light ($\lambda$=420 nm). FIG. 5 and FIG. 6 illustrate the biocidal activity of PIM-2 and PIM-4, respectively, against Gram-negative *E. coli*. In FIG. 5 and FIG. 6. NC refers to the negative control, which did not contain biocidal polymer and red indicates % dead and green indicates % alive, as assessed by flow cytometry. At a concentration of just 5 µg/mL, PIM-2 is able to kill approximately 90% of *E. coli* in the presence of near-visible light. In the dark, however, a higher concentration of 20 µg/mL is required to exceed 90% killing. PIM-4 was found to induce 2-log killing of the *E. coli* in numerous samples, and even exceeding 3-log killing at high concentrations in the light.

Figure 7:
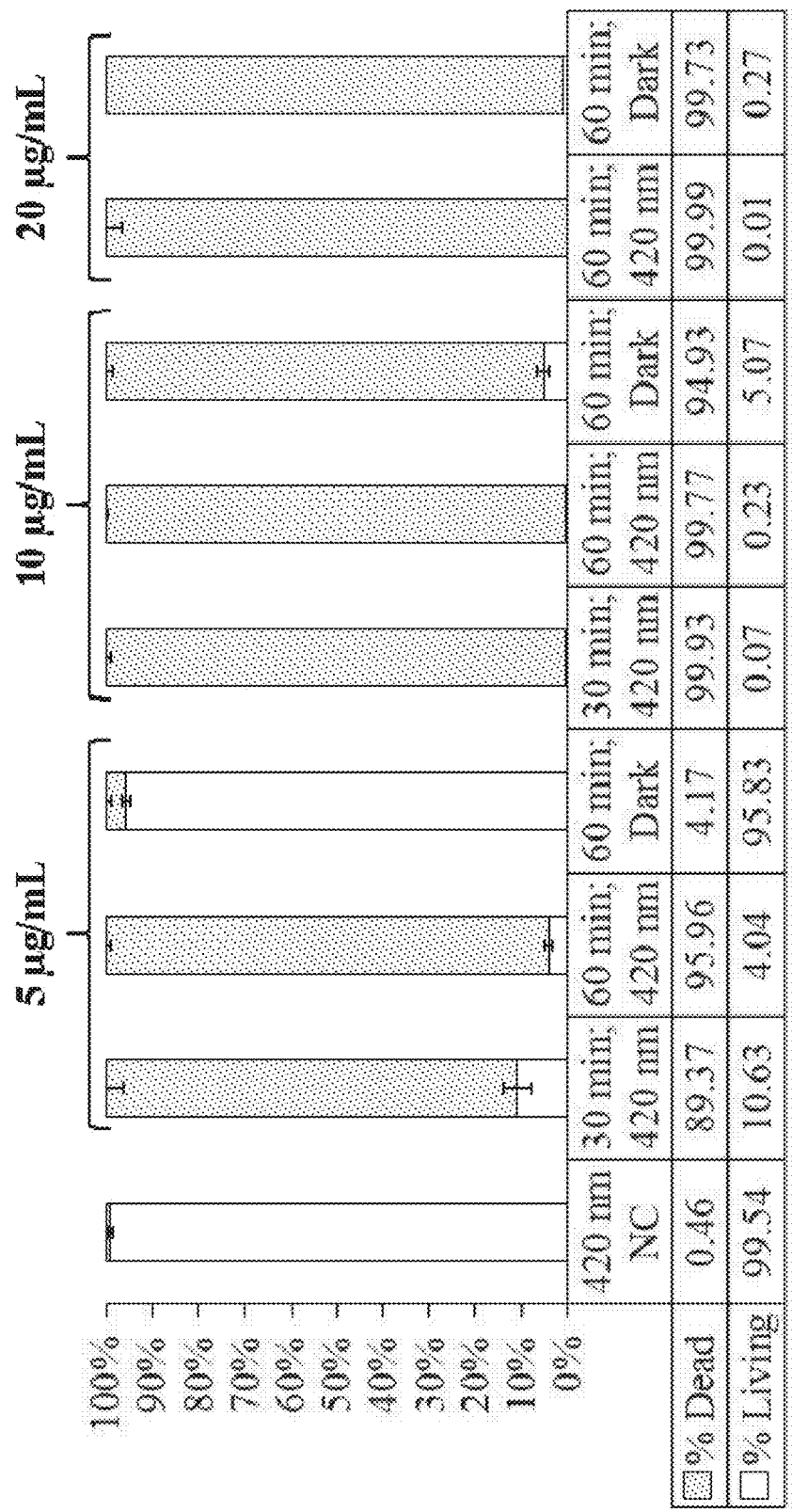
FIG. 7 illustrates S. aureus viability against PIM-2 upon exposure to visible light for various time intervals, in accordance with various embodiments.
Figure 8:
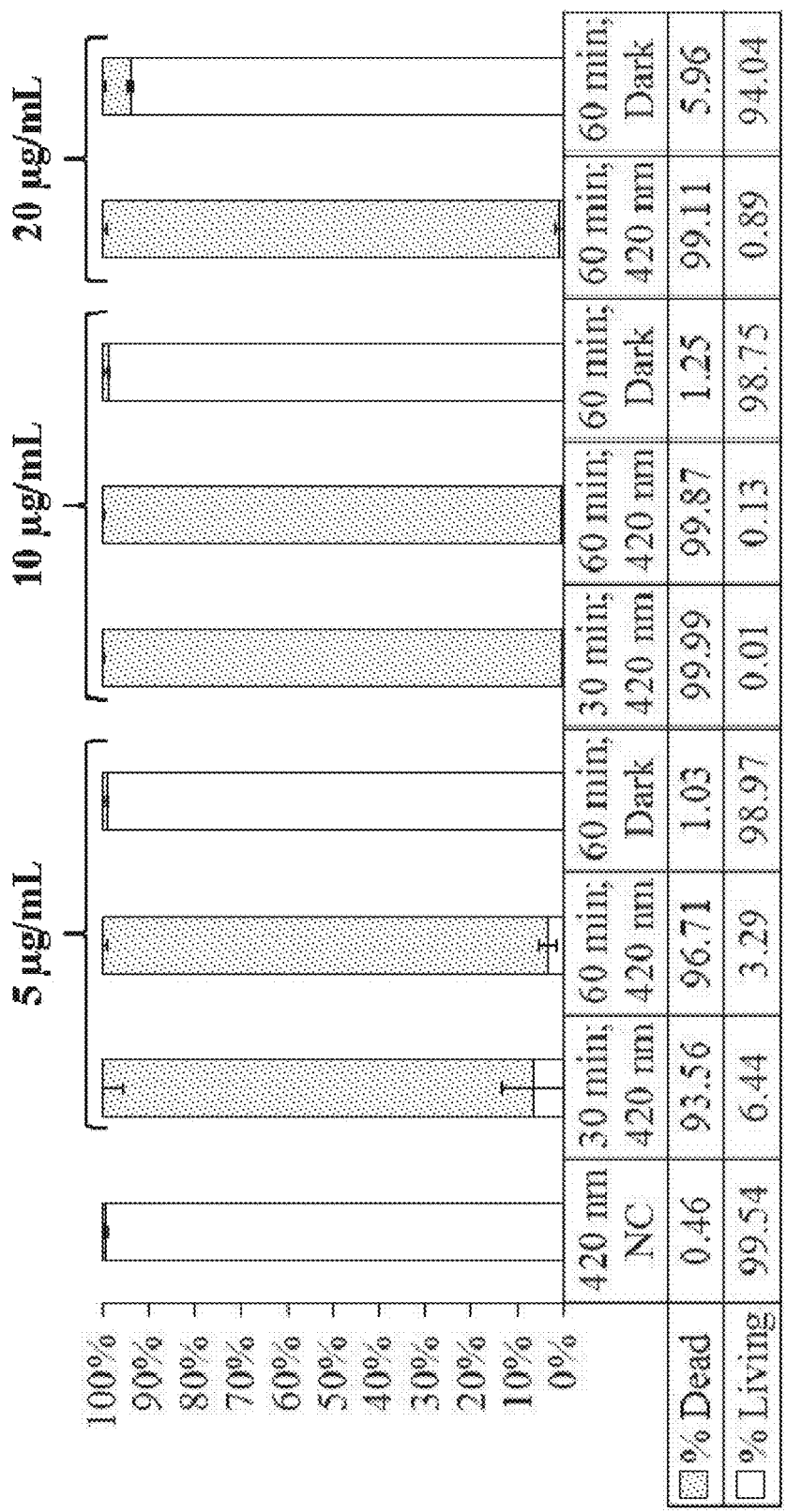
FIG. 8 illustrates S. aureus viability against PIM-4 upon exposure to visible light for various time intervals, in accordance with various embodiments.

Comparison of the efficacy of the two polymers suggests PIM-4 can have better light-activated killing than PIM-2, particularly against *E. coli*. As can be seen FIG. 6, there is 99.30% killing of *E. coli* by PIM-4 after an hour in the light despite the low concentration of 5 µg/mL. PIM-2 achieves 92.77% killing in the same conditions. Even when the concentration is raised to 10 µg-mL, PIM-2 achieves around 90% killing of *E. coli* after an hour of 420 nm irradiation while PIM-4 reaches 99.9% after only 30 min. The difference between the killing effectiveness of PIM-2 and PIM-4 is less apparent with the Gram-positive *S. aureus*. As seen in FIG. 7 and FIG. 8, both polymers achieve ~96% killing after 1 h of 420 nm irradiation. In both FIG. 7 and FIG. 8, NC refers to the Negative Control, which did not contain biocidal polymer. When the concentration is increased to 10 µg/mL, both polymers exceed 3-logs of killing with only 30 min of irradiation. Both PIM-2 and PIM-4 appear to be very effective against Gram positive *S. aureus* in the light. While PIM-2 is able to kill in the dark at elevated concentrations.

The biocidal activity of both polymers in the light is high when compared to other CPEs based on the p-phenylene ethynylene backbone. To test the efficacy of PIM-2 and PIM-4, their biocidal activity was compared to a cationic CPE with DABCO functionalized side chains (PPE-DABCO) that has been recently studied against *E. coli*. See Corbitt, T. S.; Ding, L.; Ji, E.; Ista, L. K.; Ogawa, K.; Lopez, G. P.; Schanze, K. S.; Whitten, D. G. *Photochem. Photobiol. Sci.* 2009, 8, 998. Results showed that the biocidal activity of PPE-DABCO is only 43% at 5 µg/mL and 63% at 10 µg/mL after 1 h of 420 nm irradiation. Results indicate that the imidazolium functionality infers a greater biocidal capability than the DABCO moiety. The efficient light-activated bacterial killing of PIM polymers against both Gram-negative and Gram-positive strains at low concentrations shows the potential of imidazolium functionalized PPEs as effective biocides.

Example 1.2

Example 1.2.1

Synthesis of P3HT-imidazolium

P3HT was prepared according to Scheme 2. Scheme 2 includes the synthesis of regioregular poly[3-(6-bromhexyl) thiophene (P3HT-Br) via the GRIM method. See Zhai, L.; Pilston, R. L.; Zaiger, K. L.; Stokes, K. K.; McCullough, R. D. *Macromolecules* 2003 36, 61.

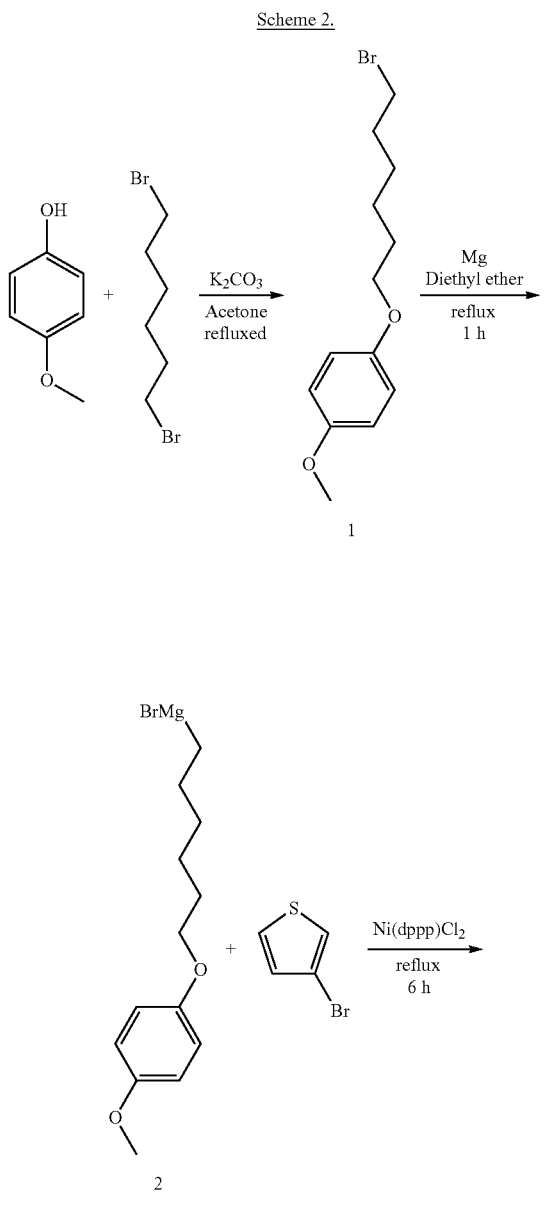

Scheme 2.

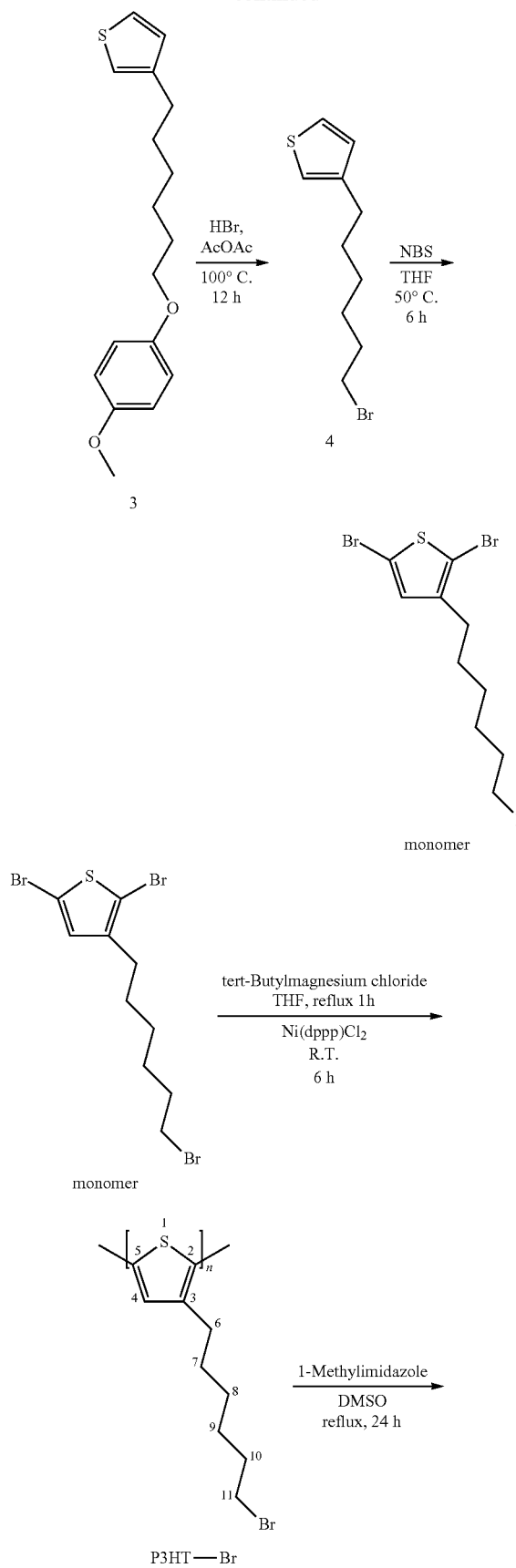

Compound 1 was synthesized following a procedure similar to that described in He, F.; Tang, Y.; Yu, M.; Wang, S.; Li, Y.; Zhu, D. *Advanced Functional Materials* 2007, 17, 996. Yield 60%. 1H NMR (CDCl₃, 300 MHz): d 1.50 (t, 4 H), 1.76"C1.81 (m, 2 H), 1.86"C. C1.93 (m, 2 H), 3.42 (t, 2 H), 3.77 (s, 3 H), 3.91 (t, 2 H), 6.83 (s, 4 H).

Compound 3 was synthesized following a procedure similar to that described in Bäuerle, P.; W"¹rthner, F.; Heid. S. *Angewandte Chemie International Edition in English* 1990, 29, 419. Compound 3 yield 54%. 1H NMR (CDCl₃, 300 MHz): 7.26 (dd, 1H), 6.96 (dd, 1H), 6.94 (dd, 1H), 6.85 (4H), 3.91 (t, 2H), 3.78 (s, 3H), 2.66 (t, 2H), 1.78 (m, 2H), 1.68 (m, 2H), 1.54-1.35 (m, 4H).

Compound 4 was synthesized following a procedure similar to that described in Bäuerle, P.; W"¹rthner, F.; Heid, S. *Angewandte Chemie International Edition in English* 1990, 29, 419. Yield 61%. 1H NMR (CDCl₃, 300 MHz): 7.21 (dd, 1H), 6.92 (dd. 1H), 6.90 (dd, 1H), 3.38 (t, 2H), 2.61 (t, 2H), 1.84 (m, 2H), 1.62 (m, 2H), 1.45 (m, 2H), 1.34 (m, 2H).

Monomer was synthesized following a procedure similar to that described in Sebastien Clement; Akim Tizit; Simon Desbief; Ahmad Mehdi; Julien De Winter; Pascal Gerbaux; Roberto Lazzaronib; Bruno Bourya. *The Journal of Material Chemistry* 2011, 21, 2733. Yield: 90%. 1H NMR (CDCl3, 300 MHz): 6.77 (s, 1H), 3.41 (t, 2H), 2.52 (t, 2H), 1.86 (m, 2H), 1.75-1.34 (m, 6H).

Figure 9:
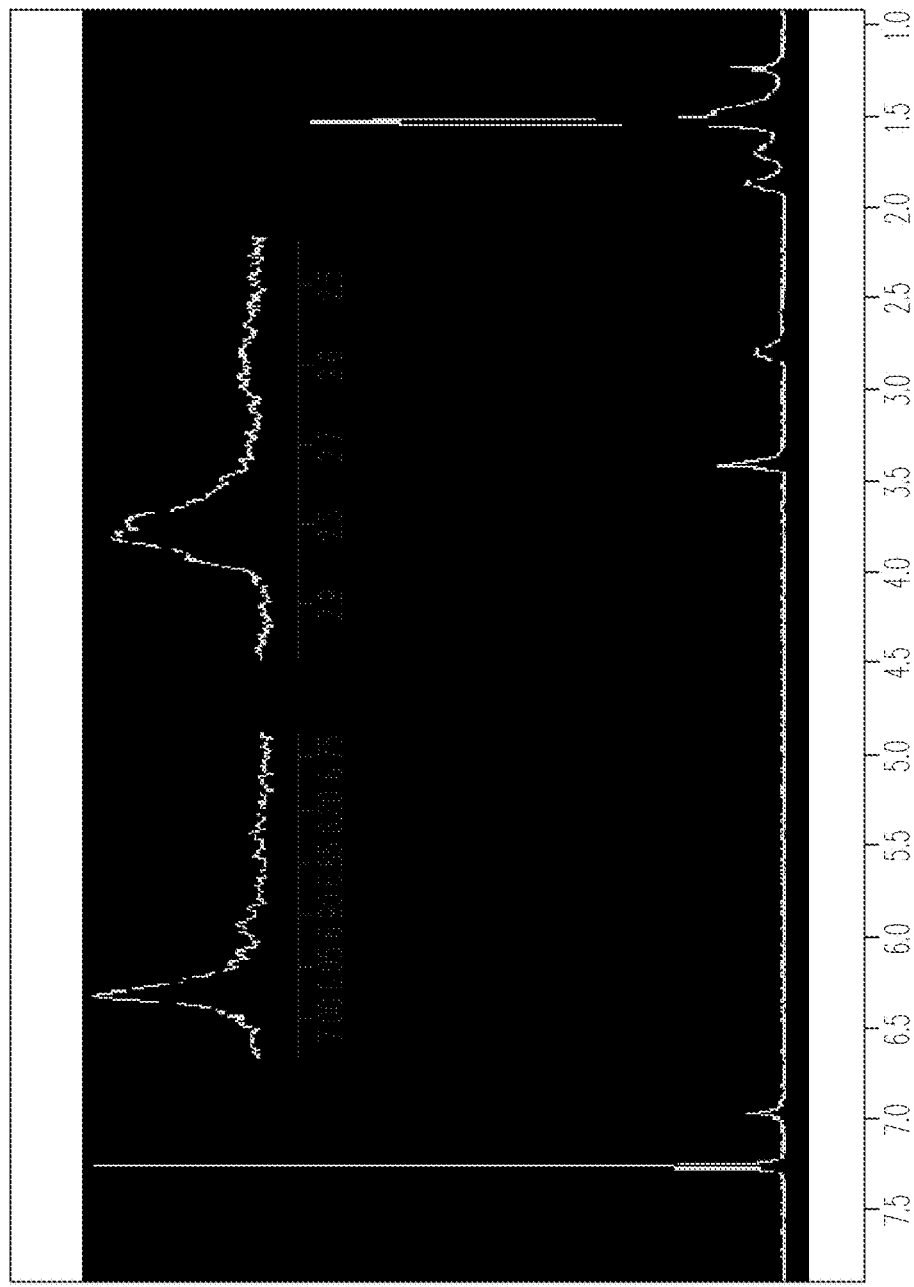
FIG. 9 illustrates the $^1$H NMR spectrum of P3HT-Br in $CDCl_3$, in accordance with various embodiments.

P3HT-Br was synthesized as follows. 2,5-Dibromo-3-(6-bromohexyl)thiophene (200 mg, 0.49 mmol) was dissolved in 5 mL of dry THF. t-Butylmagnesium chloride (0.49 mL, 1.0 M solution in THF) and was added to the mixture and the mixture was then heated to reflux for 1 h. Ni(dppp)Cl₂ (2.65 mg) was added and the solution was stirred at reflux for 2 h, then quenched by HCl. The organic layer was poured into 10 mL of methanol and filtered into a Soxhlet thimble. Soxhlet extractions were performed with methanol (to remove monomer and salts), hexanes (to remove catalyst and oligomers), and DCM. The DCM fraction was reduced and dried in vacuum to afford 30 mg (25% yield) of P3HT-imidazolium. ¹H NMR (CDCl₃, 500 MHz): 6.98 (1H), 3.42 (2H), 2.82 (2H), 1.89 (2H), 1.71-1.25 (6H), Mn=5000 g/mol, PDI=1.39. FIG. 9 illustrates the ¹H NMR spectrum of P3HT-Br in CDCl₃, in accordance with various embodiments. The insets of FIG. 9 show the aromatic region and a-methylene protons, respectively. The ¹H NMR signal confirms P3HT-Br is a highly regioregular and indicates a fine regioregular structure. The molecular weight of P3HT-Br was measured by GPC giving a Mn of 5000 g/mol and a PDI of 1.39.

Figure 10:
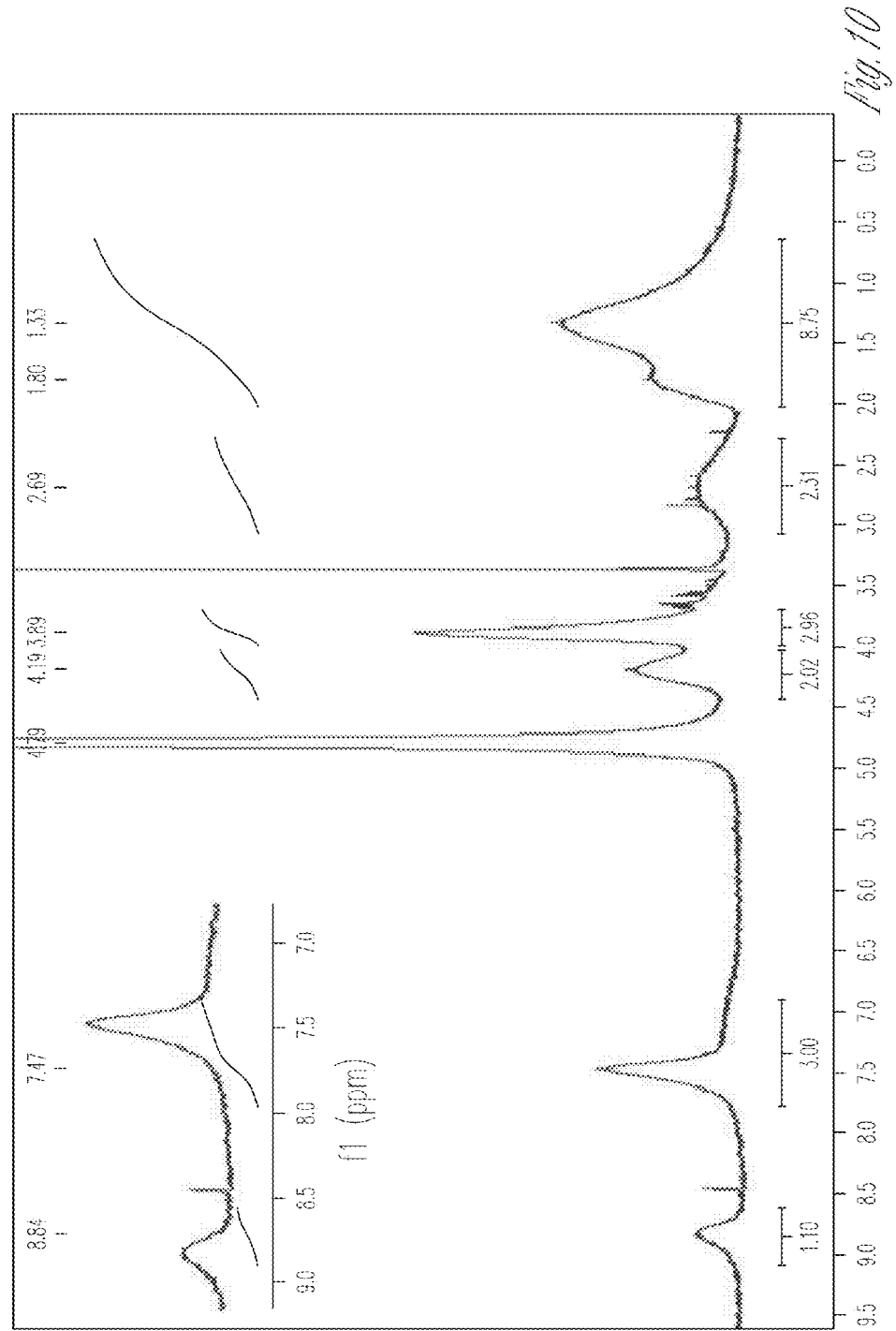
FIG. 10 illustrates the $^1$H NMR of P3HT-imidazolium, in accordance with various embodiments.

P3HT-imidazolium was synthesized following a procedure similar to that described in ondarev, D.; Zedník. J.; Šloufová, I.; Sharf, A.; Procházka, M.; Pfleger, J.; Vohlídal, J. *Journal of Polymer Science Part A: Polymer Chemistry* 2010, 48, 3073 from P3HT-Br. $^1$H NMR (D$_2$O, 500 MHz): 8.94 (1H), 7.47 (3H), 4.19 (2H), 3.89 (3H), 2.69 (2H), 1.80-1.33 (8H), FIG. 10 illustrates the $^1$H NMR (D$_2$O, 500 MHz) of P3HT-imidazolium, in accordance with various embodiments.

Example 1.2.2

Absorption and Fluorescence

Figure 11A:
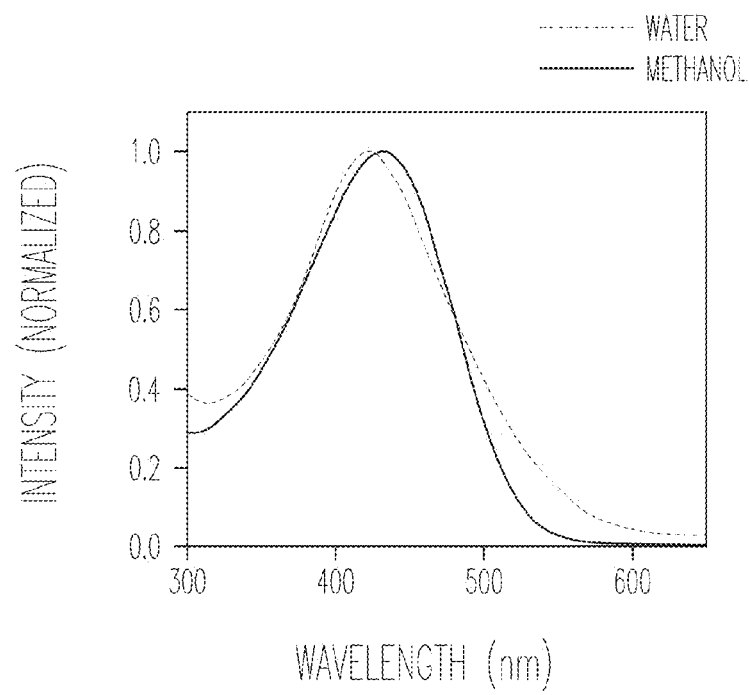
FIGS. 11A-B illustrate the absorption spectrum of P3HT-imidazolium in methanol and water, in accordance with various embodiments.
Figure 11B:
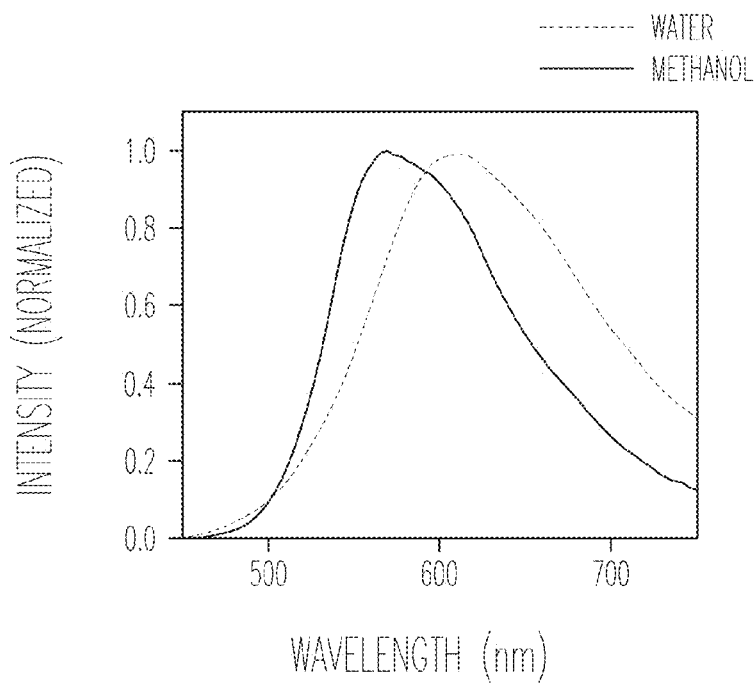

FIGS. 11A-B illustrate the absorption spectrum of P3HT-imidazolium in methanol and water, in accordance with various embodiments.

The fluorescence quenching of P3HT-imidazolium examined in both methanol and water. The fluorescence of conjugated polyelectrolytes (CPEs) can be quenched by very low concentrations of oppositely charged quencher species. This phenomenon is known as amplified quenching and it occurs because the exciton can be delocalized along the polymeric backbone, allowing to have greater chance to be quenched than excitons in small molecular.

Two different cationic quenchers, sodium anthraquinone-2,6-disulfonate (AQS) and pyrophosphate (PPi) have been employed to study the quenching of P3HT-imidazolium by different mechanisms. AQS quenches the florescence of electron rich molecules by photo-induced electron transfer mechanism. See e.g., Liu. Y.; Schanze, K. S. *Analytical Chemistry* 2008, 80, 8605. On the other hand, anionic PPi would induce fluorescence quenching only by triggering aggregation of CPE chains. See e.g., Kim, S. K.; Lee, D. H.; Hong, J.-I.; Yoon, J. *Accounts of Chemical Research* 2008, 42, 23.

Figure 12A:
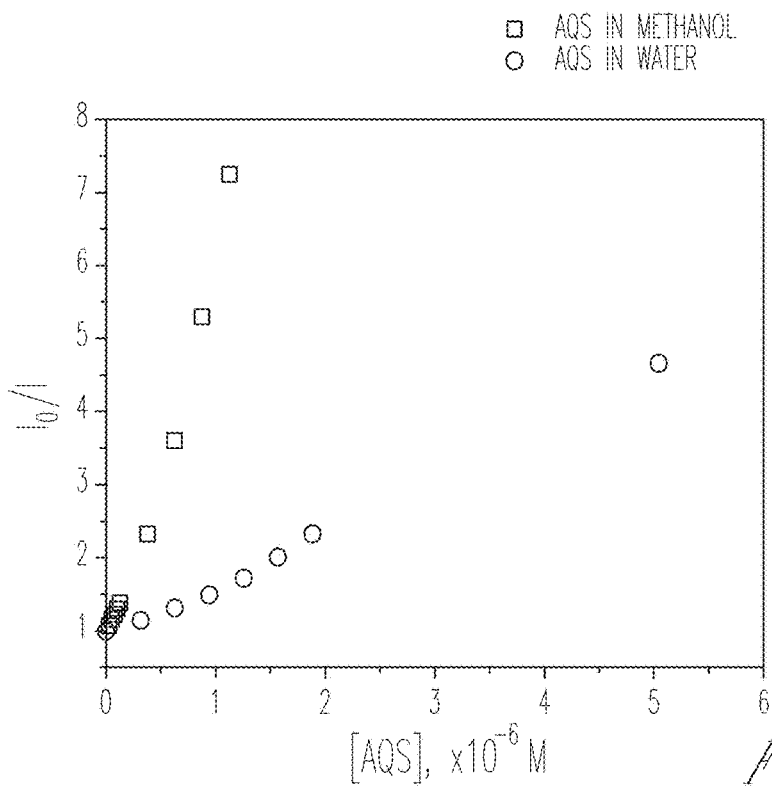
FIGS. 12A-B illustrate Stem-Volmer plots of P3HT-imidazolium with (a) AQS and, (b) PPi as quenchers, in accordance with various embodiments.
Figure 12B:
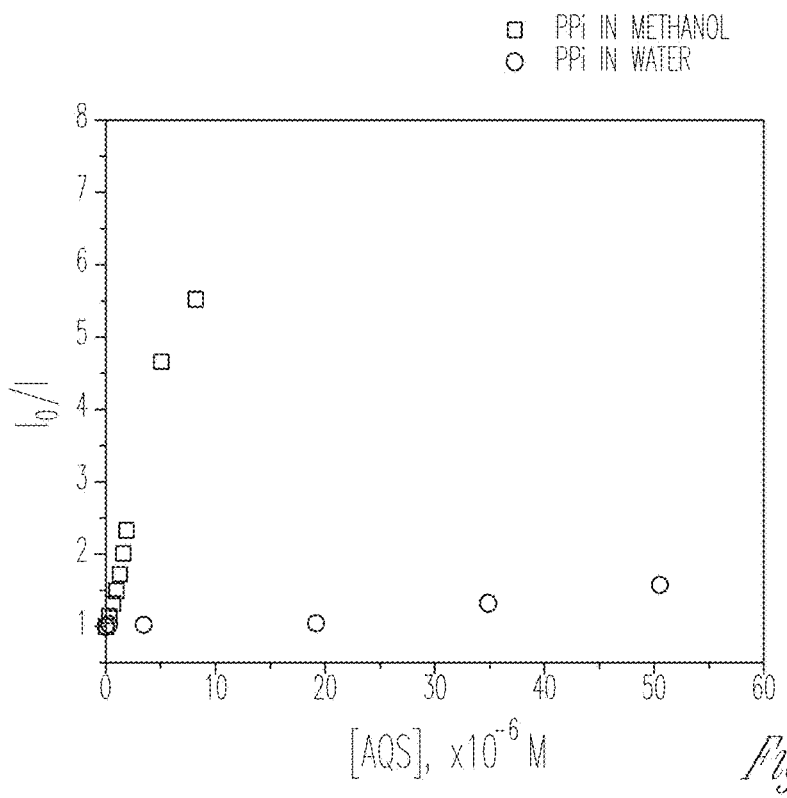

The Stem-Volmer plots of P3HT-imidazolium fluorescence quenching in both methanol and water are showed in FIGS. 12A-B by increasing the concentration of AQS and PPI. The Stem-Volmer quenching constant for the fluorescence quenching are summarized in Table 3. By employing AQS, both Stem-Volmer quenching constants in water and methanol are large which indicates the amplified quenching process in both methanol and water. However, by employing PPi, the Stem-Volmer quenching constants in both methanol and water are remarkably lower than the values obtained by AQS. Moreover, the quenching efficiency is even lower (~$10^3$ M$^{-1}$) in aqueous solution by employing PPi, which provoking aggregation of polymer, because the polymer chains have already forming aggregation before adding AQS.

TABLE 3

Stem-Volmer constants for the fluorescence quenching of P3HT-imidazole by AQS and PPi.

|  | $K_{SV}$ (Methanol) | $K_{SV}$ (Water) |
|---|---|---|
| AQS | 3.5 × 10$^6$ M$^{-1}$ | 5.9 × 10$^5$ M$^{-1}$ |
| PPi | 2.1 × 10$^5$ M$^{-1}$ | 9.9 × 10$^3$ M$^{-1}$ |

Example 1.2.3

Transient Absorption and Singlet Oxygen Sensitization

Figure 13A:
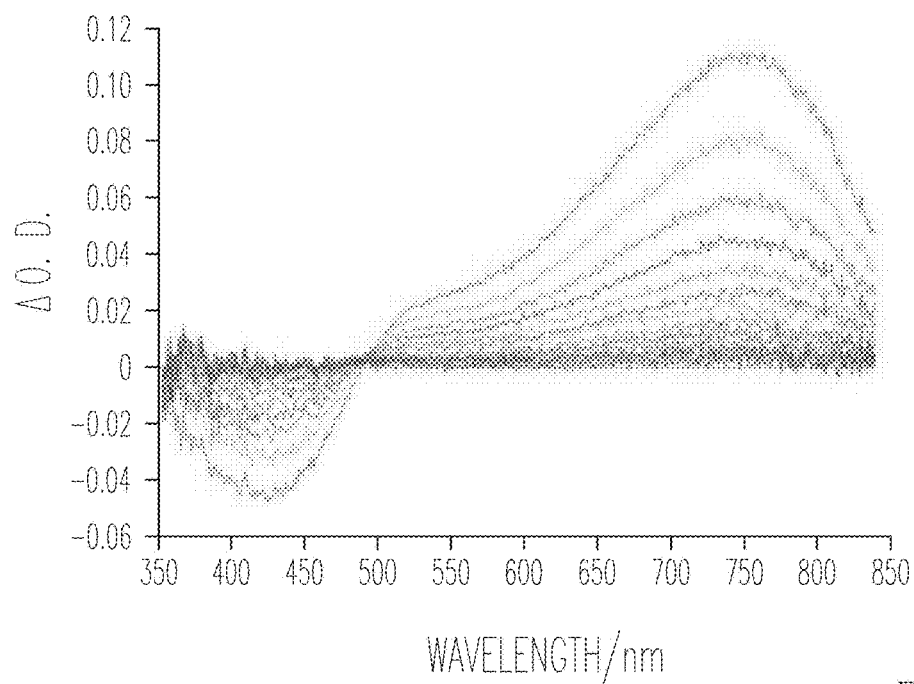
FIGS. 13A-B illustrate the transient absorption difference spectra of P3HT-imidazole in (A) methanol and (B) water, in accordance with various embodiments.
Figure 13B:
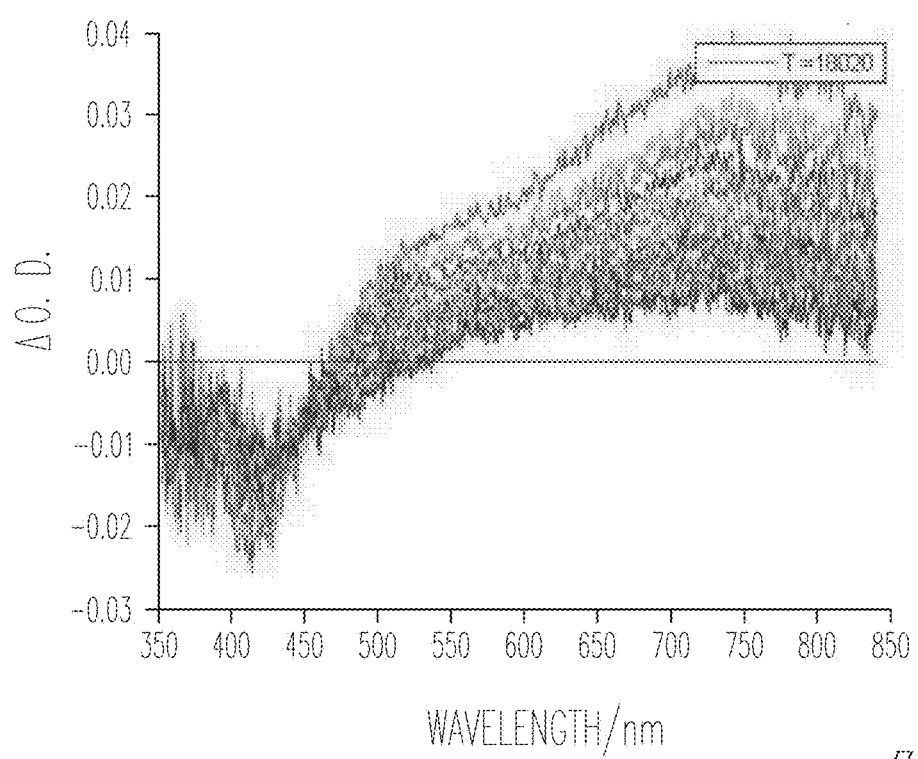

It has been well established that the formation of singlet oxygen plays an important role in biocidal process, and triplet excited state of CPEs is a critical process of generating singlet oxygen. See e.g., orbitt, T. S.; Ding, L.; Ji, E.; Ista, L. K.; Ogawa, K.; Lopez, G. P.; Schanze. K. S.; Whitten. D. G. *Photochemical & photobiological sciences: Official journal of the European Photochemistry Association and the European Society for Photobiology* 2009, 8, 998. Because of the heavy atom effect of sulfur on P3HT-imidazolium, it is expected to have triplet excitation. Thus, triplet-triplet absorption of P3HT-imidazolium has been studied in methanol and water using transient absorption spectroscopy (see e.g., FIGS. 13A-B, illustrating the transient absorption difference spectra of P3HT-imidazole in (A) methanol and (B) water). Transient absorption lifetimes are listed in Table 4. A transient absorption life time of 1.51 µs has been detected in MeOH, indicating P3HT-imidazolium can generate singlet oxygen. However, it is challenging to measure transient absorption in water. Because of the formation of aggregation, the signal of transient absorption in water is weak and its decay is long, which may affect the accuracy of transient absorption life time. Singlet oxygen quantum yield has also been measured in CD$_3$OD by measuring singlet oxygen phosphorescence ~1270 nm in deuterated methanol giving a $\Phi_\Delta$=6.5%.

TABLE 4

Photophysical Data of P3HT-imidazolium.

|  | P3HT (methanol) | P3HT(water) |
|---|---|---|
| $\lambda_{max}$ (absorption/nm) | 421 | 419 |
| $\lambda_{max}$ (fluorescence/nm) | 570 | 611 |
| abs coeff mol/(L*cm) | 5000 | 4000 |
| $\tau_F$/ns | 0.51 | 0.53 |
| $\tau_{transient\ absorption}$/µs | 1.51 | 7.54 |
| $\Phi_F$ | 14.9% | 3.5% |
| $\Phi_\Delta$ (in CD$_3$OD) | 6.80% | |

Example 1.2.4

Biocidal Studies of P3HT-imidazolium

Figure 14A:
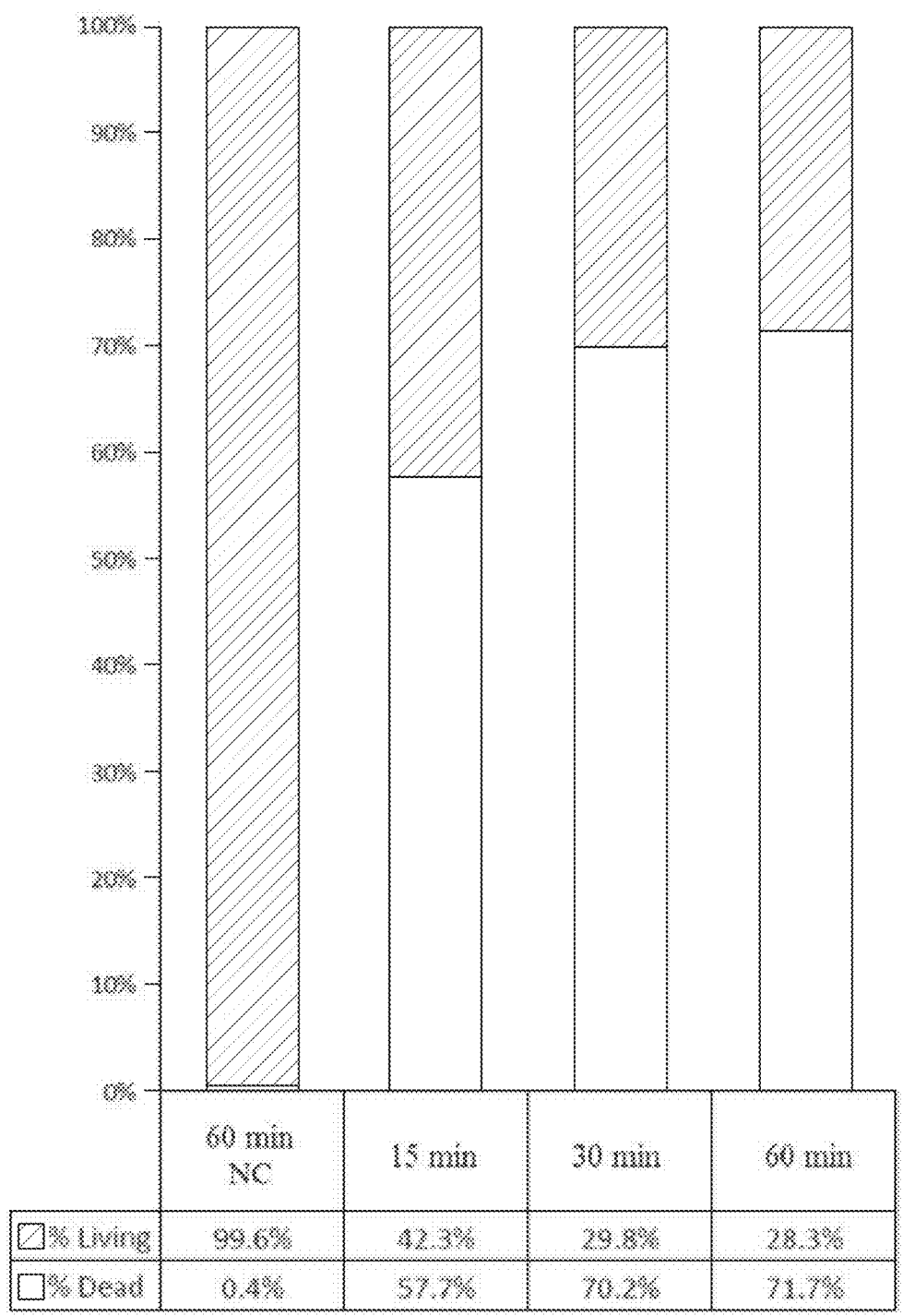
FIGS. 14A-B illustrates the biocidal activity of P3HT-imidazolium against Gram-positive S. aureus, in accordance with various embodiments.
Figure 14B:
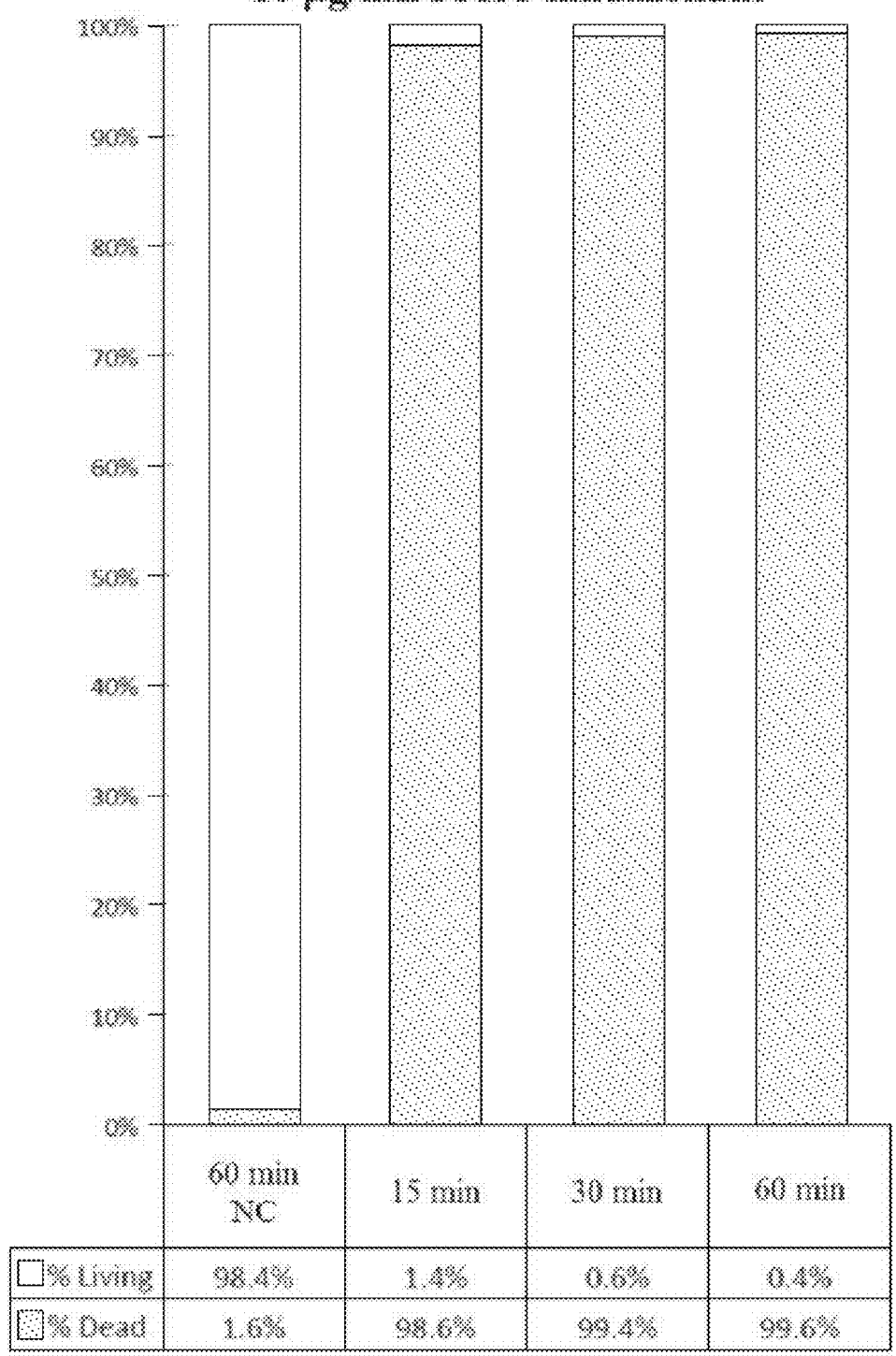
Figure 15A:
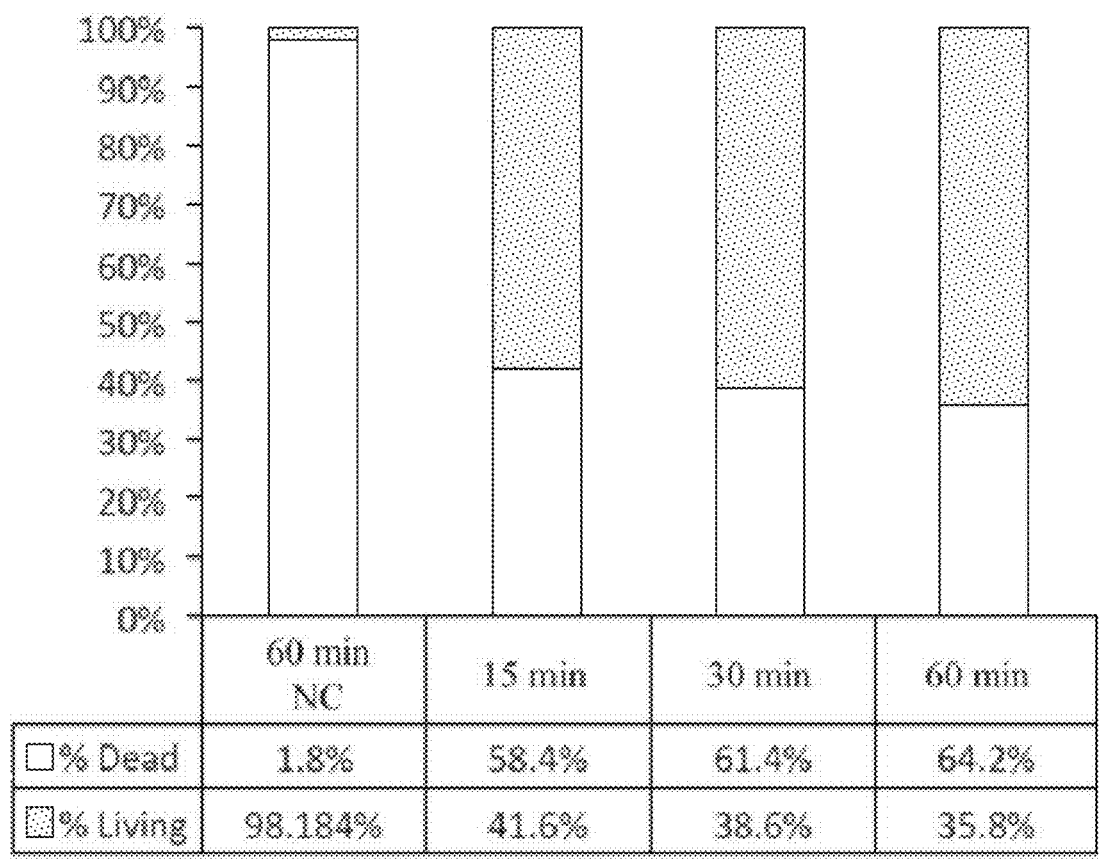
FIGS. 15A-B illustrate the biocidal activity of P3HT-imidazolium against Gram-negative E. coli, in accordance with various embodiments
Figure 15B:
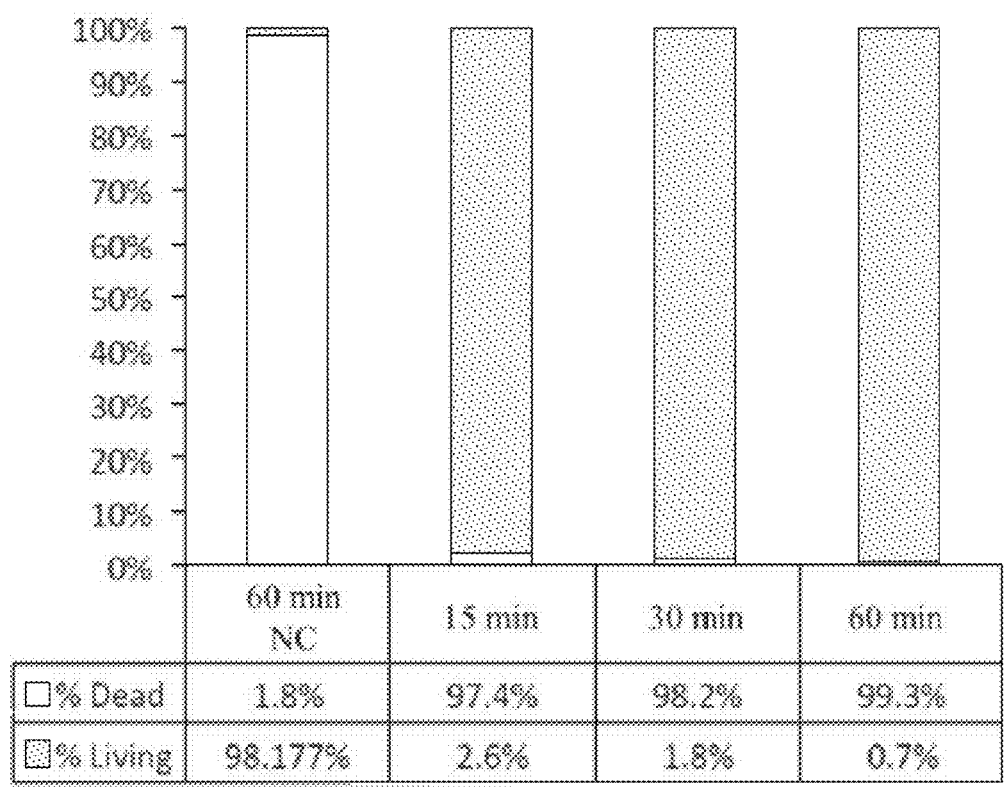

FIGS. 14A-B illustrate the biocidal activity of P3HT-imidazolium against Gram-positive *S. Aureous*. FIGS. 15A-B illustrate the biocidal activity of P3HT-imidazolium against Gram-negative *E. coli*.

Biocidal studies indicate P3HT-imidazolium in low concentration of 10 µg/ml can have a high biocidal activity in the absences of light and in the presence of light. P3HT-imidazolium achieves a 57.7% killing against Gram-positive *S. aureus* in the dark. This indicates that P3HT-imidazolium can disrupt and/or cross the cell membrane of Gram-positive *S. aureus*. In the presence of visible light ($\lambda$=420 nm), P3HT-imidazolium achieves a 98.6% killing against Gram-positive *S. aureus* in less than 15 mins. The biocidal studies indicates that P3HT-imidazolium achieves a high killing when irradiated. These results suggests the ability of imidazolium binding to both Gram-positive and Gram-negative bacteria. The high light-activated bacterial killing of both Gram-positive and Gram-negative strains at low concentrations exhibits the potential of imidazolium functionalized polythiophenes to serve as effective biocides.

Bacterial Growth. All media and buffers were prepared using deionized water with a resistivity of at least 18 MΩ cm. Nutrient broth 234000 (Difco) was prepared according to manufacturer's instructions. Nutrient agar was prepared upon the addition of 8 g/L bacto agar (Difco). *Staphylococcus aureus* (ATCC 10832) and *Escherichia coli* (ATCC 29425) were both grown from glycerol-preserved stock which originated from first-generation cultures of original ATCC lyophilates grown in nutrient broth (containing 20% glycerol) and subsequently stored at −70° C. Cells of the aforementioned strains were grown upon the inoculation of glycerol stock on Difco nutrient agar at 37° C. for 24 hours.

Biocidal testing entailed scraping *S. aureus* or *E. coli* colonies off their agar plates and transferring them to nutrient broth for growth. Cells were then incubated in an Orbital Incubator Shaker (American Instruments, Lafayette, Calif.) for 18 h at 37° C. with rapid shaking (250 rpm). Following the incubation period, cells were washed by two 15 min centrifugations at 4,400 rpm; in each case, supernatant was replaced by 30 mL of 0.85% NaCl following pellet formation.

Flow Cytometry Analysis. Flow cytometry was utilized to determine the cell concentration of *S. aureus* or *E. coli* in the 0.85% NaCl-suspended bacterial stock solutions. The Accuri $C_6$ (Becton Dickinson, Franklin Lakes, N.J.) used was equipped with a blue laser that excites at 488 nm, as well as two filters: a green fluorescence filter (FL-1: 530 nm) and a red fluorescence filter (FL-3: 670 nm long-pass). A primary threshold ensured that only events exhibiting 40,000 FSC-A scatter units were included in the data, while a secondary threshold ensured that only events exhibiting 250 FL-1 fluorescence units (live stain fluorescence channel) were included. The core size of the flow cytometer was set to 10 μm, with a flow rate of 14 μL/min. 100,000 events were recorded in each sample.

For biocidal testing, the stock solution was either diluted or concentrated to 2E7 cells/mL. 500 mL of said bacterial solution was added to glass tubes with either PIM-2 or PIM-4 to reach a final polymer concentration of 5, 10, or 20 μg/mL and a final volume of I mL prior to analysis. Cells were stained with 5 mM SYTO 21 (live stain; Life Technologies, Grand Island, N.Y.) and 1.5 mM Propidium iodide (dead stain; Life Technologies, Grand Island, N.Y.) for 15 min prior to flow cytometry analysis. Flow cytometry-reported biocidal activity was validated with standard plating techniques. This entailed pipetting 50 μL of unstained, diluted sample onto petri dishes of solidified nutrient agar; the plates were allowed to incubate for 18 hours at 37° C. Colonies were counted using ImageJ image-analysis software.

Where noted, samples were exposed to near-visible light via a Luzchem LZC-ORG photoreactor (Luzchem Research, Ontario, Canada) in a translucent 0.5 dr glass vials. This photoreactor was configured with 10 LZC-420 lamps (emission wavelength range of 400-460 nm). To provide uniform light exposure to all samples, the photoreactor is equipped with a rotating carousel. Using a PM100D Optical Power Meter (Thor Labs, Newton, N.J.), the surface power density of this lighting configuration was measured to be 2.28±0.028 mW/cm$^2$.

Example 1.2.5

Biocidal Studies

Figure 16A:
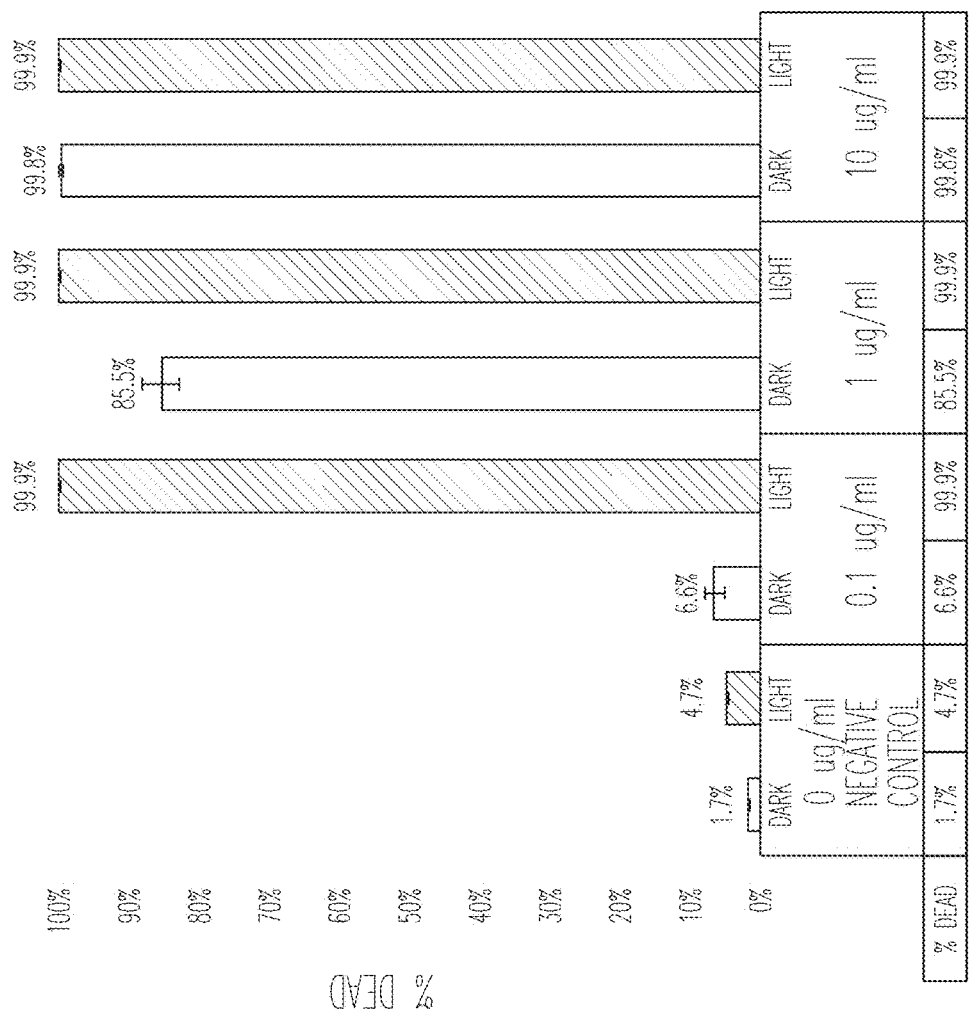
FIGS. 16A-B illustrate (A) bacteria cell viability of Gram-positive S. aureus in the dark and irradiated by blue-violet light and (B) bacteria cell viability of Gram-negative E. coli in the dark and irradiated by blue-violet light, in accordance with various embodiments.
Figure 16B:
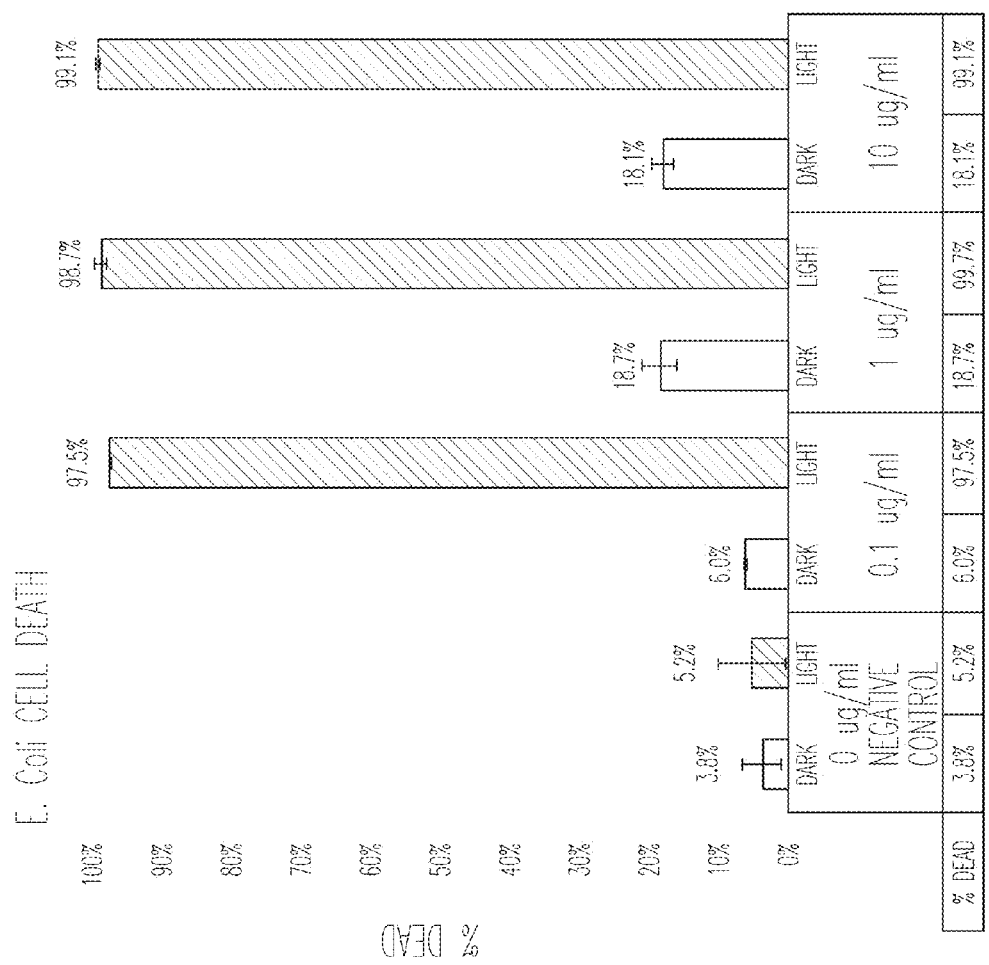

Biocidal Studies. In vitro biocidal studies of P3HT-imidazolium were carried out with both Gram-negative *Escherichia coli* (ATCC 29425) stained with SYTO 9, and Gram-positive *Staphylococcus aureus* (ATCC 10832) stained with SYTO 21 in sample volumes of 1 mL, each containing 1×10$^7$ cells. After incubated with P3HT-imidazolium. The viability of cells were analyzed by flow cytometry. In the dark, P3HT-imidazolium showed strong biocidal activities against Gram-positive *S. aureus* at concentrations ≥1 μg/mL. FIGS. 16A-B illustrate (A) bacteria cell viability of Gram-positive *S. aureus* in the dark and irradiated by blue-violet light and (B) bacteria cell viability of Gram-negative *E. coli* in the dark and irradiated by blue-violet light. Negative control: the bacteria suspension without P3HT-imidazolium. Bacteria sample volumes were 1 mL, each containing 1×10$^7$ cells.

In FIGS. 16A-B, 10 μg/mL of P3HT-imidazolium killed 99.8% of *S. aureus* (Gram-positive) bacteria cells in an hour (FIG. 16A), but exhibited low killing efficiency 18.1% against *E. coli* (Gram-negative) (FIG. 16A). The different killing efficiency against Gram-positive and Gram-negative bacteria is due to their different cell envelope structures. Gram-positive bacteria have thick but porous cell envelope, which mainly made up of an interconnected peptidoglycan layer and cytoplasmic membrane. Large London dispersion force of sulfur atoms on the backbone increased the lipophilicity of P3HT-imidazolium, and its imidazolium cationic groups easily bind to negatively charged bacteria cell envelope. This interaction between P3HT-imidazolium and the bacteria envelop caused the disruption of the cell surface, which leads to the instant dark killing. In contrast to the high dark killing efficiency against *E. coli*, due to the protection of an extra outer lipopolysaccharide membrane, P3HT-imidazolium is less likely to penetrate the cell envelop and of *E. coli* to disrupt the cytoplasmic membrane. It is believed that P3HT-imidazolium shows the dark toxicity against *E. coli* through the "ion-exchange" process. To study the light biocidal activity of P3HT-imidazolium, *S. aureus* and *E. coli* bacterial strains are incubated separately with P3HT-imidazolium with concentrations from 0.1-10 μg/mL in physiological saline solution, and then the irradiated by blue-violet light ($\lambda_{peak}$=420 nm, power=2.28±0.03 mW/cm$^2$) for an hour. No significant cells death by irradiation without P3HT-imidazolium were observed (FIG. 16, negative control), and our light dosage (8.2 J/cm$^2$) is low compared to other photoinactivation materials study. Remarkably, in the light, P3HT-imidazolium killed 99.9% of *S. aureus* bacteria and 97.5% of *E. coli* in an hour with an extremely low concentration of 0.1 μg/mL, which exhibits its great potential in clinical applications. Both *S. aureus* and *E. coli* bacteria cells are able to be disrupted by the singlet oxygen and other reactive oxygen species generated by P3HT-imidazolium. Except the relatively high singlet oxygen yield of P3HT-imidazolium and the strong binding affinity of imidazolium groups, we believe other two reasons also made contributions to the remarkable killing efficiency. First, the backbone of P3HT-imidazolium is very lipophilic, which benefited to the binding between P3HT-imidazolium and bacteria cell envelop. Stronger binding causes the short-life-time singlet oxygen generated close to the bacteria envelop, which leads to the rapid interaction between singlet oxygen and bacteria damaging multiple cellular components. Second, the insertion of P3HT-imidazolium into the bacteria liposome leads to some level of deaggregation of the polymer. The singlet oxygen quantum yield of P3HT derivatives are higher than 40% in benzene solvents, but are lower than 10% in methanol and water due to the non-radiative decay to the ground state attributed to the formation the aggregation. The deaggregation process is believed to recover the singlet oxygen quantum yield to some extent, and increase the inactivation efficiency.

Figure 17A:
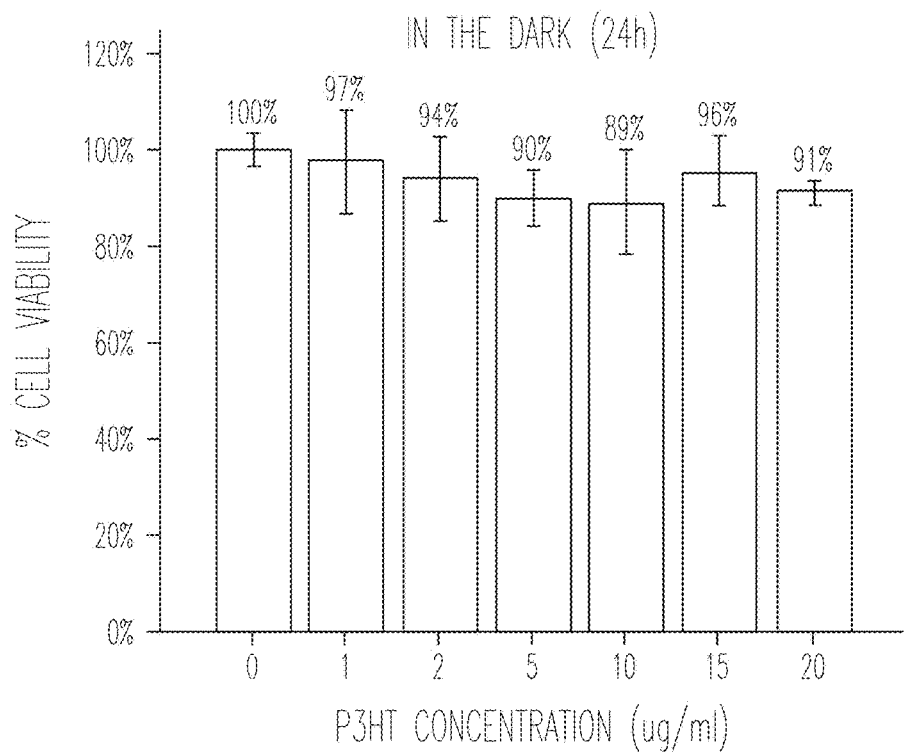
FIGS. 17A-B illustrate (A) Viability of HeLa cells in the dark with P3HT-imidazolium (0-10 μg/mL) for 24 hours and (B) viability of HeLa cells with P3HT-imidazolium (0-10 μg/mL) irradiated by blue for 1 hour, in accordance with various embodiments.
Figure 17B:
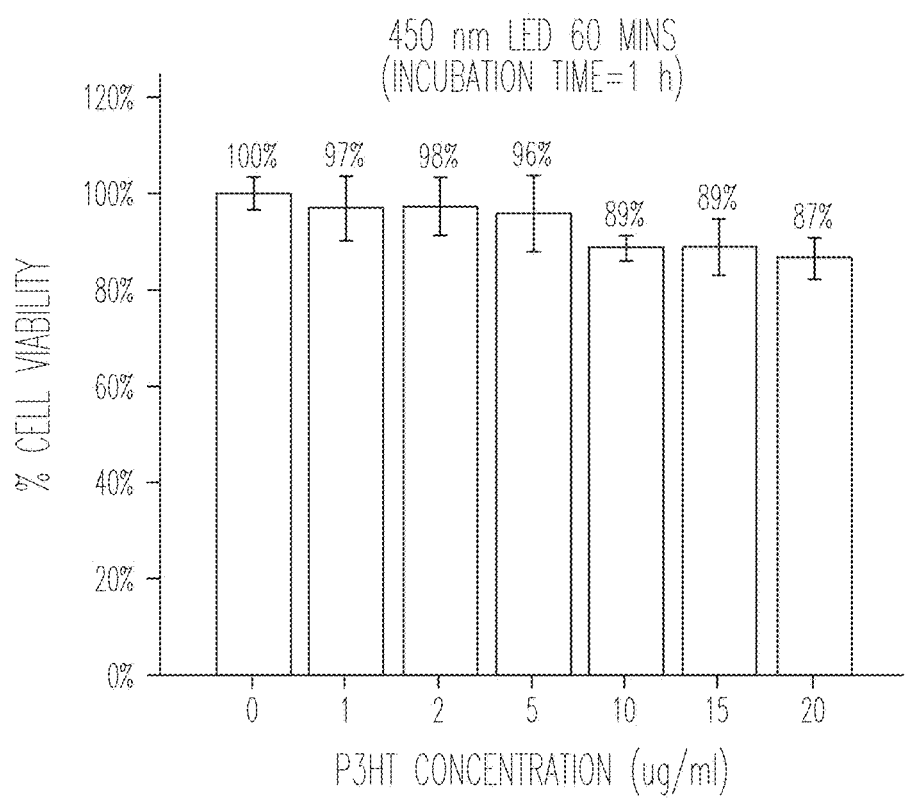

To evaluate the biocompatibility and selectivity of P3HT-imidazolium at the cellular level, the toxicity and interaction of P3HT-imidazolium with mammalian cells were studied with HeLa cells (human cervical cancer cells). Mammalian cell viability analysis were carried out by the 3-(4,5-dimethylthiazol-2-yl)-5-(3-carboxymethoxyphenyl)-2-(4-sulfophenyl)-2H-tetrazolium (MTS) assay 24 hours after treatments. FIGS. 17A-B illustrate (A) Viability of HeLa cells in the dark with P3HT-imidazolium (0-10 µg/mL) for 24 hours and (B) viability of HeLa cells with P3HT-imidazolum (0-10 µg/mL) irradiated by blue for 1 hour, in accordance with various embodiments. After incubated P3HT-imidazolium (0.1-10 µg/mL) with HeLa cells at 37° C. for 24 h in the dark, the viability of HeLa cells was not affected significantly (FIG. 17A). Even with a high concentration (20 µg/mL) of P3HT-imidazolium, the viability of HeLa cells was still higher than 90%, which proved P3HT-imidazolium under 20 µg/mL has no obvious dark toxicity to HeLa cells. Under illumination (blue light, $\lambda_{peak}$=450 nm, power=1.8 mW/cm$^2$), the viability of HeLa cells was essentially unaffected (FIG. 17B) in an hour, while both Gram positive and negative bacteria are efficiently killed. The HeLa cells viability results in the dark and light demonstrated the selective inactivation of P3HT-imidazolium. To further investigate the mechanism of the selectivity, confocal laser scanning microscopy was utilized to image the fluorescence signals of HeLa cells incubated with P3HT-imidazolium. HeLa cells were first incubated with P3HT-imdazolium=10 µg/mL for an hour, and then washed with buffer to remove unbounded P3HT-imidazolium.

Using fluorescence nuclear labeling, there was no P3HT-imidazolium fluorescence signals inside HeLa cells, which confirmed the unbound property of P3HT-imidazolium to mammalian cells. Negatively charged phospholipids of bacteria proved a great driving force for P3HT-imidazolium to bind to bacteria instantly, but P3HT-imidazolium is not able to bind to mammalian cells in a short time due to the lack of electrostatic driving force. Furthermore, this explanation was supported quantitatively by the observation of less negative ζ potentials of mammalian cell membrane surfaces than bacteria membrane surfaces. In addition to the surface charge, the uptake process of HeLa cells has also been studied. P3HT-imidazolium fluorescence signals were observed inside HeLa cells after the incubation for 8 hours. This positive charged P3HT-imidazolium enhanced the cellular uptake of HeLa cells, resulting in the accumulation of polymers in HeLa cells. However, this uptake process takes much longer than the inactivation of bacteria, so the different targeting rates towards bacteria and HeLa cells can be applied to achieve the selective killing of bacteria over mammalian cells.

Part II.

A novel variety of antimicrobial substrates were fabricated using a rapid and facile procedure. Preliminary studies demonstrated these substrates exhibit antimicrobial activity against Gram-positive *Staphylococcus aureus* and Gram-negative *Pseudomonas aeruginosa*. The first samples were prepared using a commercial sample of a pure cellulose wipe and treating it with a solution of a high molecular weight polymers synthesized by the UF investigators known as PPE-DABCO. The samples were tested after drying by immersion in purified water (Milli-Q) at room temperature for a week. Little to no leaching was detected. Incompletely dried samples were found to exhibit some leaching, which is probably from partially wet samples of PPE-DABCO, not fully incorporated into the wipe. The wipes were tested as antibacterial agents against Gram-negative *Pseudomonas aeruginosa* PA01 and Gram-positive *Staphylococcus aureus*.

Example 2.1

Fabrication

These textiles can be prepared in a matter of hours, and use Kimwipes (Kimberly-Clark) as the primary substrate. Kimwipes measuring 9 in$^2$ were granted antimicrobial properties upon being exposed to a high concentration of p-phenylene ethynylene (PPE)—which was synthesized by Parthasarathy, under the supervision of Dr. Kirk Schanze. In particular, a PPE by the name of PPE-DABCO was used in the experiments described herein, having the following structure:

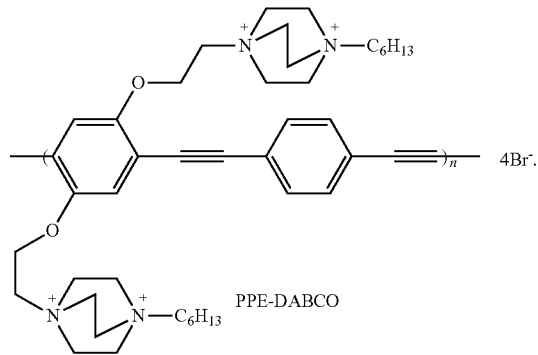

PPE-DABCO was dissolved in a combination of deionized water and dimethyl sulfoxide such that the final concentration was approximately 4 mg/mL. 200 µL of PPE-DABCO stock solution was then distributed across the surface area of a 9 in$^2$ Kimwipe textile such that the entire textile appeared saturated. The treated Kimwipe textile was then permitted up to 18 hours to completely dry.

Figure 18:
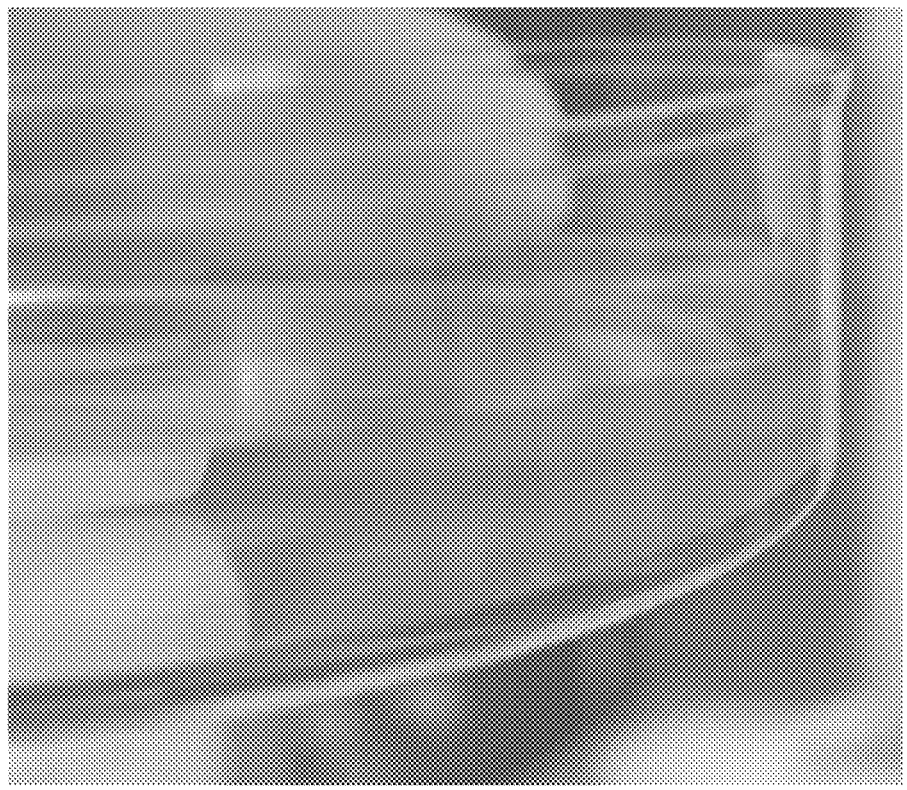
FIG. 18 illustrates a photograph of a treated Kimwipe textile in water after 7 days, in accordance with various embodiments

A treated Kimwipe was cut into a small textile measuring 1 in$^2$ before being submerged in deionized water for a period of 7 days. The absorbance and fluorescence (data not shown) of said water was then evaluated as a means to gauge leaching of the PPE-DABCO into the water. Absorbance and fluorescence (400 nm excitation) readings suggest that the treated Kimwipe textiles exhibit minimal leaching of PPE- DABCO in water. FIG. 18 illustrates a photograph of a treated Kimwipe textile in water after 7 days, showing that, even after 7 days, the water has remained clear to the human eye and appears uncontaminated.

Example 2.2

Demonstrating Antimicrobial Properties

The treated Kimwipe textile was then demonstrated to prevent growth of Gram-positive *Staphylococcus aureus* and Gram-negative *Pseudomonas aeruginosa*. These bacteria were grown overnight in nutrient broth, rinsed twice, and subsequently diluted to a concentration of 1E6 cells/mL in sterile physiological saline solution. Cell suspensions (60 μL/agar plate) were streaked across nutrient agar plates and permitted up to 10 minutes to dry. Treated Kimwipe textiles were then gently placed on top of streaked-side of the agar and held in place with a translucent microscope slide: untreated Kimwipes were used as negative controls. Agar plates (covered with either treated or untreated Kimwipes) were then exposed to near-visible light (~420 nm) for 30 minutes: some samples were left in the dark as a negative control. Samples were then incubated for 18 hours at a temperature of 37° C. in order to promote bacterial growth on the agar plate. Following incubation, the microscope slide and Kimwipe were removed from the agar plate, and photographed as a means to qualitatively gauge bacterial growth (or lack thereof).

Figure 19:
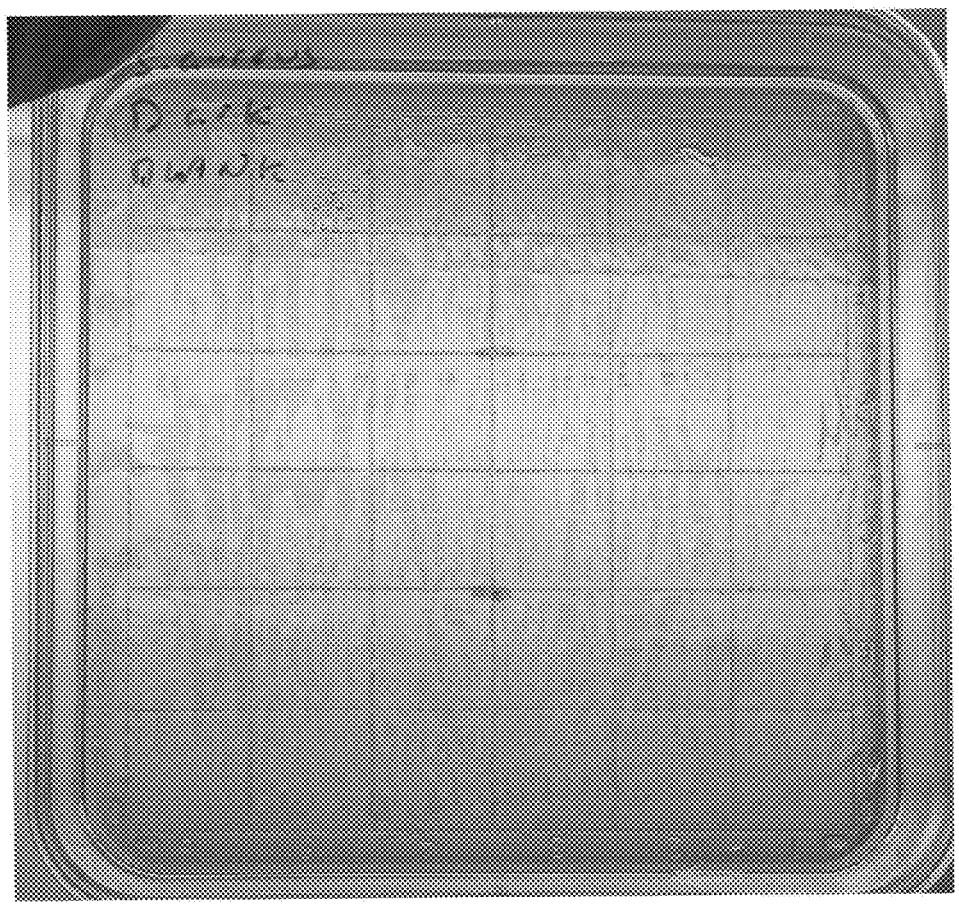
FIG. 19 illustrates a photograph of gram-positive S. aureus exposed to untreated Kimwipe in the dark, in accordance with various embodiments
Figure 20:
FIG. 20 illustrates a photograph of gram-positive S. aureus exposed to PPE-treated Kimwipe in the dark, in accordance with various embodiments
Figure 21:
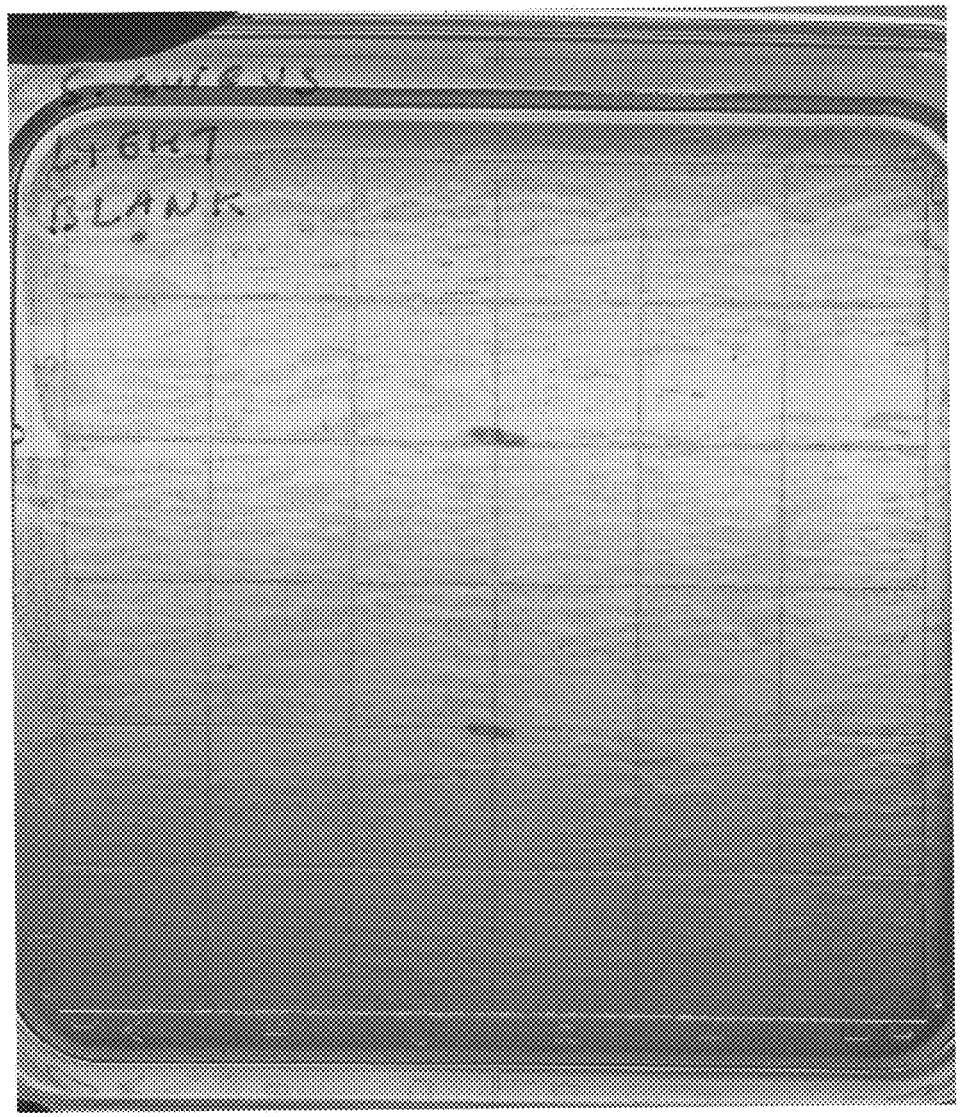
FIG. 21 illustrates a photograph of gram-positive S. aureus exposed to untreated Kimwipe in the light, in accordance with various embodiments.
Figure 22:
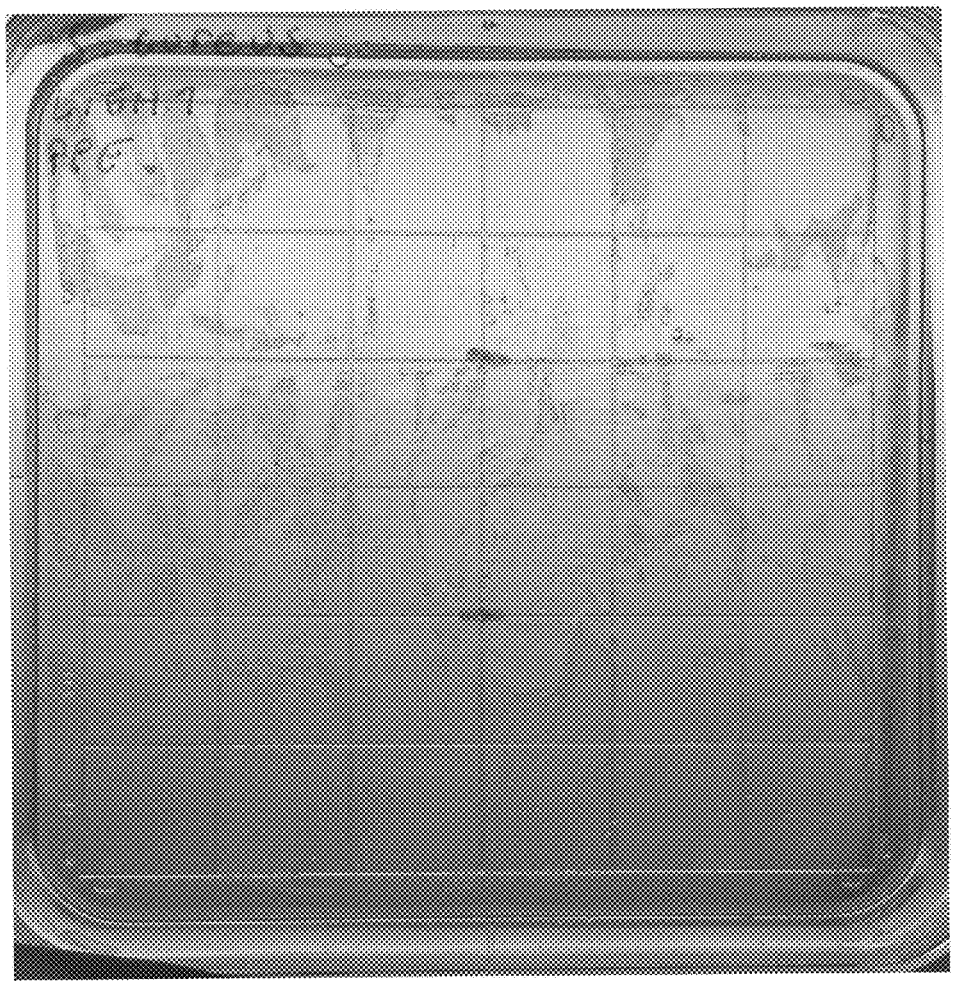
FIG. 22 illustrates a photograph of gram-positive S. aureus exposed to PPE-treated Kimwipe in the light, in accordance with various embodiments.

Inspection of the *S. aureus*-streaked agar plates (FIGS. 19-22) reveals large regions where bacterial growth was completely inhibited (similar images for *P. aeruginosa*-streaked agar plates are not shown). This inhibition of growth is prominent in the case of treated Kimwipe textiles: conversely, bacteria appears able to grow to a confluent state where exposed to untreated Kimwipes. FIG. 19 illustrates a photograph of gram-positive *S. aureus* exposed to untreated Kimwipe in the dark. FIG. 20 illustrates a photograph of gram-positive *S. aureus* exposed to PPE-treated Kimwipe in the dark. FIG. 21 illustrates a photograph of gram-positive *S. aureus* exposed to untreated Kimwipe in the light. FIG. 22 illustrates a photograph of gram-positive *S. aureus* exposed to PPE-treated Kimwipe in the light.

Example 2.3

Implications/Broader Impact

There are numerous implications associated with the results of these preliminary experiments. The fact that PPE-treated Kimwipes appear able to largely inhibit the growth of bacteria on a solid, relatively dry surface (nutrient agar), suggests that PPE-DABCO is capable of inhibiting bacterial growth in a non-aqueous environment. The fact that bacterial growth appears to be inhibited without any mechanical wiping action suggests that these treated textiles may prove to be immensely effective at cleaning solid surfaces (e.g. counter tops, keyboard surfaces, medical devices, or warfighter machinery). Materials similarly coated with PPE-DABCO could also be incorporated into bandages or wound dressings. Furthermore, PPE-DABCO has previously been reported to kill bacteria by broad-spectrum, non-specific mechanisms that are unlikely to induce bacterial resistance; this suggests that implementation of these treated Kimwipes may mitigate nosocomial infections.

Future experiments will serve to investigate the effects of drying time (following PPE saturation) has on preventing bacterial growth. A shorter drying time is believed to result in enhanced leaching of the PPE, while complete drying (as shown herein) results in minimal leaching. For example, a "wet" treated Kimwipe (one that hasn't been permitted enough time to dry) may prove better at inhibiting bacterial growth long-term, while a "dry" treated Kimwipe (one that has dried overnight, as described herein) may prove better at physically removing bacteria from a solid surface. It is also believed that treatment with oligo-p-phenylene ethynylenes (OPEs) instead of PPEs may have implications in controlled leaching. OPE-treated Kimwipes will be characterized moving forward.

In addition, the fact that PPE-treated Kimwipes are allowed to fully dry and still exhibit antimicrobial properties leads us to believe that PPEs or OPEs will also prove useful in an aerosolized spray format. Ideally, the PPE or OPE spray could be used to decontaminate and/or prevent further bacterial growth of rough surfaces that may otherwise prove difficult to cleanse with mechanical wiping mechanism. Once the applied spray dries on the applied surface, it is implied that deposited PPE or OPE could continue to work after drying; again, this is what the data described herein suggests: that even in the absence of an aqueous medium (upon fully drying), PPES and OPEs retain the ability to inhibit bacterial growth.

Example 2.4

Synthesis of Antimicrobial Compounds

The compounds listed in Table 5 were synthesized according to procedures reported in the literature. OPE-1, OPE-2, OPE-3, S-OPE-1(H), S-OPE-2(H), S-OPE-3(H) and S-OPE-1(COOEt), S-OPE-2(COOEt), and S-OPE-3 (COOEt) were synthesized according to the procedure reported in *Langmuir*, 2011, 27 (8), pp 4945-55 or *Langmuir*, 2009, 25 (1), pp 21-25. EO-OPE-1($C_3$), EO-OPE-1($C_2$), EO-OPE-1(Th), EO-OPE-1(TH, $C_2$), and EO-OPE-1($SO_3$) were synthesized according to the procedure reported in *J. Phys. Chem. Lett.*, 2010, 1 (21), pp 3207-3212. PPE-DABCO and PPE-TH were synthesized according to the procedure reported in *Macromolecules*, 2006, 39, pp 6355-6366. EO-OPE-(DABCO) was synthesized according to the procedure reported in Langmuir, 2012, 28 (31), pp 11286-11290. PPE-$NMe_3$-5-COOEt, PPE-$NMe_3$-7-COOEt, PPE-$NMe_3$-9-COOEt, PPE-$NMe_3$-11-COOEt, PPE-$NMe_3$-14-COOEt, PPE-$NMe_3$-20-COOEt, PPE-$NMe_3$-49-COOEt, PPE-$NMe_3$-5-COOH, PPE-$NMe_3$-7-COOH, PPE-$NMe_3$-9-COOH, PPE-$NMe_3$-11-COOH, PPE-$NMe_3$-14-COOH, and PPE-$NMe_3$-20-COOH were synthesized according to the procedure reported in *Langmuir*, 2011, 27(17), pp 10763-10769.

TABLE 5
| Name | Structure |
|---|---|
| OPE-1 | 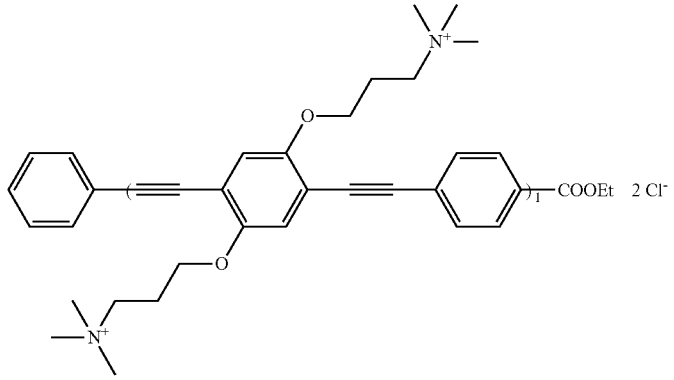 |
| OPE-2 | 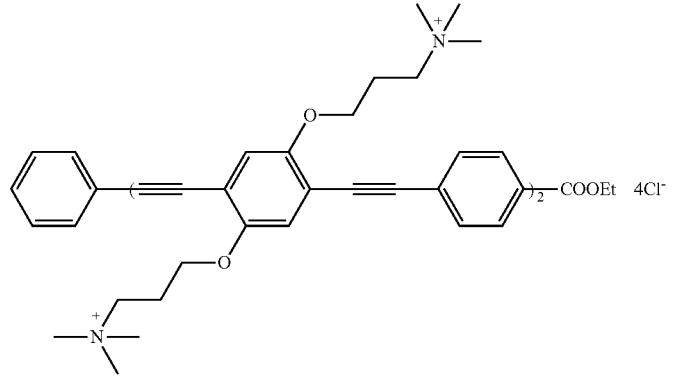 |
| OPE-3 | 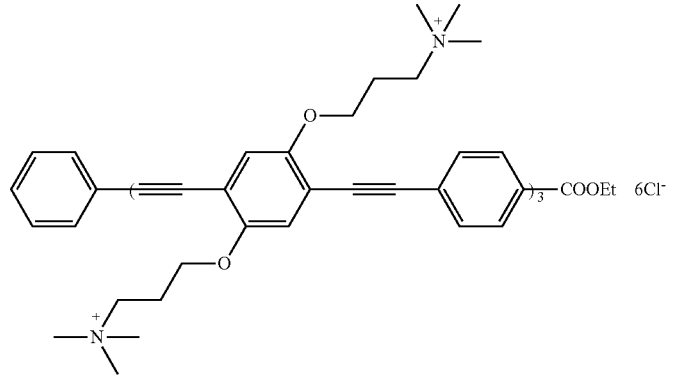 |
| S—OPE—1(H) | 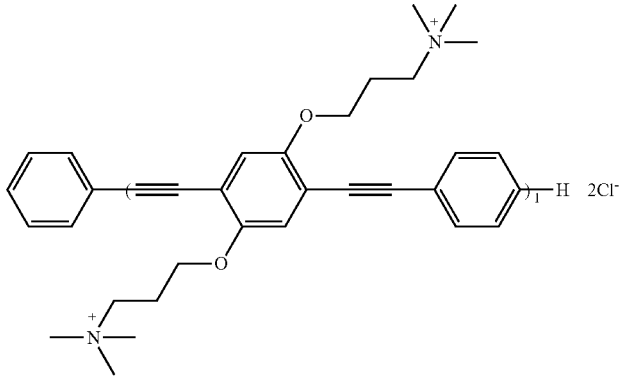 |

TABLE 5-continued

| Name | Structure |
|---|---|
| S—OPE—2(H) | Phenyl—C≡C—[2,5-bis(O(CH₂)₃N⁺(CH₃)₃)phenylene]—C≡C—(C₆H₄)₂—H  4Cl⁻ |
| S—OPE—3(H) | Phenyl—C≡C—[2,5-bis(O(CH₂)₃N⁺(CH₃)₃)phenylene]—C≡C—(C₆H₄)₃—H  6Cl⁻ |
| S—OPE—1(COOEt) | EtOOC—(C₆H₄)—C≡C—[2,5-bis(O(CH₂)₃N⁺(CH₃)₃)phenylene]—C≡C—(C₆H₄)₁—COOEt  2Cl⁻ |
| S—OPE—2(COOEt) | EtOOC—(C₆H₄)—C≡C—[2,5-bis(O(CH₂)₃N⁺(CH₃)₃)phenylene]—C≡C—(C₆H₄)₂—COOEt  4Cl⁻ |

TABLE 5-continued

| Name | Structure |
|---|---|
| S—OPE—3(COOEt) | Structure with EtOOC-phenyl-alkyne-central phenyl (with two O(CH₂)₃N⁺(CH₃)₃ substituents)-alkyne-phenyl-COOEt, repeated 3 times; 6Cl⁻ counterion |
| EO—OPE—1(C3) | $(H_3C)_3N^+(H_2C)_2O$—phenyl—C≡C—phenyl—C≡C—phenyl—$O(CH_2)_2N^+(CH_3)_3$  2I⁻ |
| EO—OPE—1(C2) | $(H_3C)_3N^+(H_2C)_2O$—phenyl—C≡C—phenyl—C≡C—phenyl—$O(CH_2)_2N^+(CH_3)_3$  2I⁻ |
| EO—OPE—1(Th) | $(H_3C)_3N^+(H_2C)_3O$—phenyl—C≡C—thiophene—C≡C—phenyl—$O(CH_2)_3N^+(CH_3)_3$  2I⁻ |
| EO—OPE—1(Th, C2) | $(H_3C)_3N^+(H_2C)_2O$—phenyl—C≡C—thiophene—C≡C—phenyl—$O(CH_2)_2N^+(CH_3)_3$  2I⁻ |
| EO—OPE—1(SO₃) | $^-O_3S(H_2C)_3O$—phenyl—C≡C—phenyl—C≡C—phenyl—$O(CH_2)_3SO_3^-$  2Na⁺ |
| T3—NMe₃ | $(H_3C)_3N^+(C)_3$—thiophene—thiophene—thiophene—$(CH_2)_3N^+(CH_3)_3$  2Cl⁻ |
| BTZ—Th—NMe₃ | $(H_3C)_3N^+(H_2C)_3$—thiophene—(N-methyl benzotriazole)—thiophene—$(CH_2)_3N^+(CH_3)_3$  2Cl⁻ |
| BTD—Th—NMe₃ | $(H_3C)_3N^+(H_2C)_3$—thiophene—(benzothiadiazole)—thiophene—$(CH_2)_3N^+(CH_3)_3$  2Cl⁻ |

TABLE 5-continued
| Name | Structure |
|---|---|
| PIM-2 | 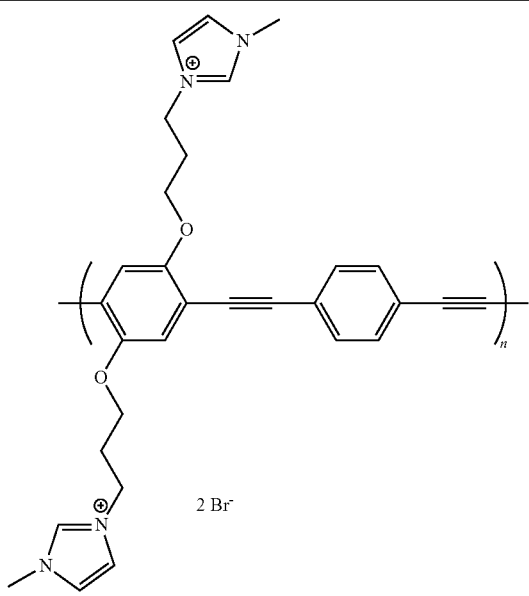 |
| PIM-4 | 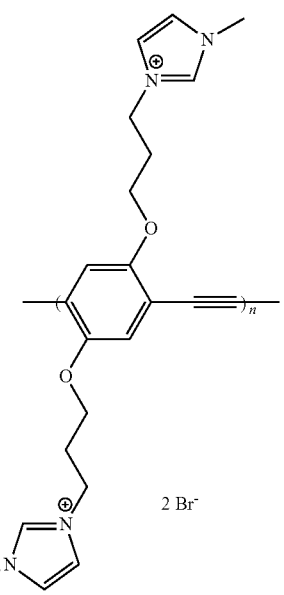 |
| PPE—Th—NMe$_3$—COOEt (n = 40) | 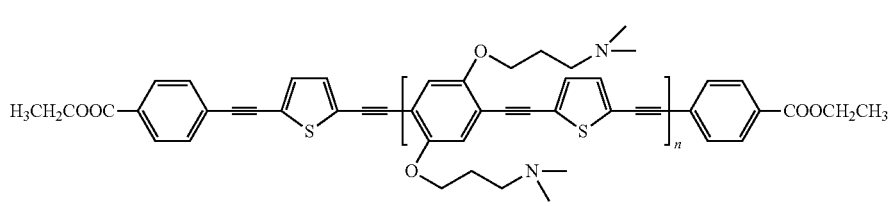 |
| PPE—Th—NMe$_3$—COOEt (n = 11) | 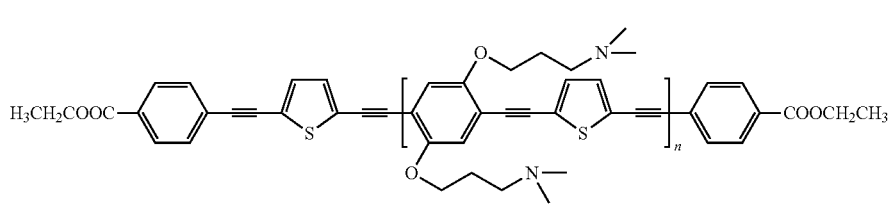 |

TABLE 5-continued
| Name | Structure |
|---|---|
| PPE—DABCO | 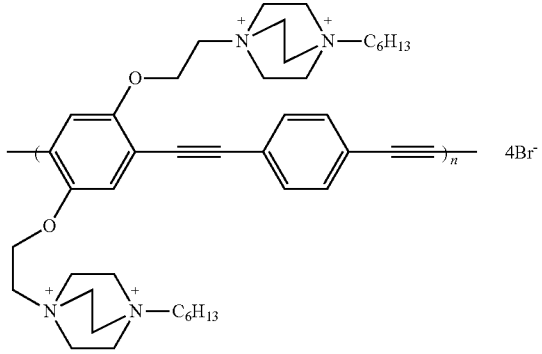 |
| PPE—Th | 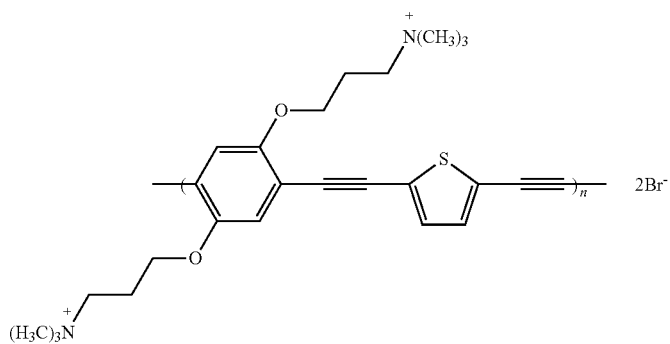 |
| NONE | 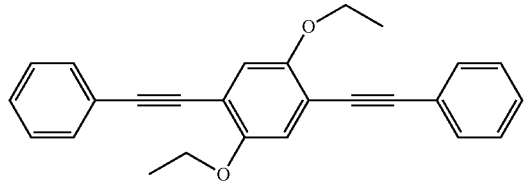 [SMILES: CCOc1cc(C#Cc2ccccc2)c(OCC)cc1C#Cc1ccccc1] |
| EO—OPE—1(DABCO) | 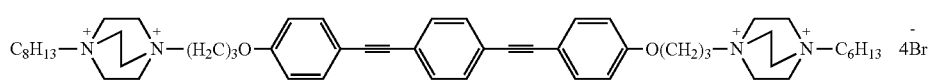 |
| PE—SO3—H | 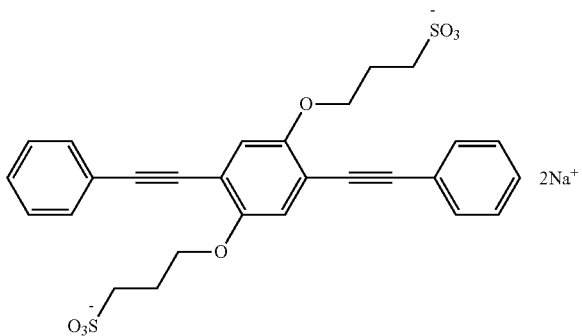 |

TABLE 5-continued
| Name | Structure |
|---|---|
| PE—SO3—COOH | 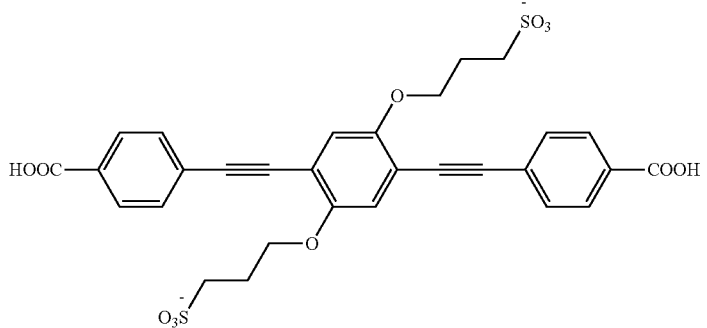 |
| PE—SO3—COOEt | 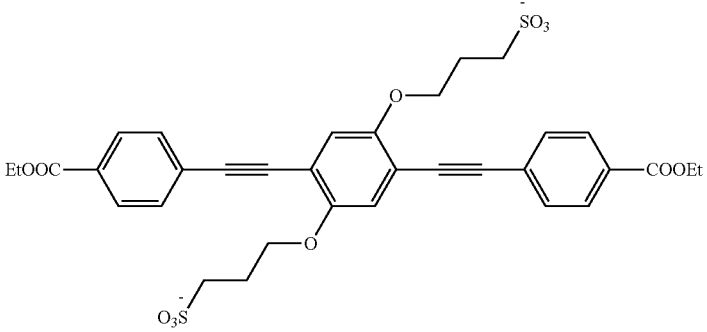 |
| PPE—NMe₃-5-COOEt | 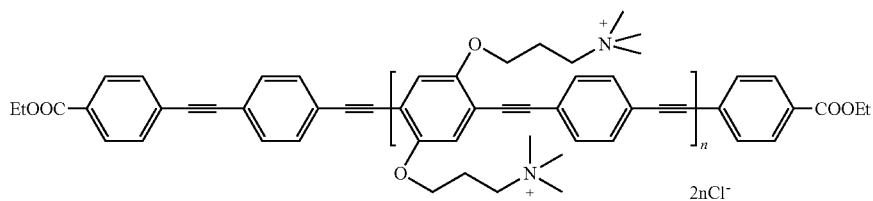<br>(n is about 5) |
| PPE—NMe₃-7-COOEt | 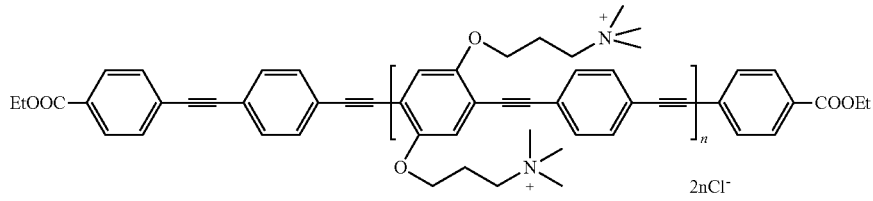<br>(n is about 7) |
| PPE—NMe₃-9-COOEt | 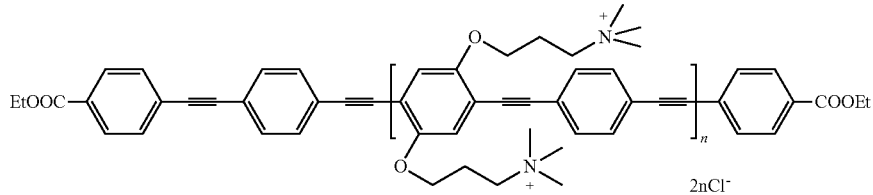<br>(n is about 9) |

TABLE 5-continued
| Name | Structure |
|---|---|
| PPE—NMe₃-11-COOEt | 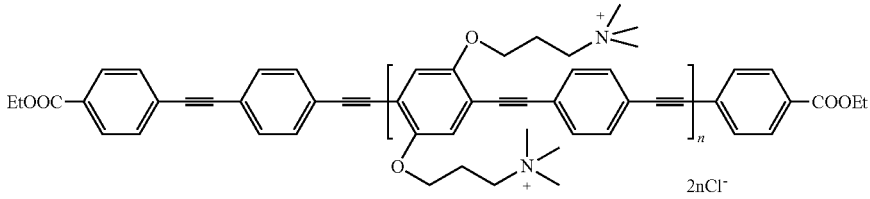<br>(n is about 11) |
| PPE—NMe₃-14-COOEt | 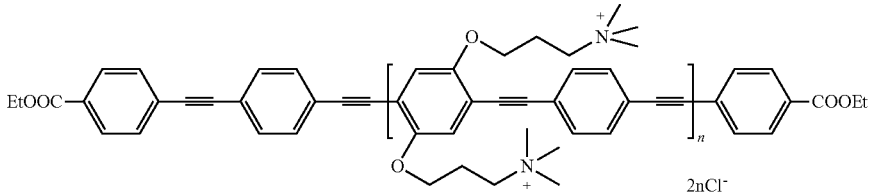<br>(n is about 14) |
| PPE—NMe₃-20-COOEt | 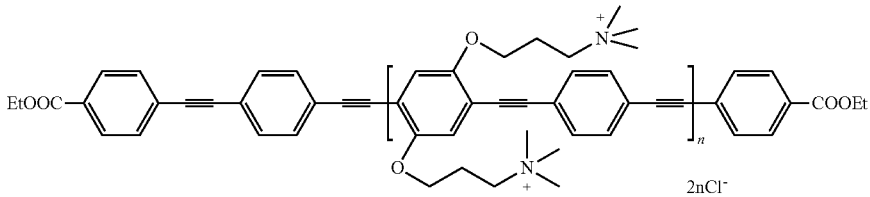<br>(n is about 20) |
| PPE—NMe₃-49-COOEt | 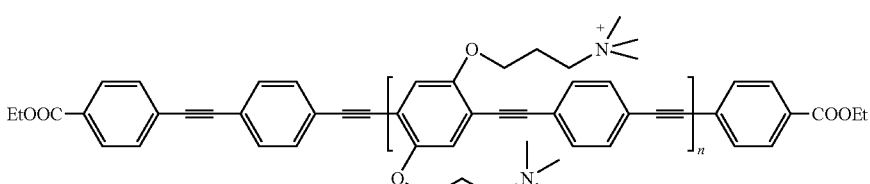<br>(n is about 49) |
| PPE—NMe₃-7-COOH | 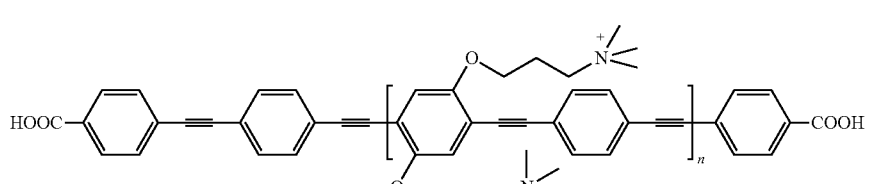<br>(n is about 7) |
| PPE—NMe₃-9-COOH | 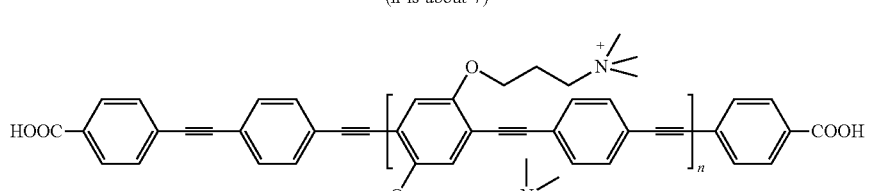<br>(n is about 9) |

TABLE 5-continued
| Name | Structure |
|---|---|
| PPE—NMe₃-11-COOH | 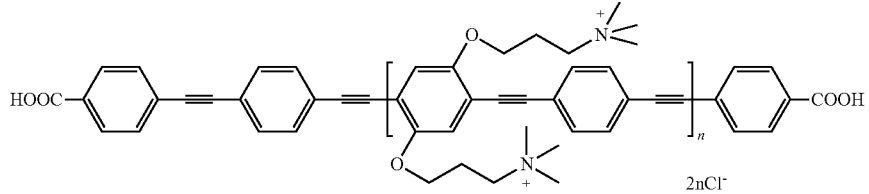 (n is about 11) |
| PPE—NMe₃-14-COOH | 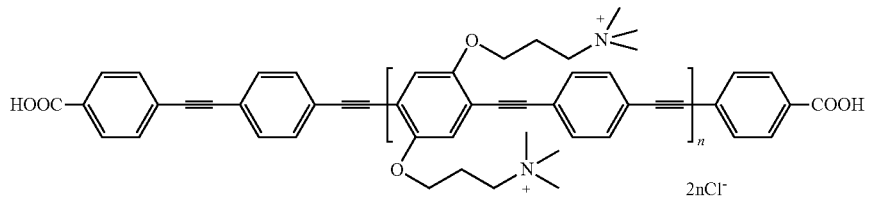 (n is about 14) |
| PPE—NMe₃-20-COOH | 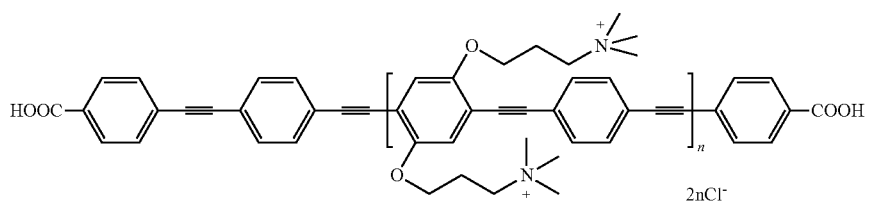 (n is about 20) |
| OPE006 | 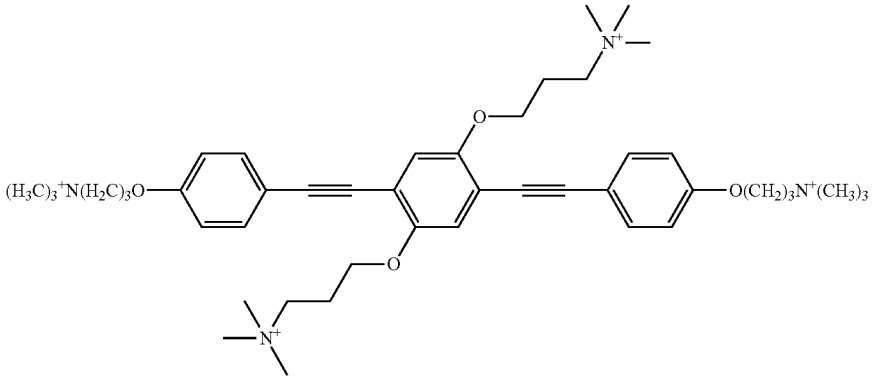 |
| OPE008 | 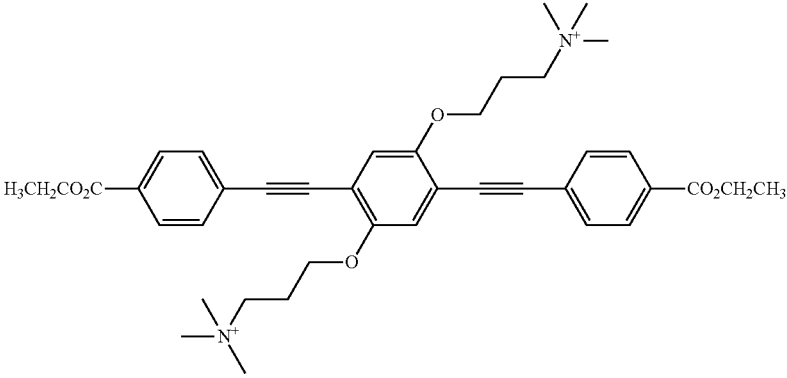 |

Example 2.5

Synthesis of Antimicrobial Compounds

A number of wipes may be prepared employing the fabrication procedure discussed in Example 1 using the compounds listed in Table 5 of Example 2.4. For example, a wipe may be coated with one of the compounds listed in Table 1 or more than one of the compounds listed in Table 5.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a conjugated polyelectrolyte comprising a subunit having the following structure:

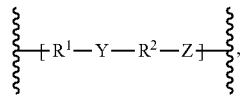

wherein at each occurrence, $R^1$ is independently chosen from:

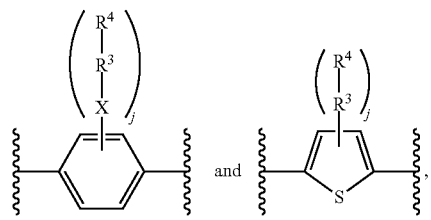

at each occurrence, j is independently chosen from 0, 1, 2, 3, and 4.

at each occurrence, X is a bond, —O—, —NH—, or —S—, at each occurrence, $R^3$ is a $(C_1\text{-}C_{20})$hydrocarbylene interrupted by 0, 1, 2, 3, 4, 5, 6, 7, 8, or 9 heteroatoms, at each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$, at each occurrence, $R^5$ is independently chosen from a substituted or unsubstituted $(C_1\text{-}C_{10})$hydrocarbyl, at each occurrence, Y is independently chosen from a bond and —C≡C—, at each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is independently chosen from a bond and —C≡C—.

Embodiment 2 provides the conjugated polyelectrolyte of Embodiment 1, further comprising one or more charge-balancing counterions.

Embodiment 3 provides the conjugated polyelectrolyte of any one of Embodiments 1-2, comprising terminal groups independently chosen from —H, -L-H, -L-C≡CH, -L-C≡CH, -L-$R^T$, -L-$R^T$, -L-C≡C—$R^T$, -L-C≡C—$R^L$—$R^T$, and -L-$R^L$—C≡C—$R^L$—$R^T$, -L-C≡C—$R^L$—C≡C—$R^L$—$R^T$, wherein at each occurrence, $R^T$ is independently chosen from —H, —Br, —$(C_1\text{-}C_{10})$alkyl, —C(O)—OH, —C(O)—O$((C_1\text{-}C_{10})$alkyl), —$(C_1\text{-}C_{10})$alkylene-N$((C_1\text{-}C_{10})$alkyl$)_3^+X^-$, —O—$(C_1\text{-}C_{10})$alkylene-N$((C_1\text{-}C_{10})$alkyl$)_3^+X^-$, wherein $X^-$ is a counterion, at each occurrence, $R^L$ is independently chosen from a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, naphthylene, and -(1,4-substituted 1,4-diazabicyclo[2.2.2]octane-1,4-diium)-, and at each occurrence, L is independently chosen from a bond, —$(C_1\text{-}C_{10})$alkylene-, and —O—$(C_1\text{-}C_{10})$alkylene-.

Embodiment 4 provides the conjugated polyelectrolyte of any one of Embodiments 1-3, wherein at each occurrence, $R^1$ is independently chosen from:

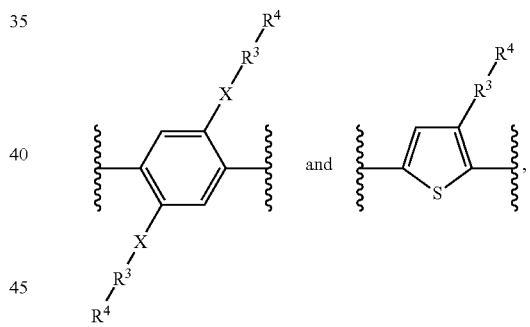

Embodiment 5 provides the conjugated polyelectrolyte of any one of Embodiments 1-4 comprising the structure:

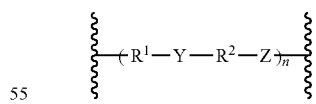

wherein n is about 1 to about 10,000.

Embodiment 6 provides the conjugated polyelectrolyte of any one of Embodiments 1-5, wherein $R^4$ is:

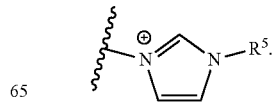

Embodiment 7 provides the conjugated polyelectrolyte of any one of Embodiments 1-6, wherein $R^4$ is:

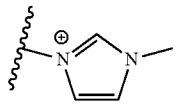

Embodiment 8 provides the conjugated polyelectrolyte of any one of Embodiments 1-7, wherein:
$R^1$ has the structure:

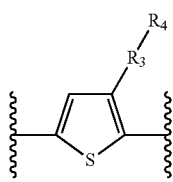

at each occurrence, $R^3$ is independently chosen from a $(C_1-C_{10})$alkylene, at each occurrence, $R^1$ is independently chosen from -(1,4-substituted 1,4-diazabicyclo[2.2.2]octane-1,4-diium)-$R^5$, 3-$R^5$-substituted-imidazolium, pyridinium, and —$N^+(R^5)_3$, at each occurrence, $R^5$ is independently chosen from $(C_1-C_{10})$alkyl, at each occurrence, Y is a bond, at each occurrence, $R^2$ is independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is a bond.

Embodiment 9 provides the conjugated polyelectrolyte of Embodiment 8, wherein $R^4$ is independently chosen from -(1,4-substituted 1,4-diazabicyclo[2.2.2]octane-1,4-diium)-$(C_1-C_{10})$alkyl, 3-methylimidazolium, pyridinium, and —$N^+((C_1-C_5)$alkyl$)_3$.

Embodiment 10 provides the conjugated polyelectrolyte of any one of Embodiments 8-9, wherein Y, $R^2$, and Z are a bond.

Embodiment 11 provides the conjugated polyelectrolyte of any one of Embodiments 1-10, wherein:
$R^1$ has the structure:

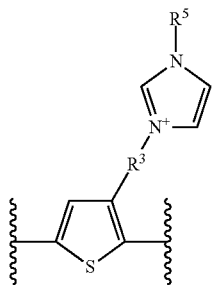

at each occurrence, $R^3$ is independently chosen from a $(C_1-C_{20})$hydrocarbylene interrupted by 0, 1, 2, 3, 4, 5, 6, 7, 8, or 9 heteroatoms, at each occurrence, $R^5$ is independently chosen from a substituted or unsubstituted $(C_1-C_{10})$hydrocarbyl, at each occurrence, Y is a bond, at each occurrence, $R^2$ is independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is a bond.

Embodiment 12 provides the conjugated polyelectrolyte of Embodiment 11, wherein:

at each occurrence, $R^3$ is a $(C_1-C_{10})$alkylene interrupted by 0, 1, 2, 3, or 4 oxygen atoms, at each occurrence, $R^5$ is independently chosen from a $(C_1-C_5)$alkyl, at each occurrence, Y is a bond, at each occurrence, $R^2$ is a bond, and at each occurrence, Z is a bond.

Embodiment 13 provides the conjugated polyelectrolyte of Embodiment 12, comprising the following structure:

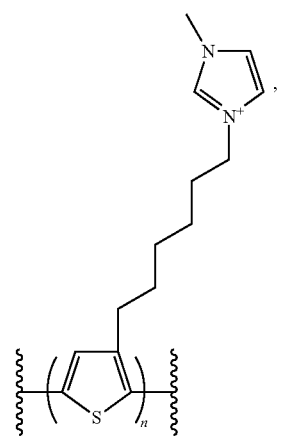

wherein n is about 1 to about 10.000.

Embodiment 14 provides the conjugated polyelectrolyte of any one of Embodiments 4-13, wherein at each occurrence, X is —O—, at each occurrence, $R^3$ is a $(C_2-C_4)$alkylene, at each occurrence, Y is —C≡C—, at each occurrence, $R^2$ is a bond, at each occurrence, Z is a bond, and at each occurrence, —$R^4$ is chosen from —$N^+(CH_3)_3$, —$N(CH_3)_2$, —$SO_3^-$,

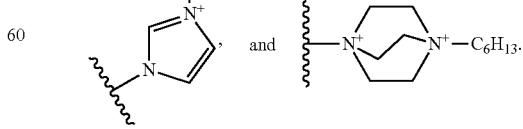

Embodiment 15 provides the conjugated polyelectrolyte of any one of Embodiments 1-14, wherein at each occurrence, R¹ has the structure:

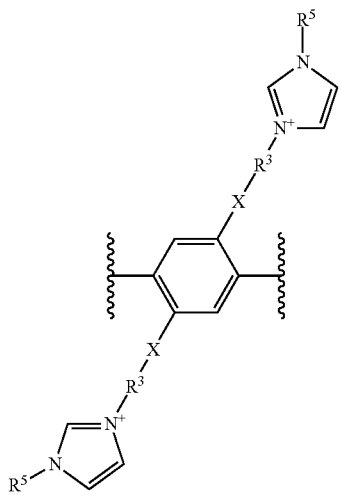

at each occurrence, X is a bond, —O—, —NH—, or —S—, at each occurrence, R³ is independently chosen from a $(C_1-C_{20})$hydrocarbylene interrupted by 0, 1, 2, 3, 4, 5, 6, 7, 8, or 9 heteroatoms, at each occurrence, R⁵ is independently chosen from a substituted or unsubstituted $(C_1-C_{10})$hydrocarbyl, at each occurrence, Y is independently chosen from a bond and —C≡C—, at each occurrence, R² is independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is independently chosen from a bond and —C≡C—.

Embodiment 16 provides the conjugated polyelectrolyte of Embodiment 15, wherein at each occurrence, X is —O—, at each occurrence, R³ is a $(C_1-C_{10})$alkylene interrupted by 0, 1, 2, 3, or 4 oxygen atoms, at each occurrence, R⁵ is independently chosen from a $(C_1-C_5)$alkyl, at each occurrence, Y is —C≡C—, at each occurrence, R² is a bond, and at each occurrence, Z is a bond.

Embodiment 17 provides the conjugated polyelectrolyte of Embodiment 16, comprising the following structure:

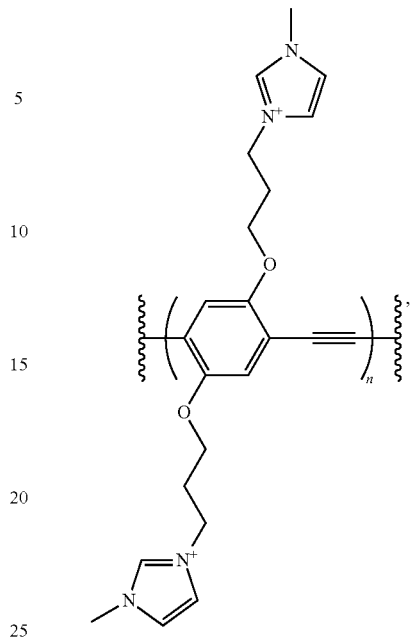

wherein n is about 1 to 10,000.

Embodiment 18 provides the conjugated polyelectrolyte of any one of Embodiments 4-17, wherein at each occurrence, X is —O—, at each occurrence, R³ is a $(C_2-C_4)$alkylene, at each occurrence, Y is —C≡C—, at each occurrence, R² is independently chosen from a 1,4-substituted phenylene and a 2,5-substituted thiophenylene, at each occurrence, Z is a —C≡C—, and at each occurrence, R⁴ is independently chosen from —N⁺(CH₃)₃, —N(CH₃)₂, —SO₃⁻,

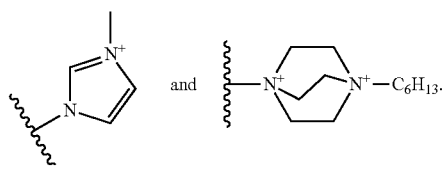

Embodiment 19 provides the conjugated polyelectrolyte of any one of Embodiments 1-18 wherein at each occurrence, R² is independently chosen from

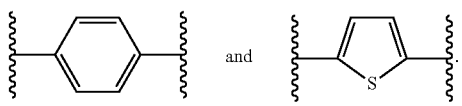 [SMILES: *c1ccc(*)cc1 ; *c1ccc(*)s1]

Embodiment 20 provides the conjugated polyelectrolyte of any one of Embodiments 1-19, wherein R² is

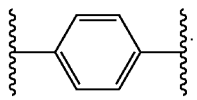

Embodiment 21 provides the conjugated polyelectrolyte of any one of Embodiments 15-20, wherein
at each occurrence, X is —O—,
at each occurrence, $R^3$ is a $(C_1$-$C_{10})$alkylene interrupted by 0, 1, 2, 3, or 4 oxygen atoms,
at each occurrence, $R^5$ is independently $(C_1$-$C_5)$alkyl,
at each occurrence, Y is —C≡C—,
at each occurrence, $R^2$ is a phenylene, and
at each occurrence, Z is a —C≡C—.

Embodiment 22 provides the conjugated polyelectrolyte of Embodiment 21, comprising the following structure:

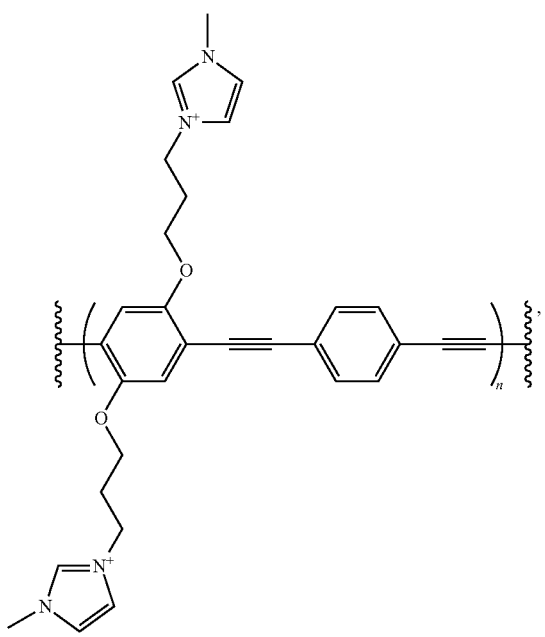

wherein n is about 1 to about 10,000.

Embodiment 23 provides the conjugated polyelectrolyte of any one of Embodiments 1-22, wherein
at each occurrence, $R^1$ has the structure:

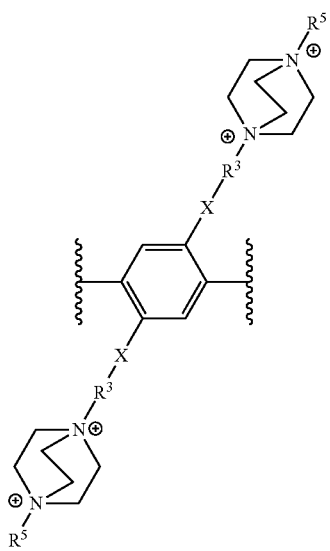

at each occurrence, X is a bond, —O—, —NH—, or —S—, at each occurrence, $R^3$ is independently chosen from a $(C_1$-$C_{20})$hydrocarbylene interrupted by 0, 1, 2, 3, 4, 5, 6, 7, 8, or 9 heteroatoms,
at each occurrence, $R^5$ is independently chosen from a substituted or unsubstituted $(C_1$-$C_{10})$hydrocarbyl,
at each occurrence, Y is independently chosen from a bond and —C≡C—.
at each occurrence, $R^2$ is independently chosen from a bond, phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and
at each occurrence, Z is independently chosen from a bond and —C≡C—.

Embodiment 24 provides the conjugated polyelectrolyte of Embodiment 23, wherein
at each occurrence, X is —O—,
at each occurrence, $R^3$ is a $(C_1$-$C_{10})$alkylene interrupted by 0, 1, 2, 3, or 4 oxygen atoms,
at each occurrence, $R^5$ is independently chosen from a $(C_1$-$C_5)$alkyl,
at each occurrence, Y is —C≡C—,
at each occurrence, $R^2$ is a phenylene, and
at each occurrence, Z is a —C≡C—.

Embodiment 25 provides the conjugated polyelectrolyte of Embodiment 24, wherein —X—$R^3$—$R^4$ has the structure:

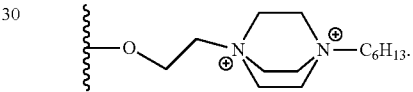

Embodiment 26 provides the conjugated polyelectrolyte of any one of Embodiments 23-25, comprising the structure:

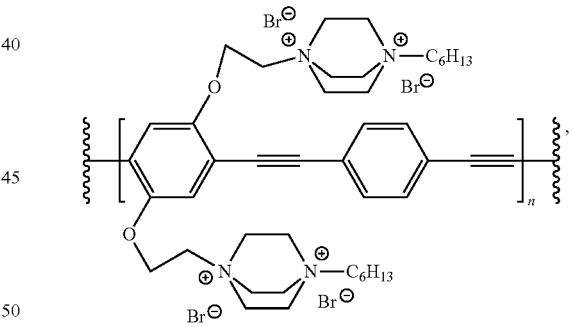

wherein n is about 1 to about 10,000.

Embodiment 27 provides the conjugated polyelectrolyte of any one of Embodiments 23-26, having the structure:

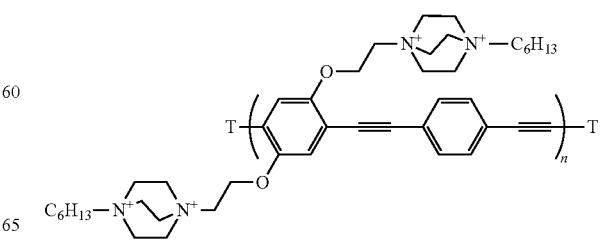

wherein
at each occurrence, T is independently chosen from —H, —Br, —C≡CH, and —C$_6$H$_5$, and
n is about 1 to about 2000.

Embodiment 28 provides the conjugated polyelectrolyte of any one of Embodiments 1-27, having the following structure:

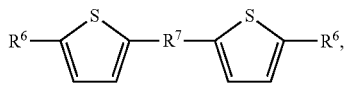

wherein
at each occurrence, R$^7$ is independently chosen from —(C$_1$-C$_5$)alkyl-N$^+$((C$_1$-C$_5$)alkyl)$_3$, and
R$^6$ is chosen from

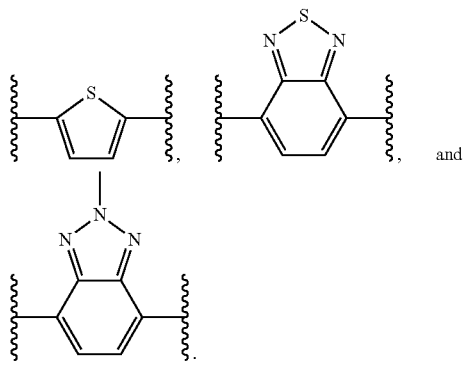

Embodiment 29 provides an antimicrobial substrate, the antimicrobial substrate comprising:
the conjugated polyelectrolyte of any one of Embodiments 1-28; and
a substrate.

Embodiment 30 provides the antimicrobial substrate of Embodiment 29, wherein in the substrate is chosen from a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

Embodiment 31 provides the antimicrobial substrate of any one of Embodiments 29-30, wherein the substrate is a wipe.

Embodiment 32 provides the antimicrobial substrate of any one of Embodiments 29-31, wherein the conjugated polyelectrolyte is non-leachably bound to the substrate.

Embodiment 33 provides the antimicrobial substrate of any one of Embodiments 29-32, wherein the conjugated polyelectrolyte is in contact with at least one surface of the substrate.

Embodiment 34 provides the antimicrobial substrate of any one of Embodiments 29-33, wherein at least one or more layers separate the conjugated polyelectrolyte from the substrate.

Embodiment 35 provides the antimicrobial substrate of any one of Embodiments 29-34, wherein the conjugated polyelectrolyte is uniformly distributed on the substrate.

Embodiment 36 provides the antimicrobial substrate of any one of Embodiments 29-35, wherein the antimicrobial substrate exhibits antimicrobial properties comprising prevention of growth of at least one of Gram-positive *Staphylococcus aureus*. Gram-negative *Pseudomonas aeruginosa*, and *Escherichia coli*.

Embodiment 37 provides the antimicrobial substrate of any one of Embodiments 29-36, wherein the antimicrobial properties of the antimicrobial substrate exceed the antimicrobial properties of a corresponding substrate without the antimicrobial compound.

Embodiment 38 provides the antimicrobial substrate of any one of Embodiments 29-37, wherein the antimicrobial substrate exhibits antimicrobial properties in a non-aqueous environment.

Embodiment 39 provides a method of inactivating a microorganism, comprising contacting the microorganism with an effective amount or concentration of the conjugated polyelectrolyte of any one of Embodiments 1-28.

Embodiment 40 provides the method of Embodiment 39, wherein the microorganism comprises at least one of a bacterium, virus, fungus, mold, slime mold, algae, and yeast.

Embodiment 41 provides the method of any one of Embodiments 39-40, wherein the inactivating of the microorganism is accomplished in a shorter period of time in the presence light as compared to a corresponding method in the absence of light.

Embodiment 42 provides a method of disinfecting an object, comprising contacting the object with an effective amount or concentration of the conjugated polyelectrolyte of any one of Embodiments 1-41.

Embodiment 43 provides the method of Embodiment 42, wherein the disinfecting of an object is accomplished in a shorter period of time in the presence of light as compared to a corresponding method in the absence of light.

Embodiment 44 provides a method of treating a substrate, the method comprising:
contacting the substrate the conjugated polyelectrolyte of any one of Embodiments 1-43;
wherein the contacted substrate has antimicrobial properties.

Embodiment 45 provides the method of Embodiment 44, wherein the antimicrobial properties comprises prevention of growth of at least one of Gram-positive *Staphylococcus aureus*, Gram-negative *Pseudomonas aeruginosa*, and *Escherichia coli*.

Embodiment 46 provides the method of any one of Embodiments 44-45, wherein the antimicrobial properties of the contacted substrate exceed the antimicrobial properties of the substrate prior to the contacting.

Embodiment 47 provides the method of any one of Embodiments 44-46, wherein the contacted substrate has antimicrobial properties in a non-aqueous environment.

Embodiment 48 provides the method of any one of Embodiments 44-47, wherein the substrate is at least one of a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

Embodiment 49 provides the method of any one of Embodiments 44-48, wherein the contacting is accomplished with at least one of foamed applicators, cotton swabs, saturated swab sticks, saturated wipes, aerosols, sprays, brushes, and dips.

Embodiment 50 provides an antimicrobial substrate comprising:

an antimicrobial compound, wherein the antimicrobial compound is a conjugated polyelectrolyte comprising a subunit having the following structure:

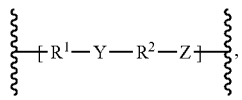

wherein at each occurrence, $R^1$ is independently chosen from:

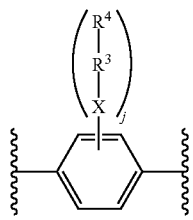 and 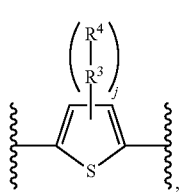, at each occurrence, j is independently chosen from 0, 1, 2, 3, and 4, at each occurrence, X is a bond, —O—, —NH—, or —S—.

at each occurrence, $R^3$ is a $(C_1\text{-}C_{20})$hydrocarbylene interrupted by 0, 1, 2, 3, 4, 5, 6, 7, 8, or 9 heteroatoms, at each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$, at each occurrence, $R^5$ is independently chosen from a substituted or unsubstituted $(C_1\text{-}C_{10})$hydrocarbyl.

at each occurrence, Y is independently chosen from a bond and —C≡C—, at each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is independently chosen from a bond and —C≡C—; and a substrate.

Embodiment 51 provides a method of treating a substrate, the method comprising:

contacting the substrate with a conjugated polyelectrolyte comprising a repeating unit having the following structure:

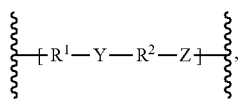

wherein at each occurrence, $R^1$ is independently chosen from:

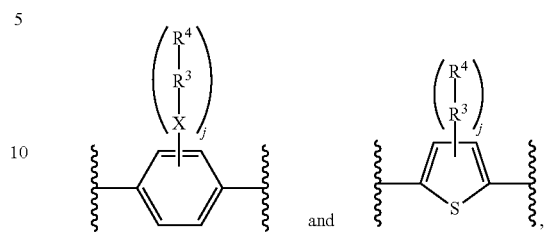

at each occurrence, j is independently chosen from 0, 1, 2, 3, and 4, at each occurrence, X is a bond, —O—, —NH—, or —S—.

at each occurrence, $R^3$ is a $(C_1\text{-}C_{20})$hydrocarbylene interrupted by 0, 1, 2, 3, 4, 5, 6, 7, 8, or 9 heteroatoms, at each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$, at each occurrence, $R^5$ is independently chosen from a substituted or unsubstituted $(C_1\text{-}C_{10})$hydrocarbyl, at each occurrence, Y is independently chosen from a bond and —C≡C—, at each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and at each occurrence, Z is independently chosen from a bond and —C≡C—;

wherein the contacted substrate has antimicrobial properties.

Embodiment 52 provides the conjugated polyelectrolyte, method, or antimicrobial substrate of any one or any combination of Embodiments 1-51 optionally configured such that all elements or options recited are available to use or select from.

What is claimed is:

1. An antimicrobial substrate, the antimicrobial substrate comprising:

a substrate; and a conjugated polyelectrolyte comprising a subunit having the following structure:

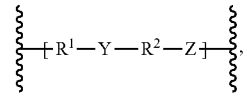

wherein
at each occurrence, $R^1$ has the structure:

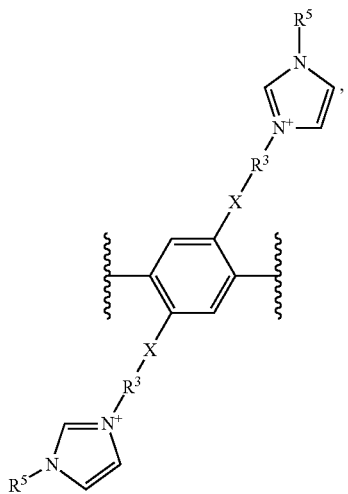

at each occurrence, X is a bond, —O—, —NH—, or —S—,
at each occurrence, $R^3$ is a $(C_1-C_{20})$hydrocarbylene interrupted by 0, 1, 2, 3, 4, 5, 6, 7, 8, or 9 heteroatoms,
at each occurrence, $R^5$ is independently chosen from a substituted or unsubstituted $(C_1-C_{10})$hydrocarbyl,
at each occurrence, Y is independently chosen from a bond and —C≡C—,
at each occurrence, $R^2$ is independently chosen from a bond, a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, and naphthylene, and
at each occurrence, Z is independently chosen from a bond and —C≡C—.

2. The antimicrobial substrate of claim 1, wherein in the substrate is chosen from a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

3. The antimicrobial substrate of claim 1, wherein the conjugated polyelectrolyte comprises terminal groups independently chosen from —H, -L-H, -L-C≡CH, -L-C≡CH, -L-$R^T$, -L-$R^L$—$R^T$, -L-C≡C—$R^T$, -L-C≡C—$R^L$—$R^T$, and -L-$R^L$—C≡C—$R^L$—$R^T$, -L-C≡C—$R^L$—C≡C—$R^L$—$R^T$, wherein
at each occurrence, $R^T$ is independently chosen from —H, —Br, —$(C_1-C_{10})$alkyl, —C(O)—OH, —C(O)—O$((C_1-C_{10})$alkyl), —$(C_1-C_{10})$alkylene-N$((C_1-C_{10})$alkyl)$_3^+$X$^-$, —O—$(C_1-C_{10})$alkylene-N$((C_1-C_{10})$alkyl)$_3^+$X$^-$, wherein X$^-$ is a counterion,
at each occurrence, $R^L$ is independently chosen from a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, naphthylene, and -(1,4-substituted 1,4-diazabicyclo[2.2.2]octane-1,4-diium)-, and
at each occurrence, L is independently chosen from a bond, —$(C_1-C_{10})$alkylene-, and —O—$(C_1-C_{10})$alkylene-.

4. The antimicrobial substrate of claim 1, wherein
at each occurrence, X is —O—,
at each occurrence, $R^3$ is a $(C_2-C_4)$akylene,
at each occurrence, Y is —C≡C—,
at each occurrence, $R^2$ is a bond, and
at each occurrence, Z is a bond.

5. The antimicrobial substrate of claim 1, wherein
at each occurrence, X is —O—,
at each occurrence, $R^3$ is a $(C_1-C_{10})$alkylene interrupted by 0, 1, 2, 3, or 4 oxygen atoms,
at each occurrence, $R^5$ is independently chosen from a $(C_1-C_5)$alkyl,
at each occurrence, Y is —C≡C—,
at each occurrence, $R^2$ is a bond, and
at each occurrence, Z is a bond.

6. The antimicrobial substrate of claim 1, wherein
at each occurrence, X is —O—,
at each occurrence, $R^3$ is a $(C_2-C_4)$alkylene,
at each occurrence, Y is —C≡C—,
at each occurrence, $R^2$ is independently chosen from a 1,4-substituted phenylene and a 2,5-substituted thiophenylene, and
at each occurrence, Z is a —C≡C—.

7. The antimicrobial substrate of claim 1, wherein
at each occurrence, X is —O—,
at each occurrence, $R^3$ is a $(C_1-C_{10})$alkylene interrupted 0, 1, 3, or 4 oxygen atoms,
at each occurrence, $R^5$ is independently $(C_1-C_5)$alkyl,
at each occurrence, Y is —C≡C—,
at each occurrence, $R^2$ is a phenylene, and
at each occurrence, Z is a —C≡C—.

8. The antimicrobial substrate of claim 1, wherein the conjugated polyelectrolyte is non-leachably bound to the substrate.

9. The antimicrobial substrate of claim 1, wherein the antimicrobial substrate exhibits antimicrobial properties comprising prevention of growth of at least one of Gram-positive *Staphylococcus aureus*, Gram-negative *Pseudomonas aeruginosa*, and *Escherichia coli*, wherein the antimicrobial properties of the antimicrobial substrate exceed the antimicrobial properties of a corresponding substrate without the antimicrobial compound.

10. An antimicrobial substrate, the antimicrobial substrate comprising:
a substrate; and
a conjugated polyelectrolyte comprising a subunit having the following structure:

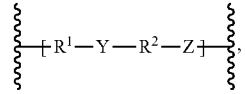

wherein at each occurrence, $R^1$ is independently chosen from:

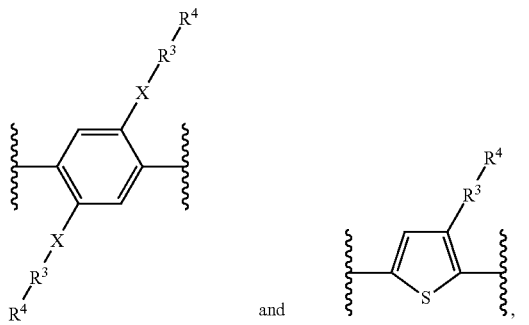 and 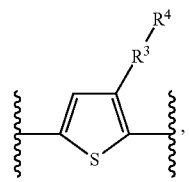, at each occurrence, X is —O—, —NH—, or —S—, at each occurrence, $R^3$ is a ($C_1$-$C_{20}$)hydrocarbylene interrupted by 0, 1, 2, 3, 4, 5, 6, 7, 8, or 9 heteroatoms, at each occurrence, $R^4$ is independently chosen from —H, —$R^5$, -(1,4-substituted 1,4-diazabicyclo[2.2.2]octane-1,4-diium)-$R^5$, 3-$R^5$-substituted imidazolium, pyridinium, —$SO_3^-$, —$CO_2H$, —$CO_2^-$, —$N^+(R^5)_3$, and —$N(R^5)_2$, at each occurrence, $R^5$ is independently chosen from a substituted or unsubstituted ($C_1$-$C_{10}$)hydrocarbyl, at each occurrence, Y is independently chosen from a bond and —C≡C—, at each occurrence, $R^2$ is a bond, and at each occurrence, Z is a bond.

11. The antimicrobial substrate of claim 10, wherein in the substrate is chosen from a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

12. The antimicrobial substrate of claim 10, wherein the conjugated polyelectrolyte comprises terminal groups independently chosen from —H, -L-H, -L-C≡CH, -L-$R^T$, -L-$R^L$—$R^T$, -L-C≡C—$R^T$, -L-C≡C—$R^L$—$R^T$, and -L-$R^L$—C≡C—$R^L$—$R^T$, -L-C≡C—$R^L$—C≡C—$R^L$—$R^T$, wherein at each occurrence, $R^T$ is independently chosen from —H, —Br, —($C_1$-$C_{10}$)alkyl, —C(O)—OH, —C(O)—O(($C_1$-$C_{10}$)alkyl), —($C_1$-$C_{10}$)alkylene-N(($C_1$-$C_{10}$)alkyl)$_3^+$$X^-$, —O—($C_{10}$-$C_{10}$)alkylene-N(($C_1$-$C_{10}$)alkyl)$_3^+$$X^-$, wherein $X^-$ is a counterion, at each occurrence, $R^L$ is independently chosen from a substituted or unsubstituted phenylene, thiophenylene, azulenylene, heptalenylene, biphenylene, indacenylene, fluorenylene, phenanthrenylene, triphenylenylene, pyrenylene, naphthacenylene, chrysenylene, biphenylenylene, anthracenylene, naphthylene, and -(1,4-substituted 1,4-diazabicyclo[2.2.2]octane-1,4-diium)-, and at each occurrence, L is independently chosen from a bond, —($C_1$-$C_{10}$)alkylene-, and —O—($C_1$-$C_{10}$)alkylene-.

13. The antimicrobial substrate of claim 10, wherein:

$R^1$ has the structure:

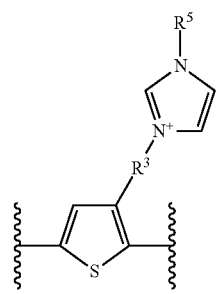, at each occurrence, $R^3$ is independently chosen from a ($C_1$-$C_{10}$)alkylene, at each occurrence, $R^4$ is independently chosen from -(1,4-substituted 1,4-diazabicyclo[2.2.2]octane-1,4-diium)-$R^5$, 3-$R^5$-substituted-imidazolium, pyridinium, and —$N^+(R^5)_3$, at each occurrence, $R^5$ is independently chosen from ($C_1$-$C_{10}$)alkyl, and at each occurrence, Y is a bond.

14. The antimicrobial substrate of claim 10, wherein:

$R^1$ has the structure:

at each occurrence, $R^3$ is independently chosen from a ($C_1$-$C_{20}$)hydrocarbylene interrupted by 0, 1, 2, 3, 4, 5, 6, 7, 8, or 9 heteroatoms, at each occurrence, $R^5$ is independently chosen born a substituted or unsubstituted ($C_1$-$C_{10}$)hydrocarbyl, and at each occurrence, Y is a bond.

15. The antimicrobial substrate of claim 14, wherein:

at each occurrence, $R^3$ is a ($C_1$-$C_{10}$)alkylene interrupted by 0, 1, 2, 3, or 4 oxygen atoms, at each occurrence, $R^5$ is independently chosen from a ($C_1$-$C_5$)alkyl, and at each occurrence, Y is a bond.

16. The antimicrobial substrate of claim 10, wherein at each occurrence, X is —O—, at each occurrence, $R^3$ is a ($C_2$-$C_4$)alkylene, at each occurrence, Y is —C≡C—, and at each occurrence, —$R^4$ is chosen from —$N^+(CH_3)_3$, —$N(CH_3)_2$, —$SO_3^-$,

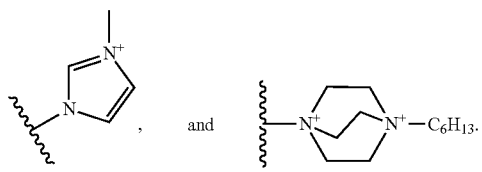

17. The antimicrobial substrate of claim 10, wherein at each occurrence, $R^1$ has the structure:

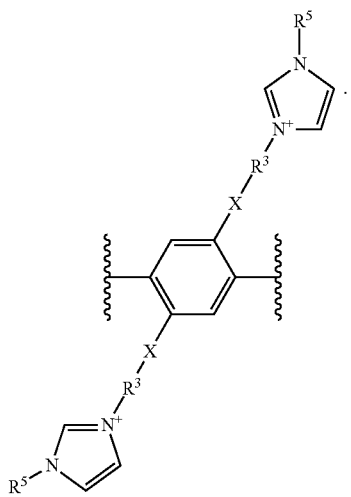

18. The antimicrobial substrate of claim 10, wherein at each occurrence, $R^1$ has the structure:

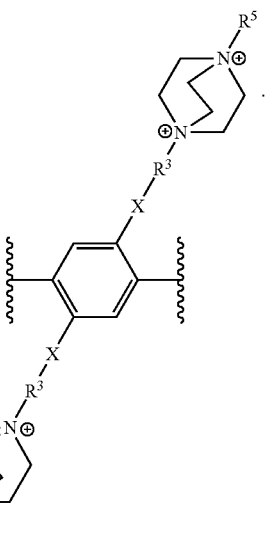

19. The antimicrobial substrate of claim 10, wherein the conjugated polyelectrolyte is non-leachably bound to the substrate.

20. The antimicrobial substrate of claim 10, wherein the antimicrobial substrate exhibits antimicrobial properties comprising prevention of growth of at least one of Gram-positive *Staphylococcus aureus*, Gram-negative *Pseudomonas aeruginosa*, and *Escherichia coli*, wherein the antimicrobial properties of the antimicrobial substrate exceed the antimicrobial properties of a corresponding substrate without the antimicrobial compound.

* * * * *

UNITED STATES PATENT AND TRADEMARK OFFICE
CERTIFICATE OF CORRECTION

PATENT NO. : 9,750,250 B2
APPLICATION NO. : 15/018179
DATED : September 5, 2017
INVENTOR(S) : Whitten et al.

It is certified that error appears in the above-identified patent and that said Letters Patent is hereby corrected as shown below:

On the Title Page

On page 2, in Column 2, under "Other Publications", Line 61, delete "Requriement" and insert --Requirement-- therefor On page 4, in Column 1, under "Other Publications", Line 17, delete "tTeatment" and insert --Treatment-- therefor On page 4, in Column 1, under "Other Publications", Line 30, delete "E?ects" and insert --Effects-- therefor On page 4, in Column 2, under "Other Publications", Line 61, delete "Polyelecrolyte-Grafted" and insert --Polyelectrolyte-Grafted-- therefor On page 4, in Column 2, under "Other Publications", Line 71, delete "Abilitty" and insert --Ability-- therefor On page 5, in Column 2, under "Other Publications", Line 24, delete "electronc" and insert --electron-- therefor On page 5, in Column 2, under "Other Publications", Line 66, delete "Actino" and insert --Action-- therefor In the Claims In Column 69, Line 2, in Claim 1, delete "$R^1$has" and insert --$R^1$ has-- therefor In Column 70, Line 10, in Claim 4, delete "($C_2$-$C_4$)akylene," and insert --($C_2$-$C_4$)alkylene,-- therefor In Column 70, Line 36-37, in Claim 7, delete "0, 1, 3," and insert --by 0, 1, 2, 3,-- therefor Signed and Sealed this
Tenth Day of July, 2018

Andrei Iancu
*Director of the United States Patent and Trademark Office*

In Column 71, Line 48, in Claim 12, delete "-L-C≡CH," and insert -- -L-C≡CH, -L-C≡CH,-- therefor In Column 71, Line 51, in Claim 12, delete "$R^T$is" and insert --$R^T$ is-- therefor In Column 71, Line 54-55, in Claim 12, delete "-O-$(C_{10}$-$C_{10})$alkylene-N$((C_1$-$C_{10})$alkyl$)_3^+$X$^-$," and insert -- -O-$(C_1$-$C_{10})$alkylene-N$((C_1$-$C_{10})$alkyl$)_3^+$X$^-$,-- therefor In Column 72, Line 49, in Claim 14, delete "born" and insert --from-- therefor